(12) United States Patent
Anderson et al.

(10) Patent No.: US 12,421,283 B2
(45) Date of Patent: Sep. 23, 2025

(54) COMPOSITIONS AND METHODS FOR TREATMENT OF CYTOMEGALOVIRUS

(71) Applicant: Variation Biotechnologies Inc., Ottawa (CA)

(72) Inventors: David E. Anderson, Newton, MA (US); Anne-Catherine Fluckiger, Saint Genis les Ollières (FR)

(73) Assignee: Variation Biotechnologies Inc., Ottawa (CA)

(*) Notice: Subject to any disclaimer, the term of this patent is extended or adjusted under 35 U.S.C. 154(b) by 444 days.

(21) Appl. No.: 17/670,052

(22) Filed: Feb. 11, 2022

(65) Prior Publication Data

US 2023/0272013 A1 Aug. 31, 2023

Related U.S. Application Data

(63) Continuation of application No. 15/683,355, filed on Aug. 22, 2017, now Pat. No. 11,248,026, which is a continuation of application No. 14/357,423, filed as application No. PCT/IB2012/002854 on Nov. 9, 2012, now Pat. No. 9,777,043.

(60) Provisional application No. 61/654,157, filed on Jun. 1, 2012, provisional application No. 61/558,800, filed on Nov. 11, 2011.

(51) Int. Cl.
| | | |
|---|---|---|
| *C07K 14/005* | (2006.01) | |
| *A61K 39/00* | (2006.01) | |
| *A61K 39/245* | (2006.01) | |

(52) U.S. Cl.
CPC .......... *C07K 14/005* (2013.01); *A61K 39/245* (2013.01); *A61K 2039/5258* (2013.01); *A61K 2039/70* (2013.01); *C07K 2319/00* (2013.01); *C07K 2319/03* (2013.01); *C12N 2710/16134* (2013.01); *C12N 2740/13023* (2013.01); *C12N 2760/20234* (2013.01)

(58) Field of Classification Search
CPC .............. C07K 14/005; C07K 2319/00; C07K 2319/03; A61K 39/245; A61K 2039/5258; A61K 2039/70; A61K 39/12; C12N 2710/16134; C12N 2740/13023; C12N 2760/20234; C12N 2760/20245; A61P 31/22; A61P 31/20
See application file for complete search history.

(56) References Cited

U.S. PATENT DOCUMENTS

| | | |
|---|---|---|
| 4,694,074 A | 9/1987 | Uemura et al. |
| 6,440,730 B1 | 8/2002 | Von Laer et al. |
| 8,673,612 B2 | 3/2014 | Klatzmann et al. |
| 9,777,043 B2 | 10/2017 | Anderson et al. |
| 11,248,026 B2 | 2/2022 | Anderson et al. |
| 2004/0071661 A1 | 4/2004 | Klatzmann et al. |
| 2006/0216702 A1 | 9/2006 | Compans et al. |
| 2009/0123494 A1 | 5/2009 | Staplin et al. |
| 2010/0047266 A1 | 2/2010 | Haynes |
| 2011/0250675 A1 | 10/2011 | Bennett |
| 2014/0308308 A1 | 10/2014 | Anderson et al. |
| 2017/0349634 A1 | 12/2017 | Anderson et al. |

FOREIGN PATENT DOCUMENTS

| | | |
|---|---|---|
| CN | 1376201 A | 10/2002 |
| CN | 106102769 A | 11/2016 |
| JP | 6232544 B2 | 11/2017 |
| RU | 2290204 C1 | 12/2006 |
| WO | WO-89/07143 A1 | 8/1989 |
| WO | WO-01/23414 A2 | 4/2001 |
| WO | WO-2008/094200 A2 | 8/2008 |
| WO | WO-2009/120883 A2 | 10/2009 |
| WO | WO-2010/128338 A2 | 11/2010 |
| WO | WO-2013/068847 A2 | 5/2013 |
| WO | WO-2015/089340 A1 | 6/2015 |

OTHER PUBLICATIONS

Foroogh Nejatollahi, Samantha J. Hodgetts, Pamela J. Vallely, James P. Burnie, Neutralising human recombinant antibodies to human cytomegalovirus glycoproteins GB and gH, FEMS Immunology & Medical Microbiology, vol. 34, Issue 3, Nov. 2002 pp. 237-244. (Year: 2002).*
GenBank: AAA45946.1 (1993, CMV gH) (Year: 1993).*
UniProtKB/Swiss-Prot: P13201.1 (1990, CMV GB) (Year: 1990).*
Arvin, A. M. et al., Vaccine development to prevent cytomegalovirus disease: report from the National Vaccine Advisory Committee, Clin Infect Dis., 39(2):233-9 (2004).
Atwood, T., The Babel of Bioinformatics, Science, 290(5491): 471-473 (2000).
Baker, D. and Sali, A., Protein Structure Prediction and Structural Genomics, Science, 294(5540): 93-96 (2001).
Baraniak, I. et al., Epitope-Specific Humoral Responses to Human Cytomegalovirus Glycoprotein-B Vaccine With MF59: Anti-AD2 Levels Correlate With Protection From Viremia, The Journal of Infectious Diseases, 217(12): 1907-1917 (2018).

(Continued)

*Primary Examiner* — Rachel B Gill
(74) *Attorney, Agent, or Firm* — Choate, Hall & Stewart LLP; Rolando Medina; Stephany Foster

(57) ABSTRACT

The present disclosure provides compositions and methods useful for treating HCMV infection. As described herein, the compositions and methods are based on development of immunogenic compositions that include virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to beneficial immune responses, for example that include both a humoral response (e.g., production of neutralizing antibodies) and a cellular response (e.g., T-cell activation).

17 Claims, 17 Drawing Sheets

Specification includes a Sequence Listing.

(56) References Cited

OTHER PUBLICATIONS

Baraniak, I. et al., Seronegative patients vaccinated with cytomegalovirus GB-MF59 vaccine have evidence of neutralising antibody responses against GB early post-transplantation, EbioMedicine, 50:45-54 (2019).
Berencsi, K. et al., A Canarypox Vector-Expressing Cytomegalovir (CMV) Phosphoprotein 65 Induces Long-Lasting Cytotoxic T Cell Responses in Human CMV-Seronegative Subjects, Journal of Infectious Diseases, 183(8):1171-1179 (2001).
Bernstein, D. et al., Effect of previous or simultaneous immunization with canarypox expressing cytomegalovirus (CMV) glycoprotein B (GB) on response to subunit GB vaccine plus MF59 in healthy CMV-seronegative adults, Journal of Infectious Diseases, 185(5):686-690 (2002).
Broer, R. et al., Important Role for the Transmembrane Domain of Severe Acute Respiratory Syndrome Coronavirus Spike Protein during Entry, Journal of Virology, 80(3):1302-1310 (2006).
Garrone, P. et al., A Prime-Boost Strategy Using Virus-Like Particles Pseudotyped for HCV Proteins Triggers Broadly Neutralizing Antibodies in Macaques, Sci. Transl. Med., 3(94):94ra71 1-8 (2011).
Garry, C.E. and Garry, R.F., Proteomics computational analyses suggest that baculovirus GP64 superfamily proteins are class III penetrenes, Virology Journal 5(28): 1-11 (2008).
GenBank Accession No. ACM48044.1, envelope glycoprotein B [Human betaherpesvirus 5], published on Dec. 17, 2009), retrieved from <<http://www.ncbi.nlm.nih.gov/protein/222354496>>, accessed on Oct. 2, 2018.
GenBank Accession No. ACM48061.1, tegument protein pp65 [Human herpesvirus 5], Sep. 17, 2009.
GenBank Accession No. ADX53329.1, G protein precursor [Vesicular stomatitis Indiana virus], published on Jun. 21, 2011, retrieved from <<https://www.ncbi.nlm.nih.gov/protein/ADX53329>>, accessed on Oct. 2, 2018.
Gonczol, E. and Plotkin, S., Development of a cytomegalovirus vaccine: lessons from recent clinical trials, Expert Opinion on Biological Therapy, 1(3): 401-412 (2001).
International Search Report for PCT/IB2012/002854, 6 pages (Apr. 15, 2013).
Kirchmeier, M. et al., Enveloped virus-like particle expression of human Cytomegalovirus Glycoprotein B Antigen induces antibodies with potent and broad neutralizing activity, Clinical and Vaccine Immunology, 21(2): 174-180 (2014).
Lagging, L.M. et al., Functional Role of Hepatitis C Virus Chimeric Glycoproteins in the Infectivity of Pseudotyped Virus, Journal of Virology, 72(5): 3539-3546 (1998).
Sampson, J. H et al., Brain immunology and immunotherapy in brain tumours, Nat Rev Cancer, 20(1):12-25 (2020).
UniProtKB/Swiss-Prot: B9VXM1 (2009) HCMV sequence.
UniProtKB/Swiss-Prot: B9VXM4 (2009) HCMV sequence.
UniProtKB/Swiss-Prot: B9VXP1 (2009) HCMV sequence.
UniProtKB/Swiss-Prot: P03332 (1986) MLV gag.
UniProtKB/Swiss-Prot: Q86131 (1996) VSV-G.
Written Opinion for PCT/IB2012/002854, 10 pages (Apr. 15, 2013).

* cited by examiner

SEQUENCE LISTING

```
<160> NUMBER OF SEQ ID NOS: 22

<210> SEQ ID NO 1
<211> LENGTH: 538
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag Amino Acid Sequence

<400> SEQUENCE: 1

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110
```

```
Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Pro Leu Ile Asp Leu Leu Thr Glu
145                 150                 155                 160

Asp Pro Pro Pro Tyr Arg Asp Pro Arg Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Glu Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Asp Leu Tyr Asn Trp Lys Asn
225                 230                 235                 240

Asn Asn Pro Ser Phe Ser Glu Asp Pro Gly Lys Leu Thr Ala Leu Ile
            245                 250                 255

Glu Ser Val Leu Ile Thr His Gln Pro Thr Trp Asp Asp Cys Gln Gln
        260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
        290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
            325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
        370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
            405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
        435                 440                 445

Glu Glu Lys Glu Glu Arg Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
            485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
        515                 520                 525
```

Pro Gln Thr Ser Leu Leu Thr Leu Asp Asp
    530                 535

<210> SEQ ID NO 2
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag Nucleotide Sequence

<400> SEQUENCE: 2

| | | | | | |
|---|---|---|---|---|---|
| atgggccaga | ctgttaccac | tcccttaagt | ttgaccttag | gtcactggaa | agatgtcgag | 60 |
| cggatcgctc | acaaccagtc | ggtagatgtc | aagaagagac | gttgggttac | cttctgctct | 120 |
| gcagaatggc | caacctttaa | cgtcggatgg | ccgcgagacg | gcacctttaa | ccgagacctc | 180 |
| atcacccagg | ttaagatcaa | ggtctttttca | cctggcccgc | atggacaccc | agaccaggtc | 240 |
| ccctacatcg | tgacctggga | agccttggct | tttgaccccc | ctccctgggt | caagcccttt | 300 |
| gtacaccctà | agcctccgcc | tcctcttcct | ccatccgccc | cgtctctccc | ccttgaacct | 360 |
| cctcgttcga | ccccgcctcg | atcctcccttt | tatccagccc | tcactccttc | tctaggcgcc | 420 |
| aaacctaaac | ctcaagttct | ttctgacagt | gggggggccgc | tcatcgacct | acttacagaa | 480 |
| gaccccccgc | cttataggga | cccaagacca | cccccttccg | acaggacgg | aaatggtgga | 540 |
| gaagcgaccc | ctgcgggaga | ggcaccggac | ccctcccccaa | tggcatctcg | cctacgtggg | 600 |
| agacgggagc | cccctgtggc | cgactccact | acctcgcagg | cattcccccct | ccgcgcagga | 660 |
| ggaaacggac | agcttcaata | ctggccgttc | tcctcttctg | acctttacaa | ctggaaaaat | 720 |
| aataaccctt | cttttttctga | agatccaggt | aaactgacag | ctctgatcga | gtctgttctc | 780 |
| atcacccatc | agcccacctg | ggacgactgt | cagcagctgt | tggggactct | gctgaccgga | 840 |
| gaagaaaaac | aacgggtgct | cttagaggct | agaaaggcgg | tgcggggcga | tgatgggcgc | 900 |
| cccactcaac | tgcccaatga | agtcgatgcc | gcttttcccc | tcgagcgccc | agactgggat | 960 |
| tacaccaccc | aggcaggtag | gaaccaccta | gtccactatc | gccagttgct | cctagcgggt | 1020 |
| ctccaaaacg | cgggcagaag | ccccaccaat | ttggccaagg | taaaaggaat | aacacaaggg | 1080 |
| cccaatgagt | ctccctcggc | cttcctagag | agacttaagg | aagcctatcg | caggtacact | 1140 |
| ccttatgacc | ctgaggaccc | agggcaagaa | actaatgtgt | ctatgtcttt | catttggcag | 1200 |
| tctgccccag | acattgggag | aaagttagag | aggttagaag | atttaaaaaa | caagacgctt | 1260 |
| ggagatttgg | ttagagaggc | agaaaagatc | tttaataaac | gagaaccccc | ggaagaagaa | 1320 |
| gaggaacgta | tcaggagaga | aacagaggaa | aagaagaac | gccgtaggac | agaggatgag | 1380 |
| cagaaagaga | agaaaagaga | tcgtaggaga | catagagaga | tgagcaagct | attggccact | 1440 |
| gtcgttagtg | gacagaaaca | ggatagacag | ggaggagaac | gaaggaggtc | ccaactcgat | 1500 |
| cgcgaccagt | gtgcctactg | caaagaaaag | gggcactggg | ctaaagattg | tcccaagaaa | 1560 |
| ccacgaggac | ctcggggacc | aagaccccag | acctccctcc | tgaccctaga | tgac | 1614 |

<210> SEQ ID NO 3
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence

<400> SEQUENCE: 3

```
atgggacaga cagtcactac acccctgagc ctgacactgg gacattggaa agacgtggag      60
aggattgcac ataaccagag cgtggacgtg aagaaacgga gatgggtcac cttttgctcc     120
gccgagtggc caacattcaa tgtgggatgg ccccgagatg gcaccttcaa ccgggacctg     180
atcactcagg tgaagatcaa ggtcttctct ccaggacccc acggccatcc agatcaggtg     240
ccctacatcg tcacctggga ggctctggca tttgaccccc ctccatgggt gaagcctttc     300
gtccacccaa aaccacctcc accactgcct ccatctgccc ctagtctgcc actggaaccc     360
cctcggtcaa ccccacccag aagctccctg tatcccgcac tgacacctag cctgggggcc     420
aagcctaaac acaggtgct gtctgatagt ggcgggcctc tgatcgatct gctgaccgag     480
gaccctccac cataccgcga cccacgacct ccaccaagcg accgggacgg aaacggagga     540
gaggctacac ccgcaggcga agccccgat cctagtccaa tggcatcaag gctgcgcggg     600
aggcgcgaac ctccagtggc cgactcaacc acaagccagg catttccact gagggccggg     660
ggaaatggac agctccagta ttggcccttc tctagttcag atctgtacaa ctggaagaac     720
aataacccta gcttcagcga ggacccaggc aaactgaccg ccctgatcga atccgtgctg     780
attacccacc agcccacatg ggacgattgt cagcagctcc tgggcaccct gctgaccgga     840
gaggaaaagc agagagtgct gctggaggct aggaaagcag tccgcgggga cgatggaagg     900
ccaacacagc tccccaatga ggtggatgcc gctttccctc tggaacggcc agattgggac     960
tatactaccc aggctggacg caaccacctg gtgcattacc ggcagctcct gctggctgga    1020
ctgcagaatg cagggcgcag ccccactaac ctggccaagg tgaaaggaat cacccagggc    1080
cccaatgagt ccccttctgc attcctggag cggctgaagg aagcctaccg acggtatact    1140
ccctacgatc ctgaggaccc aggccaggaa accaacgtga gtatgagctt catctggcag    1200
tccgctcctg acattggccg aaaactggag cggctggaag atctgaagaa caagaccctg    1260
ggcgacctgg tgcgggaggc agaaaagatc ttcaacaaaa gggagactcc agaggaacgg    1320
gaggaaagaa ttagaaggga acagaggaa aggaggaac gccgacggac tgaggatgaa    1380
cagaaggaga agaaagaga ccggcggcgg caccggagga tgtctaagct gctggccacc    1440
gtggtcagtg ccagaaaaca ggatcgacag ggaggagagc gacggagaag ccagctcgat    1500
cgggaccagt gcgcctattg taaggaaaaa gggcattggg ctaaggactg ccccaagaaa    1560
cccagaggcc cacgcgggcc ccgacctcag acttccctgc tgaccctgga cgat          1614
```

<210> SEQ ID NO 4
<211> LENGTH: 1099
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag amino acid sequence
<220> FEATURE:
<221> NAME/KEY: MISC_FEATURE
<222> LOCATION: (539)..(1099)
<223> OTHER INFORMATION: CMV pp65 amino acid sequence

<400> SEQUENCE: 4

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
```

```
                35                  40                  45
Gly Trp Pro Arg Asp Gly Thr Phe Asn Arg Asp Leu Ile Thr Gln Val
 50                  55                  60
Lys Ile Lys Val Phe Ser Pro Gly His Gly His Pro Asp Gln Val
 65                  70                  75                  80
Pro Tyr Ile Val Thr Trp Glu Ala Leu Ala Phe Asp Pro Pro Trp
                 85                  90                  95
Val Lys Pro Phe Val His Pro Lys Pro Pro Pro Leu Pro Pro Ser
                100                 105                 110
Ala Pro Ser Leu Pro Leu Glu Pro Arg Ser Thr Pro Arg Ser
                115                 120                 125
Ser Leu Tyr Pro Ala Leu Thr Pro Ser Leu Gly Ala Lys Pro Lys Pro
    130                 135                 140
Gln Val Leu Ser Asp Ser Gly Pro Leu Ile Asp Leu Leu Thr Glu
145                 150                 155                 160
Asp Pro Pro Pro Tyr Arg Asp Pro Arg Pro Pro Ser Asp Arg Asp
                165                 170                 175
Gly Asn Gly Gly Glu Ala Thr Pro Ala Gly Glu Ala Pro Asp Pro Ser
                180                 185                 190
Pro Met Ala Ser Arg Leu Arg Gly Arg Glu Pro Pro Val Ala Asp
                195                 200                 205
Ser Thr Thr Ser Gln Ala Phe Pro Leu Arg Ala Gly Gly Asn Gly Gln
    210                 215                 220
Leu Gln Tyr Trp Pro Phe Ser Ser Ser Asp Leu Tyr Asn Trp Lys Asn
225                 230                 235                 240
Asn Asn Pro Ser Phe Ser Glu Asp Pro Gly Lys Leu Thr Ala Leu Ile
                245                 250                 255
Glu Ser Val Leu Ile Thr His Gln Pro Thr Trp Asp Asp Cys Gln Gln
                260                 265                 270
Leu Leu Gly Thr Leu Leu Thr Gly Glu Glu Lys Gln Arg Val Leu Leu
                275                 280                 285
Glu Ala Arg Lys Ala Val Arg Gly Asp Asp Gly Arg Pro Thr Gln Leu
    290                 295                 300
Pro Asn Glu Val Asp Ala Ala Phe Pro Leu Glu Arg Pro Asp Trp Asp
305                 310                 315                 320
Tyr Thr Thr Gln Ala Gly Arg Asn His Leu Val His Tyr Arg Gln Leu
                325                 330                 335
Leu Leu Ala Gly Leu Gln Asn Ala Gly Arg Ser Pro Thr Asn Leu Ala
                340                 345                 350
Lys Val Lys Gly Ile Thr Gln Gly Pro Asn Glu Ser Pro Ser Ala Phe
                355                 360                 365
Leu Glu Arg Leu Lys Glu Ala Tyr Arg Arg Tyr Thr Pro Tyr Asp Pro
    370                 375                 380
Glu Asp Pro Gly Gln Glu Thr Asn Val Ser Met Ser Phe Ile Trp Gln
385                 390                 395                 400
Ser Ala Pro Asp Ile Gly Arg Lys Leu Glu Arg Leu Glu Asp Leu Lys
                405                 410                 415
Asn Lys Thr Leu Gly Asp Leu Val Arg Glu Ala Glu Lys Ile Phe Asn
                420                 425                 430
Lys Arg Glu Thr Pro Glu Glu Arg Glu Arg Ile Arg Arg Glu Thr
                435                 440                 445
Glu Glu Lys Glu Glu Arg Arg Thr Glu Asp Glu Gln Lys Glu Lys
    450                 455                 460
```

```
Glu Arg Asp Arg Arg His Arg Glu Met Ser Lys Leu Leu Ala Thr
465                 470                 475                 480

Val Val Ser Gly Gln Lys Gln Asp Arg Gln Gly Gly Glu Arg Arg
            485                 490                 495

Ser Gln Leu Asp Arg Asp Gln Cys Ala Tyr Cys Lys Glu Lys Gly His
        500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Cys Glu Ser Arg Gly Arg
        530                 535                 540

Arg Cys Pro Glu Met Ile Ser Val Leu Gly Pro Ile Ser Gly His Val
545                 550                 555                 560

Leu Lys Ala Val Phe Ser Arg Gly Asp Thr Pro Val Leu Pro His Glu
                565                 570                 575

Thr Arg Leu Leu Gln Thr Gly Ile His Val Arg Val Ser Gln Pro Ser
            580                 585                 590

Leu Ile Leu Val Ser Gln Tyr Thr Pro Asp Ser Thr Pro Cys His Arg
        595                 600                 605

Gly Asp Asn Gln Leu Gln Val Gln His Thr Tyr Phe Thr Gly Ser Glu
    610                 615                 620

Val Glu Asn Val Ser Val Asn Val His Asn Pro Thr Gly Arg Ser Ile
625                 630                 635                 640

Cys Pro Ser Gln Glu Pro Met Ser Ile Tyr Val Tyr Ala Leu Pro Leu
                645                 650                 655

Lys Met Leu Asn Ile Pro Ser Ile Asn Val His His Tyr Pro Ser Ala
            660                 665                 670

Ala Glu Arg Lys His Arg His Leu Pro Val Ala Asp Ala Val Ile His
        675                 680                 685

Ala Ser Gly Lys Gln Met Trp Gln Ala Arg Leu Thr Val Ser Gly Leu
    690                 695                 700

Ala Trp Thr Arg Gln Gln Asn Gln Trp Lys Glu Pro Asp Val Tyr Tyr
705                 710                 715                 720

Thr Ser Ala Phe Val Phe Pro Thr Lys Asp Val Ala Leu Arg His Val
                725                 730                 735

Val Cys Ala His Glu Leu Val Cys Ser Met Glu Asn Thr Arg Ala Thr
            740                 745                 750

Lys Met Gln Val Ile Gly Asp Gln Tyr Val Lys Val Tyr Leu Glu Ser
        755                 760                 765

Phe Cys Glu Asp Val Pro Ser Gly Lys Leu Phe Met His Val Thr Leu
    770                 775                 780

Gly Ser Asp Val Glu Glu Asp Leu Thr Met Thr Arg Asn Pro Gln Pro
785                 790                 795                 800

Phe Met Arg Pro His Glu Arg Asn Gly Phe Thr Val Leu Cys Pro Lys
                805                 810                 815

Asn Met Ile Ile Lys Pro Gly Lys Ile Ser His Ile Met Leu Asp Val
            820                 825                 830

Ala Phe Thr Ser His Glu His Phe Gly Leu Leu Cys Pro Lys Ser Ile
        835                 840                 845

Pro Gly Leu Ser Ile Ser Gly Asn Leu Leu Met Asn Gly Gln Gln Ile
    850                 855                 860

Phe Leu Glu Val Gln Ala Ile Arg Glu Thr Val Glu Leu Arg Gln Tyr
865                 870                 875                 880
```

Asp Pro Val Ala Ala Leu Phe Phe Phe Asp Ile Asp Leu Leu Gln
                885                 890                 895

Arg Gly Pro Gln Tyr Ser Glu His Pro Thr Phe Thr Ser Gln Tyr Arg
            900                 905                 910

Ile Gln Gly Lys Leu Glu Tyr Arg His Thr Trp Asp Arg His Asp Glu
            915                 920                 925

Gly Ala Ala Gln Gly Asp Asp Val Trp Thr Ser Gly Ser Asp Ser
        930                 935                 940

Asp Glu Glu Leu Val Thr Thr Glu Arg Lys Thr Pro Arg Val Thr Gly
945                 950                 955                 960

Gly Gly Ala Met Ala Gly Ala Ser Thr Ser Ala Gly Arg Lys Arg Lys
                965                 970                 975

Ser Ala Ser Ser Ala Thr Ala Cys Thr Ala Gly Val Met Thr Arg Gly
                980                 985                 990

Arg Leu Lys Ala Glu Ser Thr Val Ala Pro Glu Glu Asp Thr Asp Glu
            995                 1000                1005

Asp Ser Asp Asn Glu Ile His Asn Pro Ala Val Phe Thr Trp Pro
    1010                1015                1020

Pro Trp Gln Ala Gly Ile Leu Ala Arg Asn Leu Val Pro Met Val
    1025                1030                1035

Ala Thr Val Gln Gly Gln Asn Leu Lys Tyr Gln Glu Phe Phe Trp
    1040                1045                1050

Asp Ala Asn Asp Ile Tyr Arg Ile Phe Ala Glu Leu Glu Gly Val
    1055                1060                1065

Trp Gln Pro Ala Ala Gln Pro Lys Arg Arg Arg His Arg Gln Asp
    1070                1075                1080

Ala Leu Pro Gly Pro Cys Ile Ala Ser Thr Pro Lys Lys His Arg
    1085                1090                1095

Gly

<210> SEQ ID NO 5
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag nucleotide sequence
<220> FEATURE:
<221> NAME/KEY: misc_feature
<222> LOCATION: (1615)..(3300)
<223> OTHER INFORMATION: CMV pp65 nucleotide sequence

<400> SEQUENCE: 5
atgggccaga ctgttaccac tcccttaagt ttgaccttag gtcactggaa agatgtcgag     60
cggatcgctc acaaccagtc ggtagatgtc aagaagagac gttgggttac cttctgctct    120
gcagaatggc caacctttaa cgtcggatgg cgcgagacg gcacctttaa ccgagacctc    180
atcacccagg ttaagatcaa ggtctttca cctggcccgc atggacaccc agaccaggtc    240
ccctacatcg tgacctggga agccttggct tttgaccccc tccctgggt caagcccttt    300 gtacacccta gcctccgcc tcctcttcct ccatccgccc cgtctctccc ccttgaacct    360
cctcgttcga ccccgcctcg atcctccctt tatccagccc tcactccttc tctaggcgcc    420
aaacctaaac ctcaagttct ttctgacagt gggggccgc tcatcgacct acttacagaa    480
gaccccccgc ttataggga cccaagacca ccccttccg acaggacgg aaatggtgga    540 gaagcgaccc ctgcgggaga ggcaccggac ccctcccaa tggcatctcg cctacgtggg    600

| | |
|---|---|
| agacgggagc cccctgtggc cgactccact acctcgcagg cattcccct ccgcgcagga | 660 |
| ggaaacggac agcttcaata ctggccgttc tcctcttctg acctttacaa ctggaaaaat | 720 |
| aataacccctt cttttttctga agatccaggt aaactgacag ctctgatcga gtctgttctc | 780 |
| atcacccatc agcccacctg gacgactgt cagcagctgt tggggactct gctgaccgga | 840 |
| gaagaaaaac aacgggtgct cttagaggct agaaaggcgg tgcggggcga tgatgggcgc | 900 |
| cccactcaac tgcccaatga agtcgatgcc gcttttcccc tcgagcgccc agactgggat | 960 |
| tacaccaccc aggcaggtag gaaccaccta gtccactatc gccagttgct cctagcgggt | 1020 |
| ctccaaaacg cgggcagaag ccccaccaat ttggccaagg taaaaggaat aacacaaggg | 1080 |
| cccaatgagt ctccctcggc cttcctagag agacttaagg aagcctatcg caggtacact | 1140 |
| ccttatgacc ctgaggaccc agggcaagaa actaatgtgt ctatgtcttt catttggcag | 1200 |
| tctgccccag acattgggag aaagttagag aggttagaag atttaaaaaa caagacgctt | 1260 |
| ggagatttgg ttagagaggc agaaaagatc tttaataaac gagaaacccc ggaagaaaga | 1320 |
| gaggaacgta tcaggagaga aacagaggaa aaagaagaac gccgtaggac agaggatgag | 1380 |
| cagaaagaga aagaaagaga tcgtaggaga catagagaga tgagcaagct attggccact | 1440 |
| gtcgttagtg gacagaaaca ggatagacag ggaggagaac gaaggaggtc ccaactcgat | 1500 |
| cgcgaccagt gtgcctactg caaagaaaag gggcactggg ctaaagattg tccaagaaa | 1560 |
| ccacgaggac ctcggggacc aagaccccag acctccctcc tgaccctaga tgactgtgag | 1620 |
| tcgcgcggtc gccgttgtcc cgaaatgata tccgtactgg gtcccatttc ggggcacgtg | 1680 |
| ctgaaagccg tgtttagtcg cggcgacacg ccggtgctgc cgcacgagac gcgactcctg | 1740 |
| cagacgggta tccacgtgcg cgtgagccag ccctcgctga tcctggtgtc gcagtacacg | 1800 |
| cccgactcga cgccatgcca ccgcggcgac aatcagctgc aggtgcagca cacgtacttt | 1860 |
| acgggcagcg aggtggagaa cgtgtcggtc aacgtgcaca ccccacgggg ccggagcatc | 1920 |
| tgccccagcc aagagcccat gtcgatctat gtgtacgcgc tgccgctcaa gatgctgaac | 1980 |
| atccccagca tcaacgtgca ccactacccg tcggcggccg agcgcaaaca ccgacacctg | 2040 |
| cccgtagctg acgctgtgat tcacgcgtcg ggcaagcaga tgtggcaggc gcgtctcacg | 2100 |
| gtctcgggac tggcctggac gcgtcagcag aaccagtgga aagagcccga cgtctactac | 2160 |
| acgtcagcgt tcgtgtttcc caccaaggac gtggcactgc ggcacgtggt gtgcgcgcac | 2220 |
| gagctggttt gctccatgga gaacacgcgc gcaaccaaga tgcaggtgat aggtgaccag | 2280 |
| tacgtcaagg tgtacctgga gtccttctgc gaggacgtgc cctccggcaa gctctttatg | 2340 |
| cacgtcacgc tgggctctga cgtggaagag gacctgacga tgacccgcaa cccgcaaccc | 2400 |
| ttcatgcgcc cccacgagcg caacggcttt acggtgttgt gtcccaaaaa tatgataatc | 2460 |
| aaaccgggca agatctcgca catcatgctg gatgtggctt ttacctcaca cgagcatttt | 2520 |
| gggctgctgt gtcccaagag catccccggc ctgagcatct caggtaacct attgatgaac | 2580 |
| gggcagcaga tcttcctgga ggtgcaagcg atacgcgaga ccgtggaact gcgtcagtac | 2640 |
| gatcccgtgg ctgcgctctt cttttttcgat atcgacttgc tgctgcagcg cgggcctcag | 2700 |
| tacagcgaac accccacctt caccagccag tatcgcatcc agggcaagct tgagtaccga | 2760 |
| cacacctggg accggcacga cgagggtgcc gcccagggcg acgacgacgt ctggaccagc | 2820 |
| ggatcggact ccgacgagga actcgtaacc accgagcgca agacgccccg cgttaccggc | 2880 |
| ggcggcgcca tggcgggcgc ctcccacttcc gcgggccgca aacgcaaatc agcatcctcg | 2940 |

-continued

```
gcgacggcgt gcacggcggg cgttatgaca cgcggccgcc ttaaggccga gtccaccgtc   3000
gcgcccgaag aggacaccga cgaggattcc gacaacgaaa tccacaatcc ggccgtgttc   3060
acctggccgc cctggcaggc cggcatcctg gcccgcaacc tggtgcccat ggtggctacg   3120
gttcagggtc agaatctgaa gtaccaggag ttcttctggg acgccaacga catctaccgc   3180
atcttcgccg aattggaagg cgtatggcag cccgctgcgc aacccaaacg tcgccgccac   3240
cggcaagacg ccttgcccgg gccatgcatc gcctcgacgc ccaaaaagca ccgaggttag   3300
```

<210> SEQ ID NO 6
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65 nucleotide sequence

<400> SEQUENCE: 6

```
atgggacaga cagtcactac acccctgagc ctgacactgg acattggaa agacgtggag     60
aggattgcac ataaccagag cgtggacgtg aagaaacgga gatgggtcac cttttgctcc   120
gccgagtggc aacattcaa tgtgggatgg ccccgagatg caccttcaa ccgggacctg    180
atcactcagg tgaagatcaa ggtcttctct ccaggacccc acggccatcc agatcaggtg   240
ccctacatcg tcacctggga ggctctggca tttgaccccc ctccatgggt gaagcctttc   300
gtccacccaa aaccacctcc accactgcct ccatctgccc ctagtctgcc actggaaccc   360
cctcggtcaa ccccacccag aagctccctg tatcccgcac tgacacctag cctgggggcc   420
aagcctaaac acaggtgct gtctgatagt ggcgggcctc tgatcgatct gctgaccgag   480
gaccctccac catacgcga cccacgacct ccaccaagcg accgggacgg aaacggagga   540
gaggctacac ccgcaggcga agcccccgat cctagtccaa tggcatcaag gctgcgcggg   600
aggcgcgaac ctccagtggc cgactcaacc acaagccagg catttccact gagggccggg   660
ggaaatggac agctccagta ttggcccttc tctagttcag atctgtacaa ctggaagaac   720
aataacccta gcttcagcga ggaccccagc aaactgaccg ccctgatcga atccgtgctg   780
attacccacc agcccacatg ggacgattgt cagcagctcc tgggcaccct gctgaccgga   840
gaggaaaagc agagagtgct gctggaggct aggaaagcag tccgcgggga cgatggaagg   900
ccaacacagc tccccaatga ggtggatgcc gctttccctc tggaacggcc agattgggac   960
tatactaccc aggctggacg caaccacctg gtgcattacc ggcagctcct gctggctgga  1020
ctgcagaatg cagggcgcag ccccactaac ctggccaagg tgaaaggaat cacccagggc  1080
cccaatgagt cccccttctg cattcctgag cggctgaagg aagcctaccg acggtatact  1140
ccctacgatc ctgaggaccc aggccaggaa accaacgtga gtatgagctt catctggcag  1200
tccgctcctg acattggccg aaaactggag cggctggaag atctgaagaa caagaccctg  1260
ggcgacctgg tgcgggaggc agaaaagatc ttcaacaaaa gggagactcc agaggaacgg  1320
gaggaaagaa ttagaaggga acagaggaa aggaggaac gccgacggac tgaggatgaa  1380
cagaaggaga agaaaagaga ccggcggcgg caccgggaga tgtctaagct gctggccacc  1440
gtggtcagtg ccagaaaaca ggatcgcacg ggaggagagc gacggagaag ccagctcgat  1500
cgggaccagt gcgcctattg taaggaaaaa gggcattggg ctaaggactg ccccaagaaa  1560
```

-continued

```
cccagaggcc cacgcgggcc ccgacctcag acttccctgc tgaccctgga cgattgcgag    1620
agccggggcc ggcggtgccc agaaatgatc tctgtgctgg ggcccattag tggacatgtg    1680
ctgaaggccg tcttctccag gggagacacc cccgtgctgc ctcacgagac tcgactgctg    1740
cagaccggca tccatgtgcg ggtctcccag ccctctctga ttctggtgtc acagtataca    1800
ccagatagca ctccctgcca cagaggagac aatcagctcc aggtgcagca tacctacttt    1860
acaggctccg aggtcgaaaa cgtgtctgtc aatgtgcaca accctaccgg caggagcatc    1920
tgtcctagcc aggagccaat gagcatctac gtgtacgccc tgcctctgaa gatgctgaat    1980
atcccatcaa ttaacgtcca ccattaccct agcgcagccg aacggaagca cagacatctg    2040
ccagtggccg acgctgtcat ccatgccagc ggcaaacaga tgtggcaggc aagactgacc    2100
gtgtccgggc tggcctggac aaggcagcag aatcagtgga aggagcccga cgtgtactat    2160
accagcgcct tcgtgttccc taccaaagac gtggccctga catgtggt gtgcgcacat    2220
gagctggtgt gcagcatgga aaacactagg gccaccaaga tgcaggtcat cggcgatcag    2280
tatgtcaaag tgtacctgga gagtttttgc gaagacgtgc atcagggaa gctgttcatg    2340
catgtgaccc tgggcagcga tgtcgaggaa gacctgacca tgacaagaaa tccacagccc    2400
tttatgagac cccacgagag gaatgggttc actgtgctgt gccccaagaa catgatcatt    2460
aagcctggaa aaatcagtca tattatgctg gatgtggcct ttacatcaca cgagcatttc    2520
ggactgctgt gccccaaatc catccctgga ctgagcattt ccggcaatct gctgatgaac    2580
ggccagcaga tcttcctgga agtgcaggcc atccgggaga ccgtcgaact gcgacagtat    2640
gacccagtgg ctgcactgtt ctttttcgac atcgacctgc tgctgcagcg aggaccacag    2700
tacagcgagc ccctactttt tacctcccag tatcggattc aggggaagct ggagtacagg    2760
cacacctggg atcgccatga cgaaggagcc gctcagggg acgatgacgt gtggacatct    2820
ggcagtgatt cagacgagga actggtgaca actgagcgaa aaaccccccg ggtgacagga    2880
ggagggcaa tggcaggggc cagcaccagc gcagggcgga agcgaaaaag cgccagcagc    2940
gccacagcat gtaccgccgg cgtgatgact agaggaaggc tgaaggccga gtctacagtc    3000
gctcccgagg aagatactga cgaggatagt gacaatgaaa tccacaaccc cgccgtgttc    3060
acctggccac cttggcaggc agggattctg gctcgcaacc tggtccccat ggtggcaacc    3120
gtccagggac agaatctgaa gtatcaggag ttttctggg atgctaacga catctaccgg    3180
attttttgcag agctggaagg cgtgtggcag ccagcagccc agcccaaacg acggagacat    3240
cgacaggacg ctctgccagg accttgtatc gccagcacac caaagaagca caggggctaa    3300
```

<210> SEQ ID NO 7
<211> LENGTH: 907
<212> TYPE: PRT
<213> ORGANISM: Human cytomegalovirus
<220> FEATURE:
<221> NAME/KEY: MISC_FEATURE
<222> LOCATION: (1)..(907)
<223> OTHER INFORMATION: HCMV gB Amino Acid Sequence
<220> FEATURE:
<221> NAME/KEY: MISC_FEATURE
<222> LOCATION: (751)..(907)
<223> OTHER INFORMATION: TM and CD

<400> SEQUENCE: 7

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
```

```
                    20                  25                  30
        Ala Thr His Ser His His Ser Ser His Thr Thr Ser Ala Ala His Ser
                35                  40                  45
        Arg Ser Gly Ser Val Ser Gln Arg Val Thr Ser Ser Gln Thr Val Ser
                50                  55                  60
        His Gly Val Asn Glu Thr Ile Tyr Asn Thr Thr Leu Lys Tyr Gly Asp
        65                  70                  75                  80
        Val Val Gly Val Asn Thr Thr Lys Tyr Pro Tyr Arg Val Cys Ser Met
                        85                  90                  95
        Ala Gln Gly Thr Asp Leu Ile Arg Phe Glu Arg Asn Ile Val Cys Thr
                        100                 105                 110
        Ser Met Lys Pro Ile Asn Glu Asp Leu Asp Glu Gly Ile Met Val Val
                        115                 120                 125
        Tyr Lys Arg Asn Ile Val Ala His Thr Phe Lys Val Arg Val Tyr Gln
                130                 135                 140
        Lys Val Leu Thr Phe Arg Arg Ser Tyr Ala Tyr Ile His Thr Thr Tyr
        145                 150                 155                 160
        Leu Leu Gly Ser Asn Thr Glu Tyr Val Ala Pro Pro Met Trp Glu Ile
                        165                 170                 175
        His His Ile Asn Ser His Ser Gln Cys Tyr Ser Ser Tyr Ser Arg Val
                        180                 185                 190
        Ile Ala Gly Thr Val Phe Val Ala Tyr His Arg Asp Ser Tyr Glu Asn
                        195                 200                 205
        Lys Thr Met Gln Leu Met Pro Asp Asp Tyr Ser Asn Thr His Ser Thr
                        210                 215                 220
        Arg Tyr Val Thr Val Lys Asp Gln Trp His Ser Arg Gly Ser Thr Trp
        225                 230                 235                 240
        Leu Tyr Arg Glu Thr Cys Asn Leu Asn Cys Met Val Thr Ile Thr Thr
                        245                 250                 255
        Ala Arg Ser Lys Tyr Pro Tyr His Phe Phe Ala Thr Ser Thr Gly Asp
                        260                 265                 270
        Val Val Asp Ile Ser Pro Phe Tyr Asn Gly Thr Asn Arg Asn Ala Ser
                        275                 280                 285
        Tyr Phe Gly Glu Asn Ala Asp Lys Phe Phe Ile Phe Pro Asn Tyr Thr
                        290                 295                 300
        Ile Val Ser Asp Phe Gly Arg Pro Asn Ser Ala Leu Glu Thr His Arg
        305                 310                 315                 320
        Leu Val Ala Phe Leu Glu Arg Ala Asp Ser Val Ile Ser Trp Asp Ile
                        325                 330                 335
        Gln Asp Glu Lys Asn Val Thr Cys Gln Leu Thr Phe Trp Glu Ala Ser
                        340                 345                 350
        Glu Arg Thr Ile Arg Ser Glu Ala Glu Asp Ser Tyr His Phe Ser Ser
                        355                 360                 365
        Ala Lys Met Thr Ala Thr Phe Leu Ser Lys Lys Gln Glu Val Asn Met
                        370                 375                 380
        Ser Asp Ser Ala Leu Asp Cys Val Arg Asp Glu Ala Ile Asn Lys Leu
        385                 390                 395                 400
        Gln Gln Ile Phe Asn Thr Ser Tyr Asn Gln Thr Tyr Glu Lys Tyr Gly
                        405                 410                 415
        Asn Val Ser Val Phe Glu Thr Thr Gly Gly Leu Val Val Phe Trp Gln
                        420                 425                 430
        Gly Ile Lys Gln Lys Ser Leu Val Glu Leu Glu Arg Leu Ala Asn Arg
                        435                 440                 445
```

```
Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                    485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ile Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Val Ile Ile Ile
            755                 760                 765

Tyr Leu Ile Tyr Thr Arg Gln Arg Arg Leu Cys Met Gln Pro Leu Gln
    770                 775                 780

Asn Leu Phe Pro Tyr Leu Val Ser Ala Asp Gly Thr Thr Val Thr Ser
785                 790                 795                 800

Gly Asn Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
                820                 825                 830

Ala Ser Thr Ala Ala Pro Pro Tyr Thr Asn Glu Gln Ala Tyr Gln Met
            835                 840                 845

Leu Leu Ala Leu Val Arg Leu Asp Ala Glu Gln Arg Ala Gln Gln Asn
    850                 855                 860
```

| | | | | | | | | | | | | |
|---|---|---|---|---|---|---|---|---|---|---|---|---|
|Gly|Thr|Asp|Ser|Leu|Asp|Gly|Gln|Thr|Gly|Thr|Gln|Asp|Lys|Gly|Gln|
|865| | | | |870| | | | |875| | | | |880|

| | | | | | | | | | | | |
|---|---|---|---|---|---|---|---|---|---|---|---|
|Lys|Pro|Asn|Leu|Leu|Asp|Arg|Leu|Arg|His|Arg|Lys|Asn|Gly|Tyr|Arg|
| | | | |885| | | | |890| | | | |895| |

| | | | | | | | | | |
|---|---|---|---|---|---|---|---|---|---|
|His|Leu|Lys|Asp|Ser|Asp|Glu|Glu|Glu|Asn|Val|
| | |900| | | | |905| | | |

<210> SEQ ID NO 8
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 8

| | |
|---|---|
|atggaatcca ggatctggtg cctggtagtc tgcgttaact tgtgtatcgt ctgtctgggt|60|
|gctgcggttt cctcatcttc tactcgtgga acttctgcta ctcacagtca ccattcctct|120|
|catacgacgt ctgctgctca ttctcgatcc ggttcagtct ctcaacgcgt aacttcttcc|180|
|caaacggtca gccatggtgt taacgagacc atctacaaca ctaccctcaa gtacggagat|240|
|gtggtggggg tcaacaccac caagtacccc atcgcgtgt gttctatggc acagggtacg|300|
|gatcttattc gctttgaacg taatatcgtc tgcacctcga tgaagcccat caatgaagac|360|
|ctggacgagg gcatcatggt ggtctacaaa cgcaacatcg tcgcgcacac ctttaaggta|420|
|cgagtctacc agaaggtttt gacgtttcgt cgtagctacg cttacatcca ccaccacttat|480|
|ctgctgggca gcaacacgga atacgtggcg cctcctatgt gggagattca tcatatcaac|540|
|agtcacagtc agtgctacag ttcctacagc cgcgttatag caggcacggt tttcgtggct|600|
|tatcataggg acagctatga aaacaaaacc atgcaattaa tgcccgacga ttattccaac|660|
|acccacagta cccgttacgt gacggtcaag gatcaatggc acagccgcgg cagcaccctgg|720|
|ctctatcgtg agacctgtaa tctgaattgt atggtgacca tcactactgc gcgctccaag|780|
|tatcccctatc attttttcgc aacttccacg ggtgatgtgg ttgacatttc tccttctac|840|
|aacggaacta atcgcaatgc cagctatttt ggagaaaacg ccgacaagtt tttcattttt|900|
|ccgaactaca ctatcgtctc cgactttgga agaccgaatt ctgcgttaga cccacagg|960|
|ttggtggctt ttcttgaacg tgcggactca gtgatctcct gggatataca ggacgagaag|1020|
|aatgttactt gtcaactcac tttctgggaa gcctcggaac gcaccattcg ttccgaagcc|1080|
|gaggactcgt atcactttt ttctgccaaa atgaccgcca ctttcttatc taagaagcaa|1140|
|gaggtgaaca tgtccgactc tgcgctggac tgtgtacgtg atgaggccat aaataagtta|1200|
|cagcagattt tcaatacttc atacaatcaa acatatgaaa aatatggaaa cgtgtccgtc|1260|
|tttgaaaccca ctggtggttt ggtggtgttc tggcaaggta tcaagcaaaa atctctggtg|1320|
|gaactcgaac gtttggccaa ccgctccagt ctgaatctta ctcataatag aaccaaaaga|1380|
|agtacagatg caacaatgc aactcattta tccaacatgg agtcggtgca aatctggtc|1440|
|tacgcccagc tgcagttcac ctatgacacg ttgcgcggtt acatcaaccg ggcgctggcg|1500|
|caaatcgcag aagcctggtg tgtggatcaa cggcgcaccc tagaggtctt caaggaactt|1560|
|agcaagatca cccgtcagc tattctctcg gccatctaca acaaaccgat tgccgcgcgt|1620|

```
ttcatgggtg atgtcctggg tctggccagc tgcgtgacca ttaaccaaac cagcgtcaag    1680
gtgctgcgtg atatgaatgt gaaggaatcg ccaggacgct gctactcacg accagtggtc    1740
atctttaatt tcgccaacag ctcgtacgtg cagtacggtc aactgggcga ggataacgaa    1800
atcctgttgg gcaaccaccg cactgaggaa tgtcagcttc ccagcctcaa gatcttcatc    1860
gccggcaact cggcctacga gtacgtggac tacctcttca aacgcatgat tgacctcagc    1920
agcatctcca ccgtcgacag catgatcgcc ctagacatcg acccgctgga aaacaccgac    1980
ttcagggtac tggaacttta ctcgcagaaa gaattgcgtt ccatcaacgt ttttgatctc    2040
gaggagatca tgcgcgagtt caattcgtat aagcagcggg taaagtacgt ggaggacaag    2100
gtagtcgacc cgctgccgcc ctacctcaag gtctggacg acctcatgag cggcctgggc    2160
gccgcgggaa aggccgttgg cgtagccatt ggggccgtgg gtggcgcggt ggcctccgtg    2220
gtcgaaggcg ttgccacctt cctcaaaaac cccttcggag ccttcaccat catcctcgtg    2280
gccatagccg tcgtcattat catttatttg atctatactc gacagcggcg tctctgcatg    2340
cagccgctgc agaacctctt tccctatctg gtgtccgccg acgggaccac cgtgacgtcg    2400
ggcaacacca agacacgtc gttacaggct ccgccttcct acgaggaaag tgtttataat    2460
tctggtcgca aaggaccggg accaccgtcg tctgatgcat ccacggcggc tccgccttac    2520
accaacgagc aggcttacca gatgcttctg gccctggtcc gtctggacgc agagcagcga    2580
gcgcagcaga acgtacaga ttctttggac ggacagactg gcacgcagga caagggacag    2640
aagcccaacc tgctagaccg actgcgacac cgcaaaaacg gctaccgaca cttgaaagac    2700
tccgacgaag aagagaacgt ctga                                           2724
```

<210> SEQ ID NO 9
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: Codon Optimized HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 9

```
atggagtcaa ggatttggtg cctggtcgtg tgcgtcaatc tgtgcatcgt ctgtctgggg     60
gctgccgtgt catcaagttc tacaagaggc accagcgcca cccactcaca ccatagctcc    120
cataccacat ccgccgctca ctcccggtct ggcagcgtga gccagagagt cacatctagt    180
cagaccgtga gccacggggt caacgagacc atctacaata ctaccctgaa gtatggcgac    240
gtggtcgggg tgaacacaac taaatacccca tatagggtct gcagtatggc ccagggcact    300
gatctgatta gattcgaaag gaacatcgtg tgcaccagca tgaagcccat taatgaggac    360
ctggatgaag ggatcatggt ggtctacaaa cgcaatattg tggcccatac cttcaaggtg    420
cgagtctatc agaaagtgct gacatttcgg agatcttacg catatatcca caccacatac    480
ctgctgggga gtaacaccga gtatgtggct ccccctatgt gggaaattca ccatatcaat    540
agccattccc agtgctactc aagctacagc agagtgatcg ctggaacagt gttcgtcgca    600
taccacagag actcttatga gaacaagact atgcagctca tgcccgacga ttacagcaat    660
acacattcca ctagatatgt gacagtcaaa gatcagtggc actcaagggg cagcacctgg    720
ctgtaccgcg agacatgcaa cctgaattgt atggtgacta tcactaccgc tagatccaag    780
```

```
taccccctatc acttctttgc aacttccacc ggggacgtgg tcgatatttc tcctttctac    840
aacggcacaa accggaatgc atcttatttt ggggagaacg ccgacaagtt ctttattttc    900
ccaaattaca ccatcgtgtc tgattttggc agacccaaca gtgccctgga gacacatcga    960
ctggtggcat tcctggaacg ggccgactcc gtcatttctt gggacatcca ggatgagaag   1020
aatgtgacct gccagctcac cttctgggag gccagcgaac gcaccatccg atccgaggct   1080
gaagattctt accacttctc ctctgccaaa atgacagcta cttttctgag caagaaacag   1140
gaggtgaaca tgtctgacag tgctctggat tgcgtgcggg acgaagcaat taataagctg   1200
cagcagatct tcaacacatc atacaaccag acttacgaga agtacggaaa cgtgagcgtc   1260
ttcgaaacaa ctggcgggct ggtggtcttt tggcagggca tcaagcagaa atccctggtg   1320
gagctggaaa ggctggccaa tcgcagttca ctgaacctga ctcataatcg gaccaagaga   1380
tctacagacg gaaacaatgc cacacatctg tctaacatgg agagtgtgca aatctggtc    1440 tacgctcagc tccagtttac ctacgacaca ctgagaggct atattaacag ggcactggcc   1500
cagatcgctg aagcatggtg cgtggatcag aggcgcaccc tggaggtctt caaggaactg   1560
tccaaaatca cccttcagc aattctgagc gccatctaca ataagccaat tgcagccagg   1620
tttatgggag acgtgctggg cctggccagt tgcgtcacta tcaaccagac ctcagtgaag   1680
gtcctgcgcg atatgaatgt gaaagagagt cccggcagat gctattcacg gcctgtggtc   1740
atcttcaact ttgctaatag ctcctacgtg cagtatggac agctcggcga ggacaacgaa   1800
attctgctgg ggaatcacag gaccgaggaa tgtcagctcc ctagcctgaa gattttcatc   1860 gctggaaaact ccgcatacga gtatgtggat tacctgttca gcggatgat tgacctgtct   1920 agtatctcca ctgtggattc tatgattgcc ctggacatcg atccactgga aaataccgac   1980
ttcagggtgc tggagctgta tagccagaag gaactgcgct ccatcaacgt gttcgatctg   2040
gaggaaatta tgagagagtt taaatagctac aagcagaggg tgaaatatgt cgaagataag   2100
gtggtcgacc ccctgccacc ctacctgaaa ggcctggacg atctgatgag cgggctggga   2160
gctgcaggga aggcagtggg agtcgctatc ggcgcagtgg gaggagccgt ggccagcgtg   2220
gtcgagggag tggcaacatt cctgaaaaac cccttcgggg ccttcaccat cattctggtg   2280
gcaatcgccg tggtcatcat tatctacctg atctacacaa ggcagcggcg gctgtgcatg   2340
cagcctctgc agaacctgtt tccatacctg gtgagcgccg acgggaccac agtcacctca   2400
ggaaatacta aggataccctc tctgcaggcc cccccaagtt acgaggaatc agtgtataac   2460
agcggcagaa aaggaccagg accaccttca agcgacgcca gcactgccgc tccaccctac   2520
accaatgagc aggcctatca gatgctgctg ctctggtgc cctggatgc cgaacagcga   2580 gctcagcaga acgggaccga ctccctggat ggacagaccg aaacacagga caagggacag   2640
aaacctaatc tgctggatcg gctgcggcac agaaaaaacg ggtataggca cctgaaggac   2700
tccgacgaag aagaaaatgt ctaa                                          2724
```

<210> SEQ ID NO 10
<211> LENGTH: 795
<212> TYPE: PRT
<213> ORGANISM: Human cytomegalovirus
<220> FEATURE:
<221> NAME/KEY: MISC_FEATURE
<222> LOCATION: (1)..(795)
<223> OTHER INFORMATION: HCMV gB-G Amino Acid Sequence
<220> FEATURE:
<221> NAME/KEY: MISC_FEATURE
<222> LOCATION: (751)..(795)

<223> OTHER INFORMATION: TM and CTD

<400> SEQUENCE: 10

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
            195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
            275                 280                 285

Tyr Phe Gly Glu Asn Ala Asp Lys Phe Ile Phe Pro Asn Tyr Thr
            290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
            370                 375                 380

Ser Asp Ser Ala Leu Asp Cys Val Arg Asp Glu Ala Ile Asn Lys Leu
385                 390                 395                 400
```

-continued

```
Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ile Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Phe Phe Ile Ile Gly Leu Ile Ile Gly Leu Phe Leu Val Leu Arg Val
        755                 760                 765

Gly Ile His Leu Cys Ile Lys Leu Lys His Thr Lys Arg Gln Ile
    770                 775                 780

Tyr Thr Asp Ile Glu Met Asn Arg Leu Gly Lys
785                 790                 795
```

<210> SEQ ID NO 11
<211> LENGTH: 2388
<212> TYPE: DNA

<213> ORGANISM: Human cytomegalovirus
<220> FEATURE:
<221> NAME/KEY: misc_feature
<222> LOCATION: (1)..(2388)
<223> OTHER INFORMATION: HCMV gB - G Nucleotide Sequence
<220> FEATURE:
<221> NAME/KEY: misc_feature
<222> LOCATION: (2253)..(2388)
<223> OTHER INFORMATION: TM and CTD

<400> SEQUENCE: 11

| | | | | | |
|---|---|---|---|---|---|
| atggaatcca | ggatctggtg | cctggtagtc | tgcgttaact | tgtgtatcgt | ctgtctgggt | 60 |
| gctgcggttt | cctcatcttc | tactcgtgga | acttctgcta | ctcacagtca | ccattcctct | 120 |
| catacgacgt | ctgctgctca | ttctcgatcc | ggttcagtct | ctcaacgcgt | aacttcttcc | 180 |
| caaacggtca | gccatggtgt | taacgagacc | atctacaaca | ctaccctcaa | gtacggagat | 240 |
| gtggtggggg | tcaacaccac | caagtacccc | tatcgcgtgt | gttctatggc | acagggtacg | 300 |
| gatcttattc | gctttgaacg | taatatcgtc | tgcacctcga | tgaagcccat | caatgaagac | 360 |
| ctggacgagg | gcatcatggt | ggtctacaaa | cgcaacatcg | tcgcgcacac | ctttaaggta | 420 |
| cgagtctacc | agaaggtttt | gacgtttcgt | cgtagctacg | cttacatcca | caccacttat | 480 |
| ctgctgggca | gcaacacgga | atacgtggcg | cctcctatgt | gggagattca | tcatatcaac | 540 |
| agtcacagtc | agtgctacag | ttcctacagc | cgcgttatag | caggcacggt | tttcgtggct | 600 |
| tatcataggg | acagctatga | aaacaaaacc | atgcaattaa | tgcccgacga | ttattccaac | 660 |
| acccacagta | cccgttacgt | gacggtcaag | gatcaatggc | acagccgcgg | cagcacctgg | 720 |
| ctctatcgtg | agacctgtaa | tctgaattgt | atggtgacca | tcactactgc | gcgctccaag | 780 |
| tatccctatc | attttttcgc | aacttccacg | ggtgatgtgg | ttgacatttc | tccttttctac | 840 |
| aacggaacta | atcgcaatgc | cagctatttt | ggagaaaacg | ccgacaagtt | tttcattttt | 900 |
| ccgaactaca | ctatcgtctc | cgactttgga | agaccgaatt | ctgcgttaga | gacccacagg | 960 |
| ttggtggctt | tcttgaacg | tgcggactca | gtgatctcct | gggatataca | ggacgagaag | 1020 |
| aatgttactt | gtcaactcac | tttctgggaa | gcctcggaac | gcaccattcg | ttccgaagcc | 1080 |
| gaggactcgt | atcactttc | ttctgccaaa | atgaccgcca | ctttcttatc | taagaagcaa | 1140 |
| gaggtgaaca | tgtccgactc | tgcgctggac | tgtgtacgtg | atgaggccat | aaataagtta | 1200 |
| cagcagattt | tcaatacttc | atacaatcaa | acatatgaaa | aatatggaaa | cgtgtccgtc | 1260 |
| tttgaaacca | ctggtggttt | ggtggtgttc | tggcaaggta | tcaagcaaaa | atctctggtg | 1320 |
| gaactcgaac | gtttggccaa | ccgctccagt | ctgaatctta | tcataatag | aaccaaaaga | 1380 |
| agtacagatg | gcaacaatgc | aactcattta | tccaacatgg | agtcggtgca | caatctggtc | 1440 |
| tacgcccagc | tgcagttcac | ctatgacacg | ttgcgcggtt | acatcaaccg | ggcgctggcg | 1500 |
| caaatcgcag | aagcctggtg | tgtggatcaa | cggcgcaccc | tagaggtctt | caaggaactt | 1560 |
| agcaagatca | cccgtcagc | tattctctcg | gccatctaca | caaaccgat | gccgcgcgt | 1620 |
| ttcatgggtg | atgtcctggg | tctggccagc | tgcgtgacca | ttaaccaaac | cagcgtcaag | 1680 |
| gtgctgcgtg | atatgaatgt | gaaggaatcg | ccaggacgct | gctactcacg | accagtggtc | 1740 |
| atctttaatt | tcgccaacag | ctcgtacgtg | cagtacggtc | aactgggcga | ggataacgaa | 1800 |
| atcctgttgg | gcaaccaccg | cactgaggaa | tgtcagcttc | ccagcctcaa | gatcttcatc | 1860 |
| gccggcaact | cggcctacga | gtacgtggac | tacctcttca | aacgcatgat | tgacctcagc | 1920 |
| agcatctcca | ccgtcgacag | catgatcgcc | ctagacatcg | acccgctgga | aaacaccgac | 1980 |
| ttcagggtac | tggaacttta | ctcgcagaaa | gaattgcgtt | ccatcaacgt | ttttgatctc | 2040 |

```
gaggagatca tgcgcgagtt caattcgtat aagcagcggg taaagtacgt ggaggacaag    2100
gtagtcgacc cgctgccgcc ctacctcaag ggtctggacg acctcatgag cggcctgggc    2160
gccgcgggaa aggccgttgg cgtagccatt ggggccgtgg gtggcgcggt ggcctccgtg    2220
gtcgaaggcg ttgccacctt cctcaaaaac ccctttttct ttatcatagg gttaatcatt    2280
ggactattct tggttctccg agttggtatc catctttgca ttaaattaaa gcacaccaag    2340
aaaagacaga tttatacaga catagagatg aaccgacttg aaagtaa                  2388
```

<210> SEQ ID NO 12
<211> LENGTH: 2388
<212> TYPE: DNA
<213> ORGANISM: Human cytomegalovirus
<220> FEATURE:
<221> NAME/KEY: misc_feature
<222> LOCATION: (1)..(2388)
<223> OTHER INFORMATION: Codon Optimized HCMV gB - G Nucleotide Sequence
<220> FEATURE:
<221> NAME/KEY: misc_feature
<222> LOCATION: (2253)..(2388)
<223> OTHER INFORMATION: TM and CTD

<400> SEQUENCE: 12

```
atggagtcaa ggatttggtg tctggtcgtc tgcgtcaacc tgtgcattgt ctgcctggga      60
gccgccgtct catcatcatc tacccgaggc acatccgcca ctcactctca ccatagctcc     120
cataccacat ccgccgctca ctcaagaagc gggtccgtgt ctcagagggt cacatctagt     180
cagaccgtga gccatggagt caacgagaca atctacaata ctaccctgaa gtatggagac     240
gtggtcggcg tgaacacaac taaataccccc tatagggtct gctctatggc caggggaca    300 gatctgatcc gatttgaacg gaacatcgtg tgcactagca tgaagcctat caatgaggac     360
ctggatgaag gaattatggt ggtctacaaa cgaaatatcg tggcccatac ttttaaggtg     420
agagtctatc agaaagtgct gaccttccgg agaagctacg cttatattca caccacatac     480
ctgctggggt ccaacaccga gtatgtggca cccctatgt gggaaatcca ccatattaat      540
agtcattcac agtgctactc aagctacagc agagtgatcg ctggaaccgt gttcgtcgca     600
taccacagag acagttatga gaacaagaca atgcagctca tgcccgacga ttacagtaat     660
acccattcaa caagatatgt gaccgtcaaa gatcagtggc actctcgcgg cagtacctgg     720
ctgtaccgag agacatgcaa cctgaattgt atggtgacaa ttactaccgc agaagcaag     780 taccctttatc acttctttgc tacctcaaca ggggacgtgg tcgacatcag ccccttctac     840
aacgaaacaa accggaatgc ctcctatttc ggcgagaacg ctgacaaatt ctttatcttc     900
cccaactaca ctatcgtgag cgattcggc agacctaaca gtgccctgga cccatcgg      960 ctggtggcat ttctggaaag agccgacagc gtgatctcct gggacattca ggatgagaag    1020
aatgtgacct gccagctcac cttctgggag gccagcgaaa gaaccatcag gtccgaggca     1080
gaagattctt accactttttc ctctgcaaaa atgactgcca ccttcctgtc caagaaacag    1140
gaggtgaaca tgagcgactc cgcactggat tgcgtgcggg acgaagccat caataagctg    1200
cagcagatct tcaacacatc ttacaaccag acttacgaga gtacggcaa cgtgagtgtc     1260 tttgaaacaa ctggcgggct ggtggtcttc tggcagggga tcaagcagaa atctctggtg    1320
gagctggaac ggctggccaa tagaagttca ctgaacctga ctcataatcg caccaagcga    1380
tccacagacg aaacaatgc aactcatctg agcaacatgg agtccgtgca caatctggtc    1440
tacgcccagc tccagttcac ttacgacacc ctgcgaggct atatcaaccg ggccctggct    1500
```

```
cagattgcag aagcctggtg cgtggatcag aggcgcaccc tggaggtctt taaggaactg    1560
agcaaaatta acccatctgc tatcctgagt gcaatctaca ataagcccat cgcagccagg    1620
ttcatggggg acgtgctggg actggcctcc tgcgtcacta tcaaccagac ctctgtgaag    1680
gtcctgcgcg atatgaatgt gaaagagagt cctggcaggt gttattcacg cccagtggtc    1740
atcttcaact tcgctaatag ctcctacgtg cagtatggcc agctcgggga ggacaacgaa    1800
atcctgctgg gaaatcacag gaccgaggaa tgtcagctcc caagtctgaa gatctttatt    1860
gccggcaact cagcttacga gtatgtggat tacctgttca aacgcatgat cgacctgtct    1920
agtatttcaa cagtggatag catgatcgcc ctggacattg atcccctgga aaatactgac    1980
ttcagggtgc tggagctgta tagccagaag gaactgcgct ccattaacgt gtttgatctg    2040
gaggaaatca tgagggagtt caattcctac aagcagcgcg tgaaatatgt cgaagataag    2100
gtggtcgacc ctctgccacc ctacctgaaa ggcctggacg atctgatgag cgggctggga    2160
gctgcaggca aggcagtggg agtcgccatc ggagctgtgg gaggcgctgt cgcatccgtg    2220
gtcgagggag tggctacctt tctgaagaac ccattctttt tcatcatcgg cctgatcatt    2280
gggctgttcc tggtgctgag agtcggcatc cacctgtgca ttaagctgaa gcacaccaag    2340
aagaggcaga tctacaccga tattgaaatg aacagactgg gcaagtga                 2388
```

<210> SEQ ID NO 13
<211> LENGTH: 742
<212> TYPE: PRT
<213> ORGANISM: Human cytomegalovirus
<220> FEATURE:
<221> NAME/KEY: MISC_FEATURE
<222> LOCATION: (1)..(742)
<223> OTHER INFORMATION: HCMV gH Amino Acid Sequence
<220> FEATURE:
<221> NAME/KEY: MISC_FEATURE
<222> LOCATION: (717)..(742)
<223> OTHER INFORMATION: TM and CTD

<400> SEQUENCE: 13

```
Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Gln Thr Pro His Gly
                165                 170                 175
```

```
Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
    530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590

Asn Gln Tyr Leu Ile Lys Gly Ile Ser Tyr Pro Val Ser Thr Thr Val
```

|     |     |     |     |     | 595 |     |     |     |     | 600 |     |     |     |     | 605 |
| --- | --- | --- | --- | --- | --- | --- | --- | --- | --- | --- | --- | --- | --- | --- | --- |

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
                675                 680                 685

Ser Pro Arg Thr His Tyr Leu Met Leu Leu Lys Asn Gly Thr Val Leu
690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
                740

<210> SEQ ID NO 14
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 14

| | | |
|---|---|---|
| atgcggccag gcctcccctc ctacctcatc gtcctcgccg tctgtctcct cagccaccta | 60 |
| ctttcgtcac gatatggcgc agaagccata tccgaaccgc tggacaaagc gtttcaccta | 120 |
| ctgctcaaca cctacgggag acccatccgc ttcctgcgtg aaaacaccac ccagtgtacc | 180 |
| tacaatagca gcctccgtaa cagcacggtc gtcagggaaa acgccatcag tttcaacttt | 240 |
| ttccaaagct ataatcaata ctatgtattc catatgcctc gatgtctttt tgcgggtcct | 300 |
| ctggcggagc agtttctgaa ccaggtagat ctgaccgaaa ccctggaaag ataccaacag | 360 |
| agacttaaca cttacgcgct ggtatccaaa gacctggcca gctaccgatc tttttcgcag | 420 |
| cagctaaagg cacaggacag cctaggtgaa cagcccacca ctgtgccacc acccattgac | 480 |
| ctgtcaatac ctcacgtttg gatgccaccg caaaccactc acacggctg acagaatca | 540 |
| cataccacct caggactaca ccgaccacac tttaaccaga cctgtatcct ctttgatgga | 600 |
| cacgatctac tattcagcac cgtcacacct tgtttgcacc aaggctttta cctcatcgac | 660 |
| gaactacgtt acgttaaaat aacactgacc gaggacttct tcgtagttac ggtgtccata | 720 |
| gacgacgaca cacccatgct gcttatcttc ggccatcttc cacgcgtact ctttaaagcg | 780 |
| ccctatcaac gcgacaactt tatactacga caaactgaaa acacgagct cctggtgcta | 840 |
| gttaagaaag atcaactgaa ccgtcactct tatctcaaag acccggactt tcttgacgcc | 900 |
| gcacttgact tcaactacct ggacctcagc gcactactac gtaacagctt caccgttac | 960 |
| gccgtggatg tactcaaaag cggtcgatgt cagatgctgg accgccgcac ggtagaaatg | 1020 |

```
gccttcgcct acgcattagc actgttcgca gcagcccgac aagaagaggc cggcgcccaa    1080
gtctccgtcc cacgggccct agaccgccag gccgcactct acaaataca agaatttatg    1140 atcacctgcc tctcacaaac accaccacgc accacgttgc tgctgtatcc cacggccgtg    1200
gacctggcca acgagccct ttggacaccg aatcagatca ccgacatcac cagcctcgta    1260
cgcctggtct acatactctc taaacagaat cagcaacatc tcatccccca gtgggcacta    1320
cgacagatcg ccgactttgc cctaaaacta cacaaaacgc acctggcctc ttttctttca    1380
gccttcgcgc gtcaagaact ctacctcatg ggcagcctcg tccactccat gctagtacat    1440
acgacggaga gacgcgaaat cttcatcgta gaaacgggcc tctgttcatt agccgagcta    1500
tcacacttta cgcagttgct agctcatccg caccacgaat acctcagcga cctgtacaca    1560
ccctgttcca gtagcgggcg acgcgatcac tcgctcgaac gcctcacacg tctcttcccc    1620
gatgccaccg tccccactac cgttcccgcc gccctctcca tcctatctac catgcaacca    1680
agcacgctag aaaccttccc cgacctgttt tgtctgccgc tcggcgaatc cttctccgcg    1740
ctgaccgtct ccgaacacgt cagttatgtc gtaacaaacc agtacctgat caaaggtatc    1800
tcctaccctg tctccaccac cgtcgtaggc cagagcctca tcatcaccca gacggacagt    1860
caaactaaat gcgaactgac gcgcaacatg cataccacac acagcatcac agcggcgctc    1920
aacatttccc tagaaaactg cgccttttgc caaagcgccc tactagaata cgacgacacg    1980
caaggcgtca tcaacatcat gtacatgcac gactcggacg acgtccttt cgccctggat    2040 ccctacaacg aagtggtggt ctcatctccg cgaactcact acctcatgct tttgaaaaac    2100
ggtacggtcc tagaagtaac tgacgtcgtc gtggacgcta ccgacagtcg tctcctcatg    2160
atgtccgtct acgcgctatc ggccatcatc ggcatctatc tgctctaccg catgctcaag    2220
acatgctga                                                            2229

<210> SEQ ID NO 15
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: Codon Optimized HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 15
atgagacctg gactgccttc ttatctgatt gtgctggccg tctgcctgct gtcacatctg     60
ctgagttcac gctatggggc tgaggctatc tccgagccac tggacaaggc ttttcacctg    120
ctgctgaaca cctacgggag acccattagg ttcctgcgcg agaataccac acagtgcaca    180
tataacagct ccctgcggaa cagcactgtg gtccgcgaaa cgccatctc ttttaatttc    240 tttcagagtt acaaccagta ctacgtgttc catatgccac gctgtctgtt tgcaggaccc    300
ctggccgagc agttcctgaa ccaggtggac ctgaccgaga cactggaaag ataccagcag    360
aggctgaata cctatgccct ggtgagtaag gatctggctt catatcggtc tttcagtcag    420
cagctcaagg cccaggactc actgggcgag cagcctacta ccgtgccccc tccaatcgat    480
ctgagcattc acacgtctg gatgcccct cagacaactc ccacggctg gaccgaaagc    540 cataccacat ccgggctgca cagacccat ttcaaccaga catgcatcct gtttgatggg    600
cacgacctgc tgttcagcac tgtgacccct tgtctgcatc agggattcta cctgatcgat    660
```

```
gagctgagat atgtgaaaat tacactgact gaagacttct ttgtggtcac cgtgagcatc    720
gacgatgaca caccaatgct gctgattttt ggacacctgc cccgggtgct gttcaaggcc    780
ccctaccagc gagacaactt tattctgcgg cagaccgaga acacgaact gctggtgctg     840 gtcaagaaag atcagctcaa caggcatagc tatctgaagg accccgactt tctggatgcc    900
gctctggact tcaactacct ggacctgtca gcactgctgc ggaatagctt ccacagatat    960
gccgtggatg tcctgaaatc cggaagatgc cagatgctgg accggagaac cgtggagatg   1020
gcatttgcct acgctctggc actgttcgca gccgctaggc aggaggaagc aggcgctcag   1080
gtgtccgtcc ctcgcgcact ggatcgacag gcagccctgc tgcagatcca ggagttcatg   1140
attacctgtc tgtctcagac accacccaga actaccctgc tgctgtaccc cactgccgtg   1200
gacctggcta gagggcact gtggaccct aaccagatca ctgatattac ctctctggtg     1260
cgcctggtct atatcctgag taaacagaat cagcagcacc tgatcccaca gtgggccctg   1320
cgacagattg ccgacttcgc tctgaagctg cacaaaaccc atctggcttc cttcctgtct   1380
gcatttgccc gccaggagct gtacctgatg ggctctctgg tgcacagtat gctggtccat   1440
acaactgaga ggcgcgaaat ctttattgtg gagacagggc tgtgcagcct ggctgaactg   1500
tcccacttca ctcagctcct ggcccatcct caccatgagt acctgtccga tctgtatacc   1560
ccatgttcta gttcaggccg acgggaccac tctctggaac gactgactcg gctgtttcct   1620
gatgcaaccg tgcctaccac cgtgcccgcc gccctgagta tcctgtcaac aatgcagcca   1680
agcacactgg agactttccc cgacctgttt tgcctgcctc tggggagtc attcagcgcc    1740 ctgaccgtgt cagaacatgt cagctacgtg gtcacaaacc agtatctgat caagggaatt    1800
tcctaccccg tgtctactac cgtggtcggc cagagtctga tcattaccca gacagattca   1860
cagactaaat gtgagctgac ccggaatatg cacacaactc atagcatcac cgccgctctg   1920
aacatttccc tggagaattg cgcttttttgt cagagtgcac tgctggaata cgatgacaca    1980
cagggcgtga tcaacattat gtatatgcac gatagcgatg acgtgctgtt cgctctggac   2040
ccctacaacg aggtggtcgt gagctccccct cgcactcatt atctgatgct gctgaagaat   2100
ggaacagtgc tggaagtcac tgatgtcgtg gtcgatgcca cagactcccg gctgctgatg   2160
atgtctgtgt acgcactgtc cgccatcatc ggcatctatc tgctgtatcg aatgctgaaa   2220
acctgttga                                                            2229
```

<210> SEQ ID NO 16
<211> LENGTH: 761
<212> TYPE: PRT
<213> ORGANISM: Human cytomegalovirus
<220> FEATURE:
<221> NAME/KEY: MISC_FEATURE
<222> LOCATION: (1)..(761)
<223> OTHER INFORMATION: HCMV gH - G Amino Acid Sequence
<220> FEATURE:
<221> NAME/KEY: MISC_FEATURE
<222> LOCATION: (717)..(761)
<223> OTHER INFORMATION: TM and CTD

<400> SEQUENCE: 16

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro
        35                  40                  45

-continued

```
Ile Arg Phe Leu Arg Glu Asn Thr Thr Gln Cys Thr Tyr Asn Ser Ser
 50                  55                  60

Leu Arg Asn Ser Thr Val Val Arg Glu Asn Ala Ile Ser Phe Asn Phe
 65                  70                  75                  80

Phe Gln Ser Tyr Asn Gln Tyr Tyr Val Phe His Met Pro Arg Cys Leu
                 85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
                260                 265                 270

Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
            355                 360                 365

Arg Gln Ala Ala Leu Leu Gln Ile Gln Glu Phe Met Ile Thr Cys Leu
370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
450                 455                 460
```

-continued

```
Gln Glu Leu Tyr Leu Met Gly Ser Leu Val His Ser Met Leu Val His
465                 470                 475                 480
Thr Thr Glu Arg Arg Glu Ile Phe Ile Val Glu Thr Gly Leu Cys Ser
                485                 490                 495
Leu Ala Glu Leu Ser His Phe Thr Gln Leu Leu Ala His Pro His His
            500                 505                 510
Glu Tyr Leu Ser Asp Leu Tyr Thr Pro Cys Ser Ser Gly Arg Arg
        515                 520                 525
Asp His Ser Leu Glu Arg Leu Thr Arg Leu Phe Pro Asp Ala Thr Val
    530                 535                 540
Pro Thr Thr Val Pro Ala Ala Leu Ser Ile Leu Ser Thr Met Gln Pro
545                 550                 555                 560
Ser Thr Leu Glu Thr Phe Pro Asp Leu Phe Cys Leu Pro Leu Gly Glu
                565                 570                 575
Ser Phe Ser Ala Leu Thr Val Ser Glu His Val Ser Tyr Val Val Thr
            580                 585                 590
Asn Gln Tyr Leu Ile Lys Gly Ile Ser Tyr Pro Val Ser Thr Thr Val
        595                 600                 605
Val Gly Gln Ser Leu Ile Ile Thr Gln Thr Asp Ser Gln Thr Lys Cys
    610                 615                 620
Glu Leu Thr Arg Asn Met His Thr Thr His Ser Ile Thr Ala Ala Leu
625                 630                 635                 640
Asn Ile Ser Leu Glu Asn Cys Ala Phe Cys Gln Ser Ala Leu Leu Glu
                645                 650                 655
Tyr Asp Asp Thr Gln Gly Val Ile Asn Ile Met Tyr Met His Asp Ser
            660                 665                 670
Asp Asp Val Leu Phe Ala Leu Asp Pro Tyr Asn Glu Val Val Val Ser
        675                 680                 685
Ser Pro Arg Thr His Tyr Leu Met Leu Leu Lys Asn Gly Thr Val Leu
    690                 695                 700
Glu Val Thr Asp Val Val Val Asp Ala Thr Asp Ser Arg Phe Phe Phe
705                 710                 715                 720
Ile Ile Gly Leu Ile Ile Gly Leu Phe Leu Val Leu Arg Val Gly Ile
                725                 730                 735
His Leu Cys Ile Lys Leu Lys His Thr Lys Lys Arg Gln Ile Tyr Thr
            740                 745                 750
Asp Ile Glu Met Asn Arg Leu Gly Lys
        755                 760

<210> SEQ ID NO 17
<211> LENGTH: 2286
<212> TYPE: DNA
<213> ORGANISM: Human cytomegalovirus
<220> FEATURE:
<221> NAME/KEY: misc_feature
<222> LOCATION: (1)..(2286)
<223> OTHER INFORMATION: HCMV gH - G Nucleotide Sequence
<220> FEATURE:
<221> NAME/KEY: misc_feature
<222> LOCATION: (2151)..(2286)
<223> OTHER INFORMATION: TM and CTD

<400> SEQUENCE: 17
atgcggccag gcctcccctc ctacctcatc gtcctcgccg tctgtctcct cagccaccta      60
ctttcgtcac gatatggcgc agaagccata tccgaaccgc tggacaaagc gtttcaccta     120
ctgctcaaca cctacgggag acccatccgc ttcctgcgtg aaaacaccac ccagtgtacc     180
```

```
tacaatagca gcctccgtaa cagcacggtc gtcagggaaa acgccatcag tttcaacttt    240
ttccaaagct ataatcaata ctatgtattc catatgcctc gatgtctttt tgcgggtcct    300
ctggcggagc agtttctgaa ccaggtagat ctgaccgaaa ccctggaaag ataccaacag    360
agacttaaca cttacgcgct ggtatccaaa gacctggcca gctaccgatc ttttcgcag     420 cagctaaagg cacaggacag cctaggtgaa cagcccacca ctgtgccacc acccattgac    480
ctgtcaatac ctcacgtttg gatgccaccg caaaccactc cacacggctg gacagaatca    540
cataccacct caggactaca ccgaccacac tttaaccaga cctgtatcct ctttgatgga    600
cacgatctac tattcagcac cgtcacacct tgtttgcacc aaggctttta cctcatcgac    660
gaactacgtt acgttaaaat aacactgacc gaggacttct tcgtagttac ggtgtccata    720
gacgacgaca cacccatgct gcttatcttc ggccatcttc cacgcgtact ctttaaagcg    780
ccctatcaac gcgacaactt tatactacga caaactgaaa aacacgagct cctggtgcta    840
gttaagaaag atcaactgaa ccgtcactct tatctcaaag accgggactt tcttgacgcc    900
gcacttgact tcaactacct ggacctcagc gcactactac gtaacagctt tcaccgttac    960
gccgtggatg tactcaaaag cggtcgatgt cagatgctgg accgccgcac ggtagaaatg   1020
gccttcgcct acgcattagc actgttcgca gcagcccgac aagaagaggc cggcgcccaa   1080
gtctccgtcc cacgggccct agaccgccag gccgcactct acaaatacag agaatttatg   1140
atcacctgcc tctcacaaac accaccacgc accacgttgc tgctgtatcc cacggccgtg   1200
gacctggcca aacgagccct ttggacaccg aatcagatca ccgacatcac cagcctcgta   1260
cgcctggtct acatactctc taaacagaat cagcaacatc tcatccccca gtgggcacta   1320
cgacagatcg ccgactttgc cctaaaacta cacaaaacgc acctggcctc ttttctttca   1380
gccttcgcgc gtcaagaact ctacctcatg ggcagcctcg tccactccat gctagtacat   1440
acgacggaga gacgcgaaat cttcatcgta gaaacgggcc tctgttcatt agccgagcta   1500
tcacacttta cgcagttgct agctcatccg caccacgaat acctcagcga cctgtacaca   1560
ccctgttcca gtagcgggcg acgcgatcac tcgctcgaac gcctcacacg tctcttcccc   1620
gatgccaccg tccccactac cgttcccgcc gccctctcca tcctatctac catgcaacca   1680
agcacgctag aaaccttccc cgacctgttt tgtctgccgc tcggcgaatc cttctccgcg   1740
ctgaccgtct ccgaacacgt cagttatgtc gtaacaaacc agtacctgat caaaggtatc   1800
tcctaccctg tctccaccac cgtcgtaggc cagagcctca tcatcaccca gacggacagt   1860
caaactaaat gcgaactgac gcgcaacatg cataccacac acagcatcac agcggcgctc   1920
aacatttccc tagaaaactg cgccttttgc caaagcgccc tactagaata cgacgacacg   1980
caaggcgtca tcaacatcat gtacatgcac gactcggacg acgtcctttt cgccctggat   2040
ccctacaacg aagtggtggt ctcatctccg cgaactcact acctcatgct tttgaaaaac   2100
ggtacggtcc tagaagtaac tgacgtcgtc gtggacgcta ccgacagtcg ttttttcttt   2160
atcatagggt taatcattgg actattcttg gttctccgag ttggtatcca tctttgcatt   2220
aaattaaagc acaccaagaa aagacagatt tatacagaca tagagatgaa ccgacttgga   2280
aagtaa                                                             2286
```

<210> SEQ ID NO 18
<211> LENGTH: 2286
<212> TYPE: DNA
<213> ORGANISM: Human cytomegalovirus
<220> FEATURE:
<221> NAME/KEY: misc_feature
<222> LOCATION: (2151)..(2286)
<223> OTHER INFORMATION: TM and CTD
<220> FEATURE:
<221> NAME/KEY: misc_feature
<222> LOCATION: (2151)..(2286)
<223> OTHER INFORMATION: Codon Optimized HCMV gH - G Nucleotide Sequence

<400> SEQUENCE: 18

```
atgcgacccg gactgccaag ctacctgatt gtcctggctg tctgtctgct gtcacacctg     60
ctgagttcaa gatatggggc cgaagccatc agcgagccac tggacaaggc tttccacctg    120
ctgctgaaca cctacggcag acccattagg tttctgcgcg agaataccac acagtgcaca    180
tataacagct ccctgaggaa tagcactgtg gtccgcgaaa acgccatctc tttcaatttc    240
tttcagagtt acaaccagta ctacgtgttc catatgccac gctgtctgtt cgcaggaccc    300
ctggccgagc agtttctgaa ccaggtggac ctgaccgaga cactggaaag ataccagcag    360
aggctgaata cctatgccct ggtgagtaag gatctggctt catatcggtc tttcagtcag    420
cagctcaagg cccaggactc tctgggagag cagcctacta ccgtgccccc tccaatcgat    480
ctgagtattc cacacgtctg gatgccccct cagacaactc cccacggatg gaccgaaagc    540
cataccacat ccggcctgca cagaccccac ttcaaccaga catgcatcct gttcgatggc    600
cacgacctgc tgttttccac tgtgacccct tgtctgcatc aggggttcta cctgatcgat    660
gagctgagat atgtgaagat tacactgact gaagacttct ttgtggtcac cgtgtctatc    720
gacgatgaca caccaatgct gctgattttc ggacacctgc cccgggtgct gttcaaggcc    780
ccctaccagc gagacaactt catcctgcgg cagaccgaga aacacgaact gctggtgctg    840
gtcaagaaag atcagctcaa ccggcattcc tatctgaagg accccgactt cctggatgcc    900
gctctggact ttaactacct ggacctgtca gcactgctgc ggaatagctt tcacagatat    960
gccgtggatg tcctgaaatc tgggcgctgc cagatgctgg accggagaac cgtggagatg   1020
gcattcgcct acgctctggc actgtttgca gccgctcggc aggaggaagc aggagctcag   1080
gtgagtgtcc ctcgcgcact ggatcgacag gcagccctgc tgcagatcca ggagttcatg   1140
attacctgtc tgagccagac accacccaga actaccctgc tgctgtaccc cactgccgtg   1200
gacctggcta agagggcact gtggacccct aaccagatca ctgatattac cagcctggtg   1260
agactggtct atatcctgtc caaacagaat cagcagcacc tgatcccaca gtgggccctg   1320
aggcagattg ccgactttgc tctgaagctg cacaaaaccc atctggcttc ctttctgtct   1380
gcattcgcca gacaggagct gtacctgatg ggatctctgg tgcacagtat gctggtccat   1440
acaactgaga ggcgcgaaat cttcattgtg gagacaggcc tgtgcagcct ggctgaactg   1500
tcccacttta ctcagctcct ggcccatcct caccatgagt acctgtcaga tctgtatacc   1560
ccatgttcta gttcaggacg acgggaccac agcctggaac gactgactcg gctgttccct   1620
gatgcaaccg tgcctaccac cgtgcccgcc gccctgagta tcctgtcaac aatgcagcca   1680
agcacactgg agacttttcc cgacctgttc tgcctgcctc tgggcgagag cttcagcgcc   1740
ctgaccgtga gcgaacatgt cagctacgtg gtcacaaacc agtatctgat caaggggatt   1800
tcctaccccg tgtctactac cgtggtcgga cagtccctga tcattaccca gacagattct   1860
cagactaaat gtgagctgac cagaaatatg cacacaactc atagtatcac cgccgctctg   1920
aacatttcac tggagaattg cgctttctgt cagtccgcac tgctggaata cgatgacaca   1980
cagggcgtga tcaacattat gtatatgcac gattctgatg acgtgctgtt tgctctggac   2040
ccctacaacg aggtggtcgt gagctccccc agaactcatt atctgatgct gctgaagaat   2100
```

| | |
|---|---:|
| ggcacagtgc tggaagtcac tgatgtcgtg gtcgatgcca cagactcccg cttcttttc | 2160 |
| atcattggcc tgatcattgg gctgttcctg gtgctgcgag tcggcatcca cctgtgcatc | 2220 |
| aagctgaagc atacaaagaa gagacagatc tacaccgata ttgaaatgaa caggctgggc | 2280 |
| aaatga | 2286 |

```
<210> SEQ ID NO 19
<211> LENGTH: 4895
<212> TYPE: DNA
<213> ORGANISM: Artificial Sequence
<220> FEATURE:
<223> OTHER INFORMATION: Propol II Expression Plasmid
<220> FEATURE:
<221> NAME/KEY: misc_feature
<222> LOCATION: (1)..(4895)
<223> OTHER INFORMATION: Propol II Expression Plasmid Nucleotide
      Sequence

<400> SEQUENCE: 19
```

| | |
|---|---:|
| ctagagagct tggcccattg catacgttgt atccatatca taatatgtac atttatattg | 60 |
| gctcatgtcc aacattaccg ccatgttgac attgattatt gactagttat taatagtaat | 120 |
| caattacggg gtcattagtt catagcccat atatggagtt ccgcgttaca taacttacgg | 180 |
| taaatggccc gcctggctga ccgcccaacg acccccgccc attgacgtca ataatgacgt | 240 |
| atgttcccat agtaacgcca atagggactt tccattgacg tcaatgggtg gagtatttac | 300 |
| ggtaaactgc ccacttggca gtacatcaag tgtatcatat gccaagtacg ccccctattg | 360 |
| acgtcaatga cggtaaatgg cccgcctggc attatgccca gtacatgacc ttatgggact | 420 |
| ttcctacttg gcagtacatc tacgtattag tcatcgctat taccatggtg atgcggtttt | 480 |
| ggcagtacat caatgggcgt ggatagcggt ttgactcacg ggatttcca gtctccacc | 540 |
| ccattgacgt caatgggagt ttgttttggc accaaaatca acgggacttt ccaaaatgtc | 600 |
| gtaacaactc cgccccattg acgcaaatgg gcggtaggcg tgtacggtgg aggtctata | 660 |
| taagcagagc tcgtttagtg aaccgtcaga tcgcctggag acgccatcca cgctgttttg | 720 |
| acctccatag aagacaccgg gaccgatcca gcctccggtc gaccgatcct gagaacttca | 780 |
| gggtgagttt ggggacccct gattgttctt tctttttcgc tattgtaaaa ttcatgttat | 840 |
| atggaggggg caaagttttc agggtgttgt ttagaatggg aagatgtccc ttgtatcacc | 900 |
| atggaccctc atgataattt tgtttctttc actttctact ctgttgacaa ccattgtctc | 960 |
| ctcttatttt cttttcattt tcttgtaact ttttcgttaa actttagctt gcatttgtaa | 1020 |
| cgaattttta aattcacttt tgtttatttg tcagattgta agtactttct ctaatcactt | 1080 |
| tttttcaag gcaatcaggg tatattatat tgtacttcag cacagtttta gagaacaatt | 1140 |
| gttataatta aatgataagg tagaatattt ctgcatataa attctggctg gcgtggaaat | 1200 |
| attcttattg gtagaaacaa ctacatcctg gtcatcatcc tgcctttctc tttatggtta | 1260 |
| caatgatata cactgtttga gatgaggata aaatactctg agtccaaacc gggcccctct | 1320 |
| gctaaccatg ttcatgcctt cttctttttc ctacagctcc tgggcaacgt gctggttatt | 1380 |
| gtgctgtctc atcattttgg caaagaattc ctcgagcgta cgcctagggg atccagcgct | 1440 |
| atttaaatgc tagcatgcat gttaaccctg caggggtacc gcggccgcaa gcttagatcc | 1500 |
| gtcgaggaat tcactcctca ggtgcaggct gcctatcaga aggtggtggc tggtgtggcc | 1560 |
| aatgccctgg ctcacaaata ccactgagat cttttttccct ctgccaaaaa ttatggggac | 1620 |
| atcatgaagc cccttgagca tctgacttct ggctaataaa ggaaatttat tttcattgca | 1680 |

```
atagtgtgtt ggaattttt gtgtctctca ctcggaagga catatgggag ggcaaatcat      1740
ttaaaacatc agaatgagta tttggtttag agtttggcaa catatgccca tatgctggct      1800
gccatgaaca aaggttggct ataaagaggt catcagtata tgaaacagcc ccctgctgtc      1860
cattccttat tccatagaaa agccttgact tgaggttaga ttttttttat attttgtttt      1920
gtgttatttt tttctttaac atccctaaaa ttttccttac atgttttact agccagattt      1980
ttcctcctct cctgactact cccagtcata gctgtccctc ttctcttatg gagatccctc      2040
gacggatcgg ccgcaattcg taatcatgtc atagctgttt cctgtgtgaa attgttatcc      2100
gctcacaatt ccacacaaca tacgagccgg aagcataaag tgtaaagcct ggggtgccta      2160
atgagtgagc taactcacat taattgcgtt gcgctcactg cccgctttcc agtcgggaaa      2220
cctgtcgtgc cagctgcatt aatgaatcgg ccaacgcgcg gggagaggcg gtttgcgtat      2280
tgggcgctct tccgcttcct cgctcactga ctcgctgcgc tcggtcgttc ggctgcggcg      2340
agcggtatca gctcactcaa aggcggtaat acggttatcc acagaatcag gggataacgc      2400
aggaaagaac atgtgagcaa aaggccagca aaaggccagg aaccgtaaaa aggccgcgtt      2460
gctggcgttt ttccataggc tccgcccccc tgacgagcat cacaaaaatc gacgctcaag      2520
tcagaggtgg cgaaacccga caggactata aagataccag gcgtttcccc ctggaagctc      2580
cctcgtgcgc tctcctgttc cgaccctgcc gcttaccgga tacctgtccg cctttctccc      2640
ttcgggaagc gtggcgcttt ctcatagctc acgctgtagg tatctcagtt cggtgtaggt      2700
cgttcgctcc aagctgggct gtgtgcacga accccccgtt cagcccgacc gctgcgcctt      2760
atccggtaac tatcgtcttg agtccaaccc ggtaagacac gacttatcgc cactggcagc      2820
agccactggt aacaggatta gcagagcgag gtatgtaggc ggtgctacag agttcttgaa      2880
gtggtggcct aactacggct acactagaag aacagtattt ggtatctgcg ctctgctgaa      2940
gccagttacc ttcggaaaaa gagttggtag ctcttgatcc ggcaaacaaa ccaccgctgg      3000
tagcggtggt ttttttgttt gcaagcagca gattacgcgc agaaaaaaag gatctcaaga      3060
agatcctttg atcttttcta cggggtctga cgctcagtgg aacgaaaact cacgttaagg      3120
gattttggtc atgagattat caaaaaggat cttcacctag atccttttaa attaaaaatg      3180
aagttttaaa tcaatctaaa gtatatatga gtaaacttgg tctgacagtt accaatgctt      3240
aatcagtgag gcacctatct cagcgatctg tctatttcgt tcatccatag ttgcctgact      3300
ccccgtcgtg tagataacta cgatacggga gggcttacca tctggcccca gtgctgcaat      3360
gataccgcga cccacgct caccggctcc agatttatca gcaataaacc agccagccgg      3420
aagggccgag cgcagaagtg gtcctgcaac tttatccgcc tccatccagt ctattaattg      3480
ttgccgggaa gctagagtaa gtagttcgcc agttaatagt ttgcgcaacg ttgttgccat      3540
tgctacaggc atcgtggtgt cacgctcgtc gtttggtatg gcttcattca gctccggttc      3600
ccaacgatca aggcgagtta catgatcccc catgttgtgc aaaaaagcgg ttagctcct      3660
tcggtcctcc gatcgttgtc agaagtaagt tggccgcagt gttatcactc atggttatgg      3720
cagcactgca taattctctt actgtcatgc catccgtaag atgcttttct gtgactggtg      3780
agtactcaac caagtcattc tgagaatagt gtatgcggcg accgagttgc tcttgcccgg      3840
cgtcaatacg ggataatacc gcgccacata gcagaacttt aaaagtgctc atcattggaa      3900
aacgttcttc ggggcgaaaa ctctcaagga tcttaccgct gttgagatcc agttcgatgt      3960
aacccactcg tgcacccaac tgatcttcag catcttttac tttcaccagc gtttctgggt      4020
gagcaaaaac aggaaggcaa aatgccgcaa aaaagggaat aagggcgaca cggaaatgtt      4080
```

-continued

```
gaatactcat actcttcctt tttcaatatt attgaagcat ttatcagggt tattgtctca    4140
tgagcggata catatttgaa tgtatttaga aaaataaaca ataggggtt ccgcgcacat     4200 ttccccgaaa agtgccacct aaattgtaag cgttaatatt ttgttaaaat tcgcgttaaa    4260
tttttgttaa atcagctcat tttttaacca ataggccgaa atcggcaaaa tcccttataa    4320
atcaaaagaa tagaccgaga tagggttgag tgttgttcca gtttggaaca agagtccact    4380
attaaagaac gtggactcca acgtcaaagg gcgaaaaacc gtctatcagg gcgatggccc    4440
actacgtgaa ccatcaccct aatcaagttt ttgggtcg aggtgccgta aagcactaaa      4500
tcggaaccct aaagggagcc cccgatttag agcttgacgg ggaaagccgg cgaacgtggc    4560
gagaaaggaa gggaagaaag cgaaaggagc gggcgctagg gcgctggcaa gtgtagcggt    4620
cacgctgcgc gtaaccacca cacccgccgc gcttaatgcg ccgctacagg gcgcgtccca    4680
ttcgccattc aggctgcgca actgttggga agggcgatcg gtgcgggcct cttcgctatt    4740
acgccagctg gcgaaagggg gatgtgctgc aaggcgatta agttgggtaa cgccaggg tt   4800 ttcccagtca cgacgttgta aaacgacggc cagtgagcgc gcgtaatacg actcactata    4860
gggcgaattg gagctccacc gcggtggcgg ccgct                               4895
```

```
<210> SEQ ID NO 20
<211> LENGTH: 2622
<212> TYPE: DNA
<213> ORGANISM: Human cytomegalovirus
<220> FEATURE:
<221> NAME/KEY: sig_peptide
<222> LOCATION: (1)..(69)
<223> OTHER INFORMATION: gH peptide signal
<220> FEATURE:
<221> NAME/KEY: misc_feature
<222> LOCATION: (1)..(2622)
<223> OTHER INFORMATION: HCMV gH - HCMV gB TM/CTD Nucleotide Sequence
<220> FEATURE:
<221> NAME/KEY: misc_feature
<222> LOCATION: (2151)..(2622)
<223> OTHER INFORMATION: gB TM-CTD

<400> SEQUENCE: 20
```

```
atgcggccag gcctcccctc ctacctcatc gtcctcgccg tctgtctcct cagccaccta     60
ctttcgtcac gatatggcgc agaagccata tccgaaccgc tggacaaagc gtttcaccta    120
ctgctcaaca cctacgggag acccatccgc ttcctgcgtg aaaacaccac ccagtgtacc    180
tacaatagca gcctccgtaa cagcacggtc gtcagggaaa acgccatcag tttcaacttt    240
ttccaaagct ataatcaata ctatgtattc catatgcctc gatgtctttt tgcgggtcct    300
ctggcggagc agtttctgaa ccaggtagat ctgaccgaaa ccctggaaag ataccaacag    360
agacttaaca cttacgcgct ggtatccaaa gacctggcca gctaccgatc tttttcgcag    420
cagctaaagg cacaggacag cctaggtgaa cagcccacca ctgtgccacc acccattgac    480
ctgtcaatac ctcacgtttg gatgccaccg caaaccactc cacacggctg acagaatca    540 cataccacct caggactaca ccgaccacac tttaaccaga cctgtatcct ctttgatgga    600
cacgatctac tattcagcac cgtcacacct tgtttgcacc aaggcttta cctcatcgac    660 gaactacgtt acgttaaaat aacactgacc gaggacttct tcgtagttac ggtgtccata    720
gacgacgaca cacccatgct gcttatcttc ggccatcttc cacgcgtact ctttaaagcg    780
ccctatcaac gcgacaactt atactacga caaactgaaa aacacgagct cctggtgcta    840
gttaagaaag atcaactgaa ccgtcactct tatctcaaag accgggactt tcttgacgcc    900
```

| | |
|---|---|
| gcacttgact tcaactacct ggacctcagc gcactactac gtaacagctt tcaccgttac | 960 |
| gccgtggatg tactcaaaag cggtcgatgt cagatgctgg accgccgcac ggtagaaatg | 1020 |
| gccttcgcct acgcattagc actgttcgca gcagcccgac aagaagaggc cggcgcccaa | 1080 |
| gtctccgtcc cacgggccct agaccgccag gccgcactct acaaatacag aatttatg | 1140 |
| atcacctgcc tctcacaaac accaccacgc accacgttgc tgctgtatcc cacggccgtg | 1200 |
| gacctggcca acgagccct ttggacaccg aatcagatca ccgacatcac cagcctcgta | 1260 |
| cgcctggtct acatactctc taaacagaat cagcaacatc tcatccccca gtgggcacta | 1320 |
| cgacagatcg ccgactttgc cctaaaacta cacaaaacgc acctggcctc ttttctttca | 1380 |
| gccttcgcgc gtcaagaact ctacctcatg ggcagcctcg tccactccat gctagtacat | 1440 |
| acgacggaga gacgcgaaat cttcatcgta gaaacgggcc tctgttcatt agccgagcta | 1500 |
| tcacacttta cgcagttgct agctcatccg caccacgaat acctcagcga cctgtacaca | 1560 |
| ccctgttcca gtagcgggcg acgcgatcac tcgctcgaac gcctcacacg tctcttcccc | 1620 |
| gatgccaccg tccccactac cgttcccgcc gccctctcca tcctatctac catgcaacca | 1680 |
| agcacgctag aaaccttccc cgacctgttt tgtctgccgc tcggcgaatc cttctccgcg | 1740 |
| ctgaccgtct ccgaacacgt cagttatgtc gtaacaaacc agtacctgat caaaggtatc | 1800 |
| tcctaccctg tctccaccac cgtcgtaggc cagagcctca tcatcccca cggacagt | 1860 |
| caaactaaat gcgaactgac gcgcaacatg cataccacac acagcatcac agcggcgctc | 1920 |
| aacatttccc tagaaaactg cgccttttgc caaagcgccc tactagaata cgacgacacg | 1980 |
| caaggcgtca tcaacatcat gtacatgcac gactcggacg acgtcctttt cgccctggat | 2040 |
| ccctacaacg aagtggtggt ctcatctccg cgaactcact acctcatgct tttgaaaaac | 2100 |
| ggtacggtcc tagaagtaac tgacgtcgtc gtggacgcta ccgacagtcg tttcggagcc | 2160 |
| ttcaccatca tcctcgtggc catagccgtc gtcattatca tttatttgat ctatactcga | 2220 |
| cagcggcgtc tctgcatgca gccgctgcag aacctctttc cctatctggt gtccgccgac | 2280 |
| gggaccaccg tgacgtcggg caacaccaaa gacacgtcgt acaggctcc gccttcctac | 2340 |
| gaggaaagtg tttataattc tggtcgcaaa ggaccgggac caccgtcgtc tgatgcatcc | 2400 |
| acggcggctc cgccttacac caacgagcag gcttaccaga tgcttctggc cctggtccgt | 2460 |
| ctggacgcag agcagcgagc gcagcagaac ggtacagatt cttttggacgg acagactggc | 2520 |
| acgcaggaca agggacagaa gcccaacctg ctagaccgac tgcgacaccg caaaaacggc | 2580 |
| taccgacact tgaaagactc cgacgaagaa gagaacgtct ga | 2622 |

<210> SEQ ID NO 21
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence

<400> SEQUENCE: 21

| | |
|---|---|
| atgggacaga ccgtcacaac accctgagc ctgaccctgg acattggaa agacgtggag | 60 |
| aggatcgcac ataaccagag cgtggacgtg aagaaacgga gatgggtcac attctgcagt | 120 |
| gctgagtggc caactttaa tgtgggatgg ccccgagacg gcactttcaa cagggatctg | 180 |
| atacccagg tgaagatcaa ggtctttagc ccaggacctc acggacatcc agaccaggtg | 240 |
| ccttatatcg tcacctggga ggcactggcc ttcgatcccc ctccatgggt gaagccattt | 300 |

```
gtccacccaa aaccacctcc accactgcct ccaagtgccc cttcactgcc actggaacca    360
ccccggagca caccaccccg cagctccctg tatcctgctc tgactccatc tctgggcgca    420
aagccaaaac cacaggtgct gagcgactcc ggaggaccac tgattgacct gctgacagag    480 gacccccac cataccgaga tcctcggcct ccaccaagcg accgcgatgg aaatggagga     540
gaggctactc ctgccggcga agccctgac ccatctccaa tggctagtag gctgcgcggc     600
aggcgcgagc ctccagtggc agatagcacc acatcccagg ccttccctct gagggctggg    660
ggaaatgggc agctccagta ttggccattt tctagttcag acctgtacaa ctggaagaac    720
aataacccct ctttcagtga ggaccccggc aaactgaccg ccctgatcga atccgtgctg    780
attacccatc agcccacatg ggacgattgt cagcagctcc tgggcaccct gctgaccgga    840
gaggaaaagc agcgcgtgct gctggaggct cgcaaagcag tccgaggga cgatggacgg     900 cccacacagc tccctaatga ggtggacgcc gcttttccac tggaaagacc cgactgggat    960
tatactaccc aggcagggag aaaccacctg gtccattaca gcagctcct gctggcaggc   1020 ctgcagaatg ccgggagatc ccccaccaac ctggccaagg tgaaaggcat cacacagggg   1080
cctaatgagt caccaagcgc ctttctggag aggctgaagg aagcttaccg acggtatacc   1140 ccatcgacc ctgaggaccc cggacaggaa acaaacgtct ccatgtcttt catctggcag    1200
tctgccccag acattgggcg gaagctggag agactggaag acctgaagaa caagaccctg   1260
ggcgacctgg tgcgggaggc tgaaaagatc ttcaacaaac gggagacccc cgaggaaaga   1320
gaggaaagga ttagaaggga aactgaggaa aaggaggaac gccgacggac cgaggacgaa   1380
cagaaggaga agaacgaga tcggcggcgg caccgggaga tgtcaaagct gctggccacc   1440
gtggtcagcg acagaaaca ggacagacag ggaggagagc gacggagaag ccagctcgac   1500
agggatcagt gcgcatactg taaggaaaaa ggccattggg ccaaggattg ccccaaaaag   1560
ccaagaggac caagaggacc aagaccacag acatcactgc tgaccctgga cgac         1614

```

<210> SEQ ID NO 22
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65 nucleotide sequence

<400> SEQUENCE: 22

```
atgggacaga ccgtcacaac accctgagc ctgaccctgg acattggaa agacgtggag      60 aggatcgcac ataaccagag cgtggacgtg aagaaacgga gatgggtcac attctgcagt    120
gctgagtggc caacttttaa tgtgggatgg ccccgagacg gcactttcaa cagggatctg    180
atcacccagg tgaagatcaa ggtctttagc ccaggacctc acggacatcc agaccaggtg    240
ccttatatcg tcacctggga ggcactggcc ttcgatcccc ctccatgggt gaagccattt    300
gtccacccaa aaccacctcc accactgcct ccaagtgccc cttcactgcc actggaacca    360
ccccggagca caccaccccg cagctccctg tatcctgctc tgactccatc tctgggcgca    420
aagccaaaac cacaggtgct gagcgactcc ggaggaccac tgattgacct gctgacagag    480 gacccccac cataccgaga tcctcggcct ccaccaagcg accgcgatgg aaatggagga    540
```

```
gaggctactc ctgccggcga agcccctgac ccatctccaa tggctagtag gctgcgcggc      600
aggcgcgagc ctccagtggc agatagcacc acatcccagg ccttccctct gagggctggg      660
ggaaatgggc agctccagta ttggccattt tctagttcag acctgtacaa ctggaagaac      720
aataacccct ctttcagtga ggaccccggc aaactgaccg ccctgatcga atccgtgctg      780
attacccatc agcccacatg ggacgattgt cagcagctcc tgggcaccct gctgaccgga      840
gaggaaaagc agcgcgtgct gctggaggct cgcaaagcag tccgagggga cgatggacgg      900
cccacacagc tccctaatga ggtggacgcc gcttttccac tggaaagacc cgactgggat      960
tatactaccc aggcagggag aaaccacctg gtccattaca ggcagctcct gctggcaggc     1020
ctgcagaatg ccgggagatc ccccaccaac ctggccaagg tgaaaggcat cacacagggg     1080
cctaatgagt caccaagcgc ctttctggag aggctgaagg aagcttaccg acggtatacc     1140
ccatacgacc ctgaggaccc cggacaggaa acaaacgtct ccatgtcttt catctggcag     1200
tctgccccag acattgggcg gaagctggag agactggaag acctgaagaa caagaccctg     1260
ggcgacctgg tgcgggaggc tgaaaagatc ttcaacaaac gggagacccc cgaggaagaa     1320
gaggaaagga ttagaaggga aactgaggaa aaggaggaac gccgacggac cgaggacgaa     1380
cagaaggaga agaacgaga tcggcggcgg caccggagag tgtcaaagct gctggccacc     1440
gtggtcagcg gacagaaaca ggacagacag ggaggagagc gacggagaag ccagctcgac     1500
agggatcagt gcgcatactg taaggaaaaa ggccattggg ccaaggattg ccccaaaaag     1560
ccaagaggac caagaggacc aagaccacag acatcactgc tgaccctgga cgactgcgag     1620
agccggggcc ggcggtgccc agaaatgatc tctgtgctgg ggcccattag tggacatgtg     1680
ctgaaggccg tcttctccag gggagacacc cccgtgctgc ctcacgagac tcgactgctg     1740
cagaccggca tccatgtgcg ggtctcccag ccctctctga ttctggtgtc acagtataca     1800
ccagatagca ctccctgcca cagaggagac aatcagctcc aggtgcagca tacctacttt     1860
acaggctccg aggtcgaaaa cgtgtctgtc aatgtgcaca accctaccgg caggagcatc     1920
tgtcctagcc aggagccaat gagcatctac gtgtacgccc tgcctctgaa gatgctgaat     1980
atcccatcaa ttaacgtcca ccattaccct agcgcagccg aacggaagca cagacatctg     2040
ccagtggccg acgctgtcat ccatgccagc ggcaaacaga tgtggcaggc aagactgacc     2100
gtgtccgggc tggcctggac aaggcagcag aatcagtgga aggagcccga cgtgtactat     2160
accagcgcct tcgtgttccc taccaaagac gtggccctga catgtggt gtgcgcacat      2220
gagctggtgt gcagcatgga aaacactagg gccaccaaga tgcaggtcat cggcgatcag     2280
tatgtcaaag tgtacctgga gagttttgc gaagacgtgc catcagggaa gctgttcatg     2340
catgtgaccc tgggcagcga tgtcgaggaa gacctgacca tgacaagaaa tccacagccc     2400
tttatgagac cccacgagag gaatgggttc actgtgctgt gccccaagaa catgatcatt     2460
aagcctggaa aaatcagtca tattatgctg gatgtggcct ttacatcaca cgagcatttc     2520
ggactgctgt gccccaaatc catccctgga ctgagcattt ccggcaatct gctgatgaac     2580
ggccagcaga tcttcctgga agtgcaggcc atccgggaga ccgtcgaact gcgacagtat     2640
gacccagtgg ctgcactgtt cttttttcgac atcgacctgc tgctgcagcg aggaccacag     2700
tacagcgagc accctacttt tacctcccag tatcggattc aggggaagct ggagtacagg     2760
cacacctggg atcgccatga cgaaggagcc gctcaggggg acgatgacgt gtggacatct     2820
ggcagtgatt cagacgagga actggtgaca actgagcgaa aaaccccccg ggtgacagga     2880
ggaggggcaa tggcagggc cagcaccagc gcagggcgga agcgaaaaag cgccagcagc     2940
```

-continued

```
gccacagcat gtaccgccgg cgtgatgact agaggaaggc tgaaggccga gtctacagtc    3000
gctcccgagg aagatactga cgaggatagt gacaatgaaa tccacaaccc cgccgtgttc    3060
acctggccac cttggcaggc agggattctg gctcgcaacc tggtccccat ggtggcaacc    3120
gtccagggac agaatctgaa gtatcaggag tttttctggg atgctaacga catctaccgg    3180
atttttgcag agctggaagg cgtgtggcag ccagcagccc agcccaaacg acggagacat    3240
cgacaggacg ctctgccagg accttgtatc gccagcacac caaagaagca cagggctaa    3300
```

COMPOSITIONS AND METHODS FOR TREATMENT OF CYTOMEGALOVIRUS

CROSS REFERENCE TO RELATED APPLICATIONS

The present application is a continuation of U.S. application Ser. No. 15/683,355, filed Aug. 22, 2017, which is a continuation of U.S. application Ser. No. 14/357,423, filed May 9, 2014, which is the National Stage of International Application PCT/IB12/02854, filed Nov. 9, 2012, which claims the benefit of U.S. Provisional Application No. 61/558,800, filed Nov. 11, 2011, and of U.S. Provisional Application No. 61/654,157, filed Jun. 1, 2012, the contents of all of which are herein incorporated by reference in their entirety.

REFERENCE TO SEQUENCE LISTING

The specification includes a Sequence Listing in the form of an ASCII compliant text file named "2007801-0086 VBI-025-PC ST25.txt", which was created on May 2, 2013 and has a size of 98.8 KB, the contents of which are hereby incorporated by reference in their entirety.

BACKGROUND

Human cytomegalovirus (HCMV), a β-herpesvirus, is a ubiquitously occurring pathogen. In an immunocompetent person, HCMV infection is normally unnoticed, having at most mild and nonspecific symptoms. By contrast, certain risk groups, for example in immunosuppressed patients such as AIDS patients or transplant recipients, and after prenatal infection, HCMV infection has serious manifestations (Staras S A et al., 2006 Clin Infect Dis 43(9):1143-51; Hebart H et al., 2004 Hum Immunol 65(5):432-6; Rowshani A T et al., 2005 Transplantation 79(4):381-6). Existing therapies include the use of immunoglobulins and anti-viral agents such as ganciclovir and its derivatives, which are most effective when used prophylactically or very early during infection in at risk populations. However, existing therapies are characterized by significant toxicity and limited efficacy, especially for late-onset disease (Boeckh M., 2004 Pediatr Transplant 8(Suppl. 5):19-27; Limaye A P., 2004 Transplantation 78(9):1390-6), and they have not had an impact on congenital HCMV disease. Development of an effective vaccine to protect against HCMV disease is recognized as an important public health priority (Arvin A M et al., 2004 Clin Infect Dis 39(2):233-9).

SUMMARY

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral DNA and are non-infectious.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DEFINITIONS

Figure 1B:
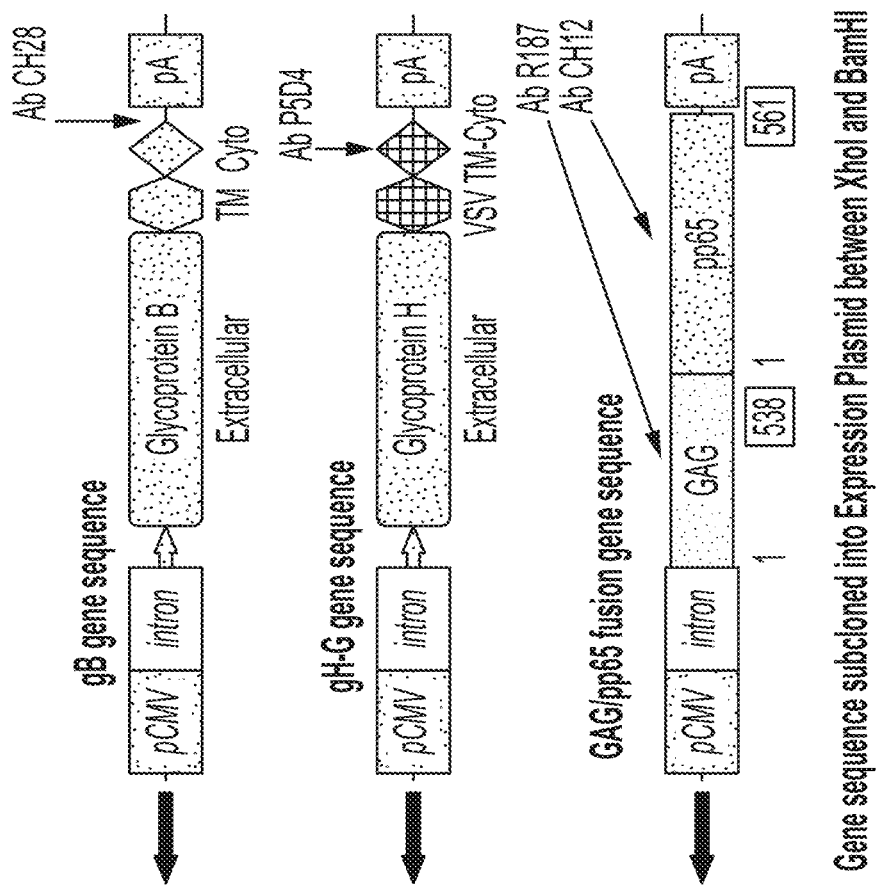
FIG. 1B shows construction of exemplary recombinant expression plasmids.

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antigen: As used herein, the term "antigen" refers to a substance containing one or more epitopes (either linear, conformational or both) that are recognized by antibodies. In certain embodiments, an antigen is or comprises a virus or a viral polypeptide. In some embodiments, the term "antigen" refers to a subunit antigen (i.e., an antigen which is separate and discrete from a whole virus with which the antigen is associated in nature; e.g., an antigen which is associated with a virus-like particle). Alternatively or additionally, in some embodiments, the term "antigen" refers to killed, attenuated or inactivated viruses. In certain embodiments, an antigen is an "immunogen."

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease, disorder or condition (e.g., HCMV infection). The term "prevention" refers to a delay of onset of a disease, disorder or condition. Prevention may be considered complete when onset of a disease, disorder or condition has been delayed for a predefined period of time.

Characteristic portion: As used herein, the term a "characteristic portion" of a substance, in the broadest sense, is one that shares a designated degree of structural identity with intact substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Cytoplasmic domain: As is known in the art, polypeptides sometimes have transmembrane, cytoplasmic, and/or extracellular domains. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localization (e.g., cytoplasmic localization). Exemplary such programs include psort (PSORT.org), Prosite (prosite.expasy.org), among others.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Extracellular domain: As is known in the art, polypeptides sometimes have transmembrane, cytoplasmic, and/or extracellular domains. In general, an "extracellular domain", as used herein, refers to a domain that has an attribute of being present outside a cell. As will be appreciated, it is not required that every amino acid in an extracellular domain be present outside the cell. For example, in some embodiments, an extracellular domain is characterized in that a designated stretch or portion of a protein is substantially located outside the cell. As is well known in the art, amino acid or nucleic acid sequences may be analyzed using a variety of algorithms to predict protein subcellular localization (e.g., extracellular localization). Exemplary such programs include psort (PSORT.org), Prosite (prosite.expasy.org), among others.

Fusion protein: As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Heterologous: As used herein, the term "heterologous" with respect to a protein or a polypeptide refers to a protein or polypeptide that is non-naturally occurring in a particular organism, such as a retrovirus or VLP. In some embodiments, a heterologous protein or polypeptide is non-naturally occurring in a particular retrovirus virion. As used herein, the term "heterologous" with respect to a protein domain generally refers to a protein domain that is non-naturally occurring in a particular protein.

Immunogenic: As used herein, the term "immunogenic" means capable of producing an immune response in a host animal against a non-host entity (e.g., an HCMV antigen). In certain embodiments, this immune response forms the basis of the protective immunity elicited by a vaccine against a specific infectious organism (e.g., an HCMV).

Immune response: As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein.

Individual, subject, patient: As used herein, the terms "subject," "individual" or "patient" refer to a human or a non-human mammalian subject. In some embodiments, the individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Linker: As used herein, the term "linker" refers to, e.g., in a fusion protein, an amino acid sequence of an appropriate length other than that appearing at a particular position in the natural protein and is generally designed to be flexible and/or to interpose a structure, such as an α-helix, between two protein moieties. In general, a linker allows two or more domains of a fusion protein to retain 50%, 55%, 60%, 65%, 70%, 75%, 80%, 85%, 90%, 95% or more of the biological activity of each of the domains. A linker may also be referred to as a spacer.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Polyprotein: As used herein, the term "polyprotein", generally refers to a protein that, after synthesis, may be cleaved to produce several functionally distinct polypeptides. A polyprotein is typically encoded by a single amino acid sequence. In some embodiments, an uncleaved polyprotein retains biological activity of its component parts. Some viruses produce such polyproteins, e.g., a Gag polyprotein, which can be retained as a functional polyprotein or can be processed into several functionally distinct polypeptides. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. In general, the form of the Gag protein that mediates viral particle assembly is the polyprotein.

Self-assembling portion: In general, a "self-assembling portion", as used herein, refers to a relevant stretch of an entity that adopts a defined arrangement without guidance or management from an outside source. In some embodiments, the entity is a protein. In some embodiments, the entity is a polyprotein. In some such embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. Self-assembly may be exhibited, for example, within the context of a cell (e.g., in vivo). Alternatively or additionally, self-assembly may be exhibited outside the context of a cell (e.g., in vitro). Self-assembly may be intramolecular (e.g., folding) and/or intermolecular. In some embodiments, self-assembly may be macromolecular whereby entities self-assemble into a complex and/or extended macromolecular structure. Self-assembled entities may exhibit a wide range of structural motifs, including, but not limited to particles, fibers, sheets, and ribbons. In some embodiments, self-assembly of an entity is important for a biological function of the entity. For example, in some embodiments, self assembly of a lipid leads to formation of a cell membrane structure. In some embodiments, self assembly of a protein (e.g., a viral structural protein) in a cellular context leads to formation of a particle structure (e.g., a viral particle structure). For example, a viral structural polyprotein may contain a targeting sequence that is capable of directing its localization to a cellular membrane of its host cell (e.g., plasma membrane, endosome, etc.) from which the viral structural polyprotein may bud out to form a VLP that contains host cellular membranous material surrounding the viral structural polyprotein.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology* 266:460-480 (1996); Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology* 266:460-480 (1996); Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., HCMV infection) has been diagnosed with and/or exhibits one or more symptoms of the disease, disorder, or condition.

Susceptible to: An individual who is "susceptible to" a disease, disorder, or condition (e.g., HCMV infection) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to HCMV).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" refers to an amount sufficient to confer a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular immunogenic composition, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific immunogenic composition employed; the duration of the treatment; and like factors as is well known in the medical arts.

Transmembrane domain: As is known in the art, polypeptides sometimes have transmembrane, cytoplasmic, and/or extracellular domains. In general, a "transmembrane domain", as used herein, refers to a domain having an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others.

Treatment: As used herein, the term "treatment" (also "treat" or "treating") refers to any administration of an immunogenic composition that partially or completely alleviates, ameliorates, relieves, inhibits, delays onset of, reduces severity of and/or reduces incidence of one or more symptoms or features of a particular disease, disorder, and/or condition (e.g., HCMV infection) or the predisposition toward the disease. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, the term "treating" refers to the vaccination of a patient.

Vaccination: As used herein, the term "vaccination" refers to the administration of a composition intended to generate an immune response, for example to a disease-causing agent (e.g., HCMV). For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiments, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF CERTAIN EMBODIMENTS

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral RNA or DNA and are non-infectious. In some embodiments, provided VLPs do contain viral RNA or DNA and are infectious. In some such embodiments, provided VLPs are useful as a DNA vaccine.

In some embodiments, the humoral immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 28 months, at least about 32 months, at least about 36 months, at least about 40 months, at least about 44 months, at least about 48 months, or longer. In some embodiments, the cellular immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least 12 months.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells (Tx) and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

I. Virus-Like Particles (VLPs)

Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genus Alpharetrovirus, Betaretrovirus, Gammearetrovirus, Deltaretrovirus, Epsilonretrovirus, Lentivirus and Spumavirus. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate enveloped virions that are infectious and either replication-competent or replication-defective. Replication-competent infectious retroviral vectors contain all of the necessary genes for virion synthesis and continue to propagate themselves once infection of the host cell occurs. Replication-defective infectious retroviral vectors do not spread after the initial infection. This is accomplished by replacement of most of the coding regions of the retrovirus with genes or nucleotide sequences to be transferred; so that the vector is incapable of making proteins required for additional rounds of replication.

Alternatively or additionally, retroviral vectors can be used to generate virus-like particles (VLPs) that lack a retrovirus-derived genome and are both non-infectious and non-replicating. Because of VLPs advantageous properties, VLPs may be utilized as an antigen delivery system. Furthermore, because VLPs are non-infectious, they can be administered safely as an immunogenic composition (e.g., a vaccine). VLPs are generally structurally similar to enveloped virions described above, but lack a retrovirus-derived genome, making it unlikely that viral replication will occur. Expression of capsid proteins (e.g., Gag) of some viruses (e.g., murine leukemia viruses, such as Moloney Murine leukemia virus (MMLV)) leads to self-assembly into particles similar to the corresponding native virus, which particles are free of viral genetic material.

A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein, as shown for VLPs prepared from hepadnaviruses (e.g., Engerix™ GSK and Recombivax HB™, Merck), papillomaviruses (e.g., Cervarix™, GSK and Gardasil™ Merck), paroviruses, or polyomaviruses. In some embodiments, VLPs are enveloped and can comprise multiple antigenic proteins found in the corresponding native virus. VLPs typically resemble their corresponding native virus and can be multivalent particulate structures. In some embodiments, antigenic proteins may be presented internally within the VLP, as a component of the VLP structure, and/or on the surface of the VLP. The present invention encompasses the recognition that presentation of an antigen in the context of a VLP is advantageous for induction of neutralizing antibodies against the antigen as compared to other forms of antigen presentation, e.g., soluble antigens not associated with a VLP. Neutralizing antibodies most often recognize tertiary or quarternary structures; this often requires presenting antigenic proteins, like envelope glycoproteins, in their native viral conformation. Alternatively or additionally, VLPs may be useful for presenting antigens in a context which induces cellular immunity (e.g., T cell response). The present invention further encompasses the insight that use of antigen combinations in VLP systems can generate improved immune response.

A. Structural Proteins

In some embodiments, the present invention utilizes VLPs comprised of one or more retroviral structural proteins (e.g., Gag). In some embodiments, a structural protein for use in accordance with the present invention is Alpharetrovirus (e.g., Avian Leukosis Virus), Betaretrovirus (Mouse Mammary Tumor Virus), Gammearetrovirus (Murine Leukemia Virus), Deltaretrovirus (Bovine Leukemia Virus), Epsilonretrovirus (Walley Dermal Sarcoma Virus), Lentivirus (Human Immunodeficiency Virus 1) or Spumavirus (Chimpanzee Foamy Virus) structural protein. In certain embodiments, a structural polyprotein is a Murine Leukemia Virus (MLV) structural protein. Genomes of these retroviruses are readily available in databases. The Gag genes of all these retroviruses have an overall structural similarity and within each group of retroviruses are conserved at the amino acid level. Retroviral Gag proteins primarily function in viral assembly. The Gag gene in the form of a polyprotein gives rise to the core structural proteins of the VLP. The MLV Gag gene encodes a 65 kDa polyprotein precursor which is proteolytically cleaved into 4 structural proteins (Matrix (MA); p12; Capsid (CA); and Nucleocapsid (NC)), by MLV protease, in the mature virion. Retroviruses assemble immature capsid composed of the Gag polyprotein formed from the Gag polypeptide but devoid of other viral elements like viral protease with Gag as the structural protein of the immature virus particle. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. The form of the Gag protein that mediates viral particle assembly is the polyprotein.

In some embodiments, a retroviral structural protein for use in accordance with the present invention is a Gag polypeptide. As used herein, the term "Gag polypeptide" is the retrovirus derived structural polypeptide that is responsible for formation of the VLPs described herein and refers to a polypeptide sequence whose amino acid sequence includes at least one characteristic sequence of Gag. A wide variety of Gag sequences from various retroviruses are known in the art and those of ordinary skill in the art, referring to such sequences, can readily identify sequences that are characteristic of Gag proteins generally, and/or of particular Gag polypeptides.

An exemplary Gag polypeptide for use in accordance with the present invention is shown as SEQ ID NO:1 below. In some embodiments, a suitable Gag polypeptide is substantially homologous to a known retroviral Gag polypeptide. For example, a Gag polypeptide may be a modified retroviral Gag polypeptide containing one or more amino acid substitutions, deletions, and/or insertions as compared to a wild-type or naturally-occurring Gag polypeptide (e.g., SEQ ID NO:1), while retaining substantial self-assembly activity. Thus, in some embodiments, a Gag polypeptide suitable for the present invention is substantially homologous to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Gag polypeptide suitable for the present invention is substantially identical to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

```
MMLV Gag Amino Acid Sequence
                                    (SEQ ID NO: 1)
MGQTVTTPLSLTLGHWKDVERIAHNQSVDVKKRRWVTFCS

AEWPTFNVGWPRDGTFNEPPRSTPPRSSLYPALTPSLGAK

PKPQVLSDSGGPLIDLLTEDPPPYRDPRPPPSDRDGNGGE

ATPAGEAPDPSPMASRLRGRREPPVADSTTSQAFPLRAGG

NGQLQYWPFSSSDLYNWKNNNPSFSEDPGKLTALIESVLI

THQPTWDDCQQLLGTLLTGEEKQRVLLEARKAVRGDDGRP

TQLPNEVDAAFPLERPDWDYTTQAGRNHLVHYRQLLLAGL

QNAGRSPTNLAKVKGITQGPNESPSAFLERLKEAYRRYTP

YDPEDPGQETNVSMSFIWQSAPDIGRKLERLEDLKNKTLG

DLVREAEKIFNKRETPEEREERIRRETEEKEERRRTEDEQ

KEKERDRRRHREMSKLLATVVSGQKQDRQGGERRRSQLDR

DQCAYCKEKGHWAKDCPKKPRGPRGPRPQTSLLTLDD
(SEQ ID NO: 1)

MMLV Gag Nucleotide Sequence
                                    (SEQ ID NO: 2)
ATGGGCCAGACTGTTACCACTCCCTTAAGTTTGACCTTAG

GTCACTGGAAAGATGTCGAGCGGATCGCTCACAACCAGTC

GGTAGATGTCAAGAAGAGACGTTGGGTTACCTTCTGCTCT

GCAGAATGGCCAACCTTTAACGTCGGATGGCCGCGAGACG

GCACCTTTAACCGAGACCTCATCACCCAGGTTAAGATCAA

GGTCTTTTCACCTGGCCCGCATGGACACCCAGACCAGGTC

CCCTACATCGTGACCTGGGAAGCCTTGGCTTTTGACCCCC

CTCCCTGGGTCAAGCCCTTTGTACACCCTAAGCCTCCGCC

TCCTCTTCCTCCATCCGCCCCGTCTCTCCCCCTTGAACCT

CCTCGTTCGACCCCGCCTCGATCCTCCCTTTATCCAGCCC

TCACTCCTTCTCTAGGCGCCAAACCTAAACCTCAAGTTCT

TTCTGACAGTGGGGGGCCGCTCATCGACCTACTTACAGAA

GACCCCCCGCCTTATAGGGACCCAAGACCACCCCCTTCCG

ACAGGGACGGAAATGGTGGAGAAGCGACCCCTGCGGGAGA

GGCACCGGACCCCTCCCCAATGGCATCTCGCCTACGTGGG

AGACGGAGCCCCCTGTGGCCGACTCCACTACCTCGCAGG

CATTCCCCCTCCGCGCAGGAGGAAACGGACAGCTTCAATA

CTGGCCGTTCTCCTCTTCTGACCTTTACAACTGGAAAAAT

AATAACCCTTCTTTTTCTGAAGATCCAGGTAAACTGACAG

CTCTGATCGAGTCTGTTCTCATCACCCATCAGCCCACCTG

GGACGACTGTCAGCAGCTGTTGGGGACTCTGCTGACCGGA

GAAGAAAACAACGGGTGCTCTTAGAGGCTAGAAAGGCGG

TGCGGGGCGATGATGGGCGCCCCACTCAACTGCCCAATGA

AGTCGATGCCGCTTTTCCCCTCGAGCGCCCAGACTGGGAT

TACACCACCCAGGCAGGTAGGAACCACCTAGTCCACTATC

GCCAGTTGCTCCTAGCGGGTCTCCAAAACGCGGGCAGAAG

CCCCACCAATTTGGCCAAGGTAAAAGGAATAACACAAGGG

CCCAATGAGTCTCCCTCGGCCTTCCTAGAGAGACTTAAGG

AAGCCTATCGCAGGTACACTCCTTATGACCCTGAGGACCC

AGGGCAAGAAACTAATGTGTCTATGTCTTTCATTTGGCAG

TCTGCCCCAGACATTGGGAGAAAGTTAGAGAGGTTAGAAG

ATTTAAAAAACAAGACGCTTGGAGATTTGGTTAGAGAGGC

AGAAAAGATCTTTAATAAACGAGAAACCCCGGAAGAAAGA

GAGGAACGTATCAGGAGAGAAACAGAGGAAAAAGAAGAAC

GCCGTAGGACAGAGGATGAGCAGAAAGAGAAAGAAAGAGA

TCGTAGGAGACATAGAGAGATGAGCAAGCTATTGGCCACT

GTCGTTAGTGGACAGAAACAGGATAGACAGGGAGGAGAAC

GAAGGAGGTCCCAACTCGATCGCGACCAGTGTGCCTACTG

CAAAGAAAGGGGCACTGGGCTAAAGATTGTCCCAAGAAA

CCACGAGGACCTCGGGGACCAAGACCCCAGACCTCCCTCC

TGACCCTAGATGAC
(SEQ ID NO: 2)

Codon Optimized MMLV Gag Nucleotide
Sequence
                                    (SEQ ID NO: 3)
ATGGGACAGACAGTCACTACACCCCTGAGCCTGACACTGG

GACATTGGAAAGACGTGGAGAGGATTGCACATAACCAGAG

CGTGGACGTGAAGAAACGGAGATGGGTCACCTTTTGCTCC

GCCGAGTGGCCAACATTCAATGTGGGATGGCCCCGAGATG

GCACCTTCAACCGGGACCTGATCACTCAGGTGAAGATCAA

GGTCTTCTCTCCAGGACCCCACGGCCATCCAGATCAGGTG

CCCTACATCGTCACCTGGGAGGCTCTGGCATTTGACCCCC

CTCCATGGGTGAAGCCTTTCGTCCACCCAAAACCACCTCC

ACCACTGCCTCCATCTGCCCCTAGTCTGCCACTGGAACCC

CCTCGGTCAACCCCACCCAGAAGCTCCCTGTATCCCGCAC
```

```
TGACACCTAGCCTGGGGGCCAAGCCTAAACCACAGGTGCT
GTCTGATAGTGGCGGGCCTCTGATCGATCTGCTGACCGAG
GACCCTCCACCATACCGCGACCCACGACCTCCACCAAGCG
ACCGGGACGGAAACGGAGGAGAGGCTACACCCGCAGGCGA
AGCCCCCGATCCTAGTCCAATGGCATCAAGGCTGCGCGGG
AGGCGCGAACCTCCAGTGGCCGACTCAACCACAAGCCAGG
CATTTCCACTGAGGGCCGGGGGAAATGGACAGCTCCAGTA
TTGGCCCTTCTCTAGTTCAGATCTGTACAACTGGAAGAAC
AATAACCCTAGCTTCAGCGAGGACCCAGGCAAACTGACCG
CCCTGATCGAATCCGTGCTGATTACCCACCAGCCCACATG
GGACGATTGTCAGCAGCTCCTGGGCACCCTGCTGACCGGA
GAGGAAAAGCAGAGAGTGCTGCTGGAGGCTAGGAAAGCAG
TCCGCGGGGACGATGGAAGGCCAACACAGCTCCCCAATGA
GGTGGATGCCGCTTTCCCTCTGGAACGGCCAGATTGGGAC
TATACTACCCAGGCTGGACGCAACCACCTGGTGCATTACC
GGCAGCTCCTGCTGGCTGGACTGCAGAATGCAGGGCGCAG
CCCCACTAACCTGGCCAAGGTGAAAGGAATCACCCAGGGC
CCCAATGAGTCCCCTTCTGCATTCCTGGAGCGGCTGAAGG
AAGCCTACCGACGGTATACTCCCTACGATCCTGAGGACCC
AGGCCAGGAAACCAACGTGAGTATGAGCTTCATCTGGCAG
TCCGCTCCTGACATTGGCCGAAAACTGGAGCGGCTGGAAG
ATCTGAAGAACAAGACCCTGGGCGACCTGGTGCGGGAGGC
AGAAAAGATCTTCAACAAAAGGGAGACTCCAGAGGAACGG
GAGGAAAGAATTAGAAGGGAAACAGAGGAAAAGGAGGAAC
GCCGACGGACTGAGGATGAACAGAAGGAGAAAGAAAGAGA
CCGGCGGCGGCACCGGGAGATGTCTAAGCTGCTGGCCACC
GTGGTCAGTGGCCAGAAACAGGATCGACAGGGAGGAGAGC
GACGGAGAAGCCAGCTCGATCGGGACCAGTGCGCCTATTG
TAAGGAAAAGGGCATTGGGCTAAGGACTGCCCCAAGAAA
CCCAGAGGCCCACGCGGGCCCCGACCTCAGACTTCCCTGC
TGACCCTGGACGAT
(SEQ ID NO: 3)

Codon Optimized MMLV Gag Nucleotide
Sequence
                              (SEQ ID NO: 21)
ATGGGACAGACCGTCACAACACCCCTGAGCCTGACCCTGG
GACATTGGAAAGACGTGGAGAGGATCGCACATAACCAGAG
CGTGGACGTGAAGAAACGGAGATGGGTCACATTCTGCAGT
GCTGAGTGGCCAACTTTTAATGTGGGATGGCCCCGAGACG
GCACTTTCAACAGGGATCTGATCACCCAGGTGAAGATCAA
GGTCTTTAGCCCAGGACCTCACGGACATCCAGACCAGGTG
CCTTATATCGTCACCTGGGAGGCACTGGCCTTCGATCCCC
```
```
CTCCATGGGTGAAGCCATTTGTCCACCCAAAACCACCTCC
ACCACTGCCTCCAAGTGCCCCTTCACTGCCACTGGAACCA
CCCCGGAGCACACCACCCCGCAGCTCCCTGTATCCTGCTC
TGACTCCATCTCTGGGCGCAAAGCCAAAACCACAGGTGCT
GAGCGACTCCGGAGGACCACTGATTGACCTGCTGACAGAG
GACCCCCCACCATACCGAGATCCTCGGCCTCCACCAAGCG
ACCGCGATGGAAATGGAGGAGAGGCTACTCCTGCCGGCGA
AGCCCCTGACCCATCTCCAATGGCTAGTAGGCTGCGCGGC
AGGCGCGAGCCTCCAGTGGCAGATAGCACCACATCCCAGG
CCTTCCCTCTGAGGGCTGGGGGAAATGGGCAGCTCCAGTA
TTGGCCATTTTCTAGTTCAGACCTGTACAACTGGAAGAAC
AATAACCCCTCTTTCAGTGAGGACCCCGGCAAACTGACCG
CCCTGATCGAATCCGTGCTGATTACCCATCAGCCCACATG
GGACGATTGTCAGCAGCTCCTGGGCACCCTGCTGACCGGA
GAGGAAAAGCAGCGCGTGCTGCTGGAGGCTCGCAAAGCAG
TCCGAGGGGACGATGGACGGCCCACACAGCTCCCTAATGA
GGTGGACGCCGCTTTTCCACTGGAAAGACCCGACTGGGAT
TATACTACCCAGGCAGGGAGAAACCACCTGGTCCATTACA
GGCAGCTCCTGCTGGCAGGCCTGCAGAATGCCGGGAGATC
CCCCACCAACCTGGCCAAGGTGAAAGGCATCACACAGGGG
CCTAATGAGTCACCAAGCGCCTTTCTGGAGAGGCTGAAGG
AAGCTTACCGACGGTATACCCCATACGACCCTGAGGACCC
CGGACAGGAAACAAACGTCTCCATGTCTTTCATCTGGCAG
TCTGCCCCAGACATTGGGCGGAAGCTGGAGAGACTGGAAG
ACCTGAAGAACAAGACCCTGGGCGACCTGGTGCGGGAGGC
TGAAAAGATCTTCAACAAACGGGAGACCCCCGAGGAAAGA
GAGGAAAGGATTAGAAGGGAAACTGAGGAAAAGGAGGAAC
GCCGACGGACCGAGGACGAACAGAAGGAGAAAGAACGAGA
TCGGCGGCGGCACCGGGAGATGTCAAAGCTGCTGGCCACC
GTGGTCAGCGGACAGAAACAGGACAGACAGGGAGGAGAGC
GACGGAGAAGCCAGCTCGACAGGGATCAGTGCGCATACTG
TAAGGAAAAAGGCCATTGGGCCAAGGATTGCCCCAAAAAG
CCAAGAGGACCAAGAGGACCAAGACCACAGACATCACTGC
TGACCCTGGACGAC
(SEQ ID NO: 21)
```

Typically in nature, a Gag protein includes a large C-terminal extension which may contain retroviral protease, reverse transcriptase, and integrase enzymatic activity. Assembly of VLPs, however, generally does not require the presence of such components. In some cases, a retroviral Gag protein alone (e.g., lacking a C-terminal extension, lacking one or more of genomic RNA, reverse transcriptase, viral protease, or envelope protein) can self-assemble to form VLPs both in vitro and in vivo (Sharma S et al., 1997 Proc. Natl. Acad. Sci. USA 94: 10803-8). Retroviral Gag polyprotein alone can oligomerize and assemble into VLPs.

In some embodiments, a Gag polypeptide for use in accordance with the present invention lacks a C-terminal extension and/or contains a modified C-terminal extension. A Gag polypeptide may optionally include one or more additional polypeptides (e.g., a heterologous antigen). In some embodiments, a Gag polypeptide is co-expressed with a heterologous antigen (e.g., under separate promoters and/or as separate proteins). In some embodiments, a Gag polypeptide is expressed as a fusion protein with a heterologous antigen. The Gag polypeptide can be linked to a heterologous antigen to create a fusion protein without altering Gag function. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen creates a fusion protein that acts as unmodified Gag and as a result will allow the antigen to be incorporated into the structural components of a resulting VLP. In some embodiments, VLP structural components serve as effective immunogens (e.g., for induction of cellular immune response). For example, provided VLPs may comprise a retroviral Gag polypeptide (e.g., MMLV Gag) and a structural component of HCMV (e.g., pp65). In some such embodiments, pp65 is incorporated into the VLP and serves as an antigen for eliciting an immune response against HCMV.

An exemplary Gag-pp65 fusion polypeptide for use in accordance with the present invention is shown as SEQ ID NO:4 below. In some embodiments, a suitable Gag polypeptide fusion protein includes all or a portion of a Gag polypeptide that is substantially homologous to a known retroviral Gag polypeptide and all or a portion of a pp65 polypeptide that is substantially homologous to a known pp65 polypeptide. For example, a Gag-pp65 polypeptide fusion protein may contain one or more amino acid substitutions, deletions, and/or insertions as compared to a wild-type or naturally-occurring Gag polypeptide and/or pp65 polypeptide, while retaining substantial self-assembly activity. Thus, in some embodiments, a Gag-pp65 polypeptide fusion protein suitable for the present invention is substantially homologous to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a Gag-pp65 polypeptide fusion protein suitable for the present invention is substantially identical to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4.

```
MMLV Gag-CMV pp65 Amino Acid Sequence
                                       (SEQ ID NO: 4)
MGQTVTTPLSLTLGHWKDVERIAHNQSVDVKKRRWVTFCS AEWPTFNVGWPRDGTFNRDLITQVKIKVFSPGPHGHPDQV
```
-continued
```
PYIVTWEALAFDPPPWVKPFVHPKPPPPLPPSAPSLPLEP

PRSTPPRSSLYPALTPSLGAKPKPQVLSDSGGPLIDLLTE

DPPPYRDPRPPPSDRDGNGGEATPAGEAPDPSPMASRLRG

RREPPVADSTTSQAFPLRAGGNGQLQYWPFSSSDLYNWKN

NNPSFSEDPGKLTALIESVLITHQPTWDDCQQLLGTLLTG

EEKQRVLLEARKAVRGDDGRPTQLPNEVDAAFPLERPDWD

YTTQAGRNHLVHYRQLLLAGLQNAGRSPTNLAKVKGITQG

PNESPSAFLERLKEAYRRYTPYDPEDPGQETNVSMSFIWQ

SAPDIGRKLERLEDLKNKTLGDLVREAEKIFNKRETPEER

EERIRRETEEKEERRRTEDEQKEKERDRRRHREMSKLLAT

VVSGQKQDRQGGERRRSQLDRDQCAYCKEKGHWAKDCPKK

PRGPRGPRPQTSLLTLDDCESRGRRCPEMISVLGPISGHV

LKAVFSRGDTPVLPHETRLLQTGIHVRVSQPSLILVSQYT

PDSTPCHRGDNQLQVQHTYFTGSEVENVSVNVHNPTGRSI

CPSQEPMSIYVYALPLKMLNIPSINVHHYPSAAERKHRHL

PVADAVIHASGKQMWQARLTVSGLAWTRQQNQWKEPDVYY

TSAFVFPTKDVALRHVVCAHELVCSMENTRATKMQVIGDQ

YVKVYLESFCEDVPSGKLFMHVTLGSDVEEDLTMTRNPQP

FMRPHERNGFTVLCPKNMIIKPGKISHIMLDVAFTSHEHF

GLLCPKSIPGLSISGNLLMNGQQIFLEVQAIRETVELRQY

DPVAALFFFDIDLLLQRGPQYSEHPTFTSQYRIQGKLEYR

HTWDRHDEGAAQGDDDVWTSGSDSDEELVTTERKTPRVTG

GGAMAGASTSAGRKRKSASSATACTAGVMTRGRLKAESTV

APEEDTDEDSDNEIHNPAVFTWPPWQAGILARNLVPMVAT

VQGQNLKYQEFFWDANDIYRIFAELEGVWQPAAQPKRRRH

RQDALPGPCIASTPKKHRG*
(SEQ ID NO: 4)
(MMLV Gag amino acid sequence bolded)

MMLV Gag-CMV pp65 Nucleotide Sequence
                                       (SEQ ID NO: 5)
ATGGGCCAGACTGTTACCACTCCCTTAAGTTTGACCTTAG

GTCACTGGAAAGATGTCGAGCGGATCGCTCACAACCAGTC

GGTAGATGTCAAGAAGAGACGTTGGGTTACCTTCTGCTCT

GCAGAATGGCCAACCTTTAACGTCGGATGGCCGCGAGACG

GCACCTTTAACCGAGACCTCATCACCCAGGTTAAGATCAA

GGTCTTTTCACCTGGCCCGCATGGACACCCAGACCAGGTC

CCCTACATCGTGACCTGGGAAGCCTTGGCTTTTGACCCCC

CTCCCTGGGTCAAGCCCTTTGTACACCCTAAGCCTCCGCC

TCCTCTTCCTCCATCCGCCCCGTCTCTCCCCCTTGAACCT

CCTCGTTCGACCCCGCCTCGATCCTCCCTTTATCCAGCCC

TCACTCCTTCTCTAGGCGCCAAACCTAAACCTCAAGTTCT
```

-continued

TTCTGACAGTGGGGGGCCGCTCATCGACCTACTTACAGAA
GACCCCCGCCTTATAGGGACCCAAGACCACCCCCTTCCG
ACAGGGACGGAAATGGTGGAGAAGCGACCCCTGCGGAGA
GGCACCGGACCCCTCCCCAATGGCATCTCGCCTACGTGGG
AGACGGGAGCCCCTGTGGCCGACTCCACTACCTCGCAGG
CATTCCCCCTCCGCGCAGGAGGAAACGGACAGCTTCAATA
CTGGCCGTTCTCCTCTTCTGACCTTTACAACTGGAAAAAT
AATAACCCTTCTTTTTCTGAAGATCCAGGTAAACTGACAG
CTCTGATCGAGTCTGTTCTCATCACCCATCAGCCCACCTG
GGACGACTGTCAGCAGCTGTTGGGACTCTGCTGACCGGA
GAAGAAAAACAACGGGTGCTCTTAGAGGCTAGAAAGGCGG
TGCGGGGCGATGATGGGCGCCCCACTCAACTGCCCAATGA
AGTCGATGCCGCTTTTCCCCTCGAGCGCCCAGACTGGGAT
TACACCACCCAGGCAGGTAGGAACCACCTAGTCCACTATC
GCCAGTTGCTCCTAGCGGGTCTCCAAAACGCGGGCAGAAG
CCCCACCAATTTGGCCAAGGTAAAAGGAATAACACAAGGG
CCCAATGAGTCTCCCTCGGCCTTCCTAGAGAGACTTAAGG
AAGCCTATCGCAGGTACACTCCTTATGACCCTGAGGACCC
AGGGCAAGAAACTAATGTGTCTATGTCTTTCATTTGGCAG
TCTGCCCCAGACATTGGGAGAAAGTTAGAGAGGTTAGAAG
ATTTAAAAAACAAGACGCTTGGAGATTTGGTTAGAGAGGC
AGAAAAGATCTTTAATAAACGAGAAACCCCGGAAGAAAGA
GAGGAACGTATCAGGAGAGAAACAGAGGAAAAAGAAGAAC
GCCGTAGGACAGAGGATGAGCAGAAAGAGAAAGAAAGAGA
TCGTAGGAGACATAGAGAGATGAGCAAGCTATTGGCCACT
GTCGTTAGTGGACAGAAACAGGATAGACAGGGAGGAGAAC
GAAGGAGGTCCCAACTCGATCGCGACCAGTGTGCCTACTG
CAAAGAAAAGGGGCACTGGGCTAAAGATTGTCCCAAGAAA
CCACGAGGACCTCGGGGACCAAGACCCCAGACCTCCCTCC
TGACCCTAGATGACTGTGAGTCGCGCGGTCGCCGTTGTCC
CGAAATGATATCCGTACTGGGTCCCATTTCGGGGCACGTG
CTGAAAGCCGTGTTTAGTCGCGGCGACACGCCGGTGCTGC
CGCACGAGACGCGACTCCTGCAGACGGGTATCCACGTGCG
CGTGAGCCAGCCCTCGCTGATCCTGGTGTCGCAGTACACG
CCCGACTCGACGCCATGCCACCGCGGCGACAATCAGCTGC
AGGTGCAGCACACGTACTTTACGGGCAGCGAGGTGGAGAA
CGTGTCGGTCAACGTGCACAACCCCACGGGCCGGAGCATC
TGCCCCAGCCAAGAGCCCATGTCGATCTATGTGTACGCGC
TGCCGCTCAAGATGCTGAACATCCCCAGCATCAACGTGCA
CCACTACCCGTCGGCGGCCGAGCGCAAACACCGACACCTG
CCCGTAGCTGACGCTGTGATTCACGCGTCGGGCAAGCAGA

-continued

TGTGGCAGGCGCGTCTCACGGTCTCGGGACTGGCCTGGAC
GCGTCAGCAGAACCAGTGGAAAGAGCCCGACGTCTACTAC
ACGTCAGCGTTCGTGTTTCCCACCAAGGACGTGGCACTGC
GGCACGTGGTGTGCGCGCACGAGCTGGTTTGCTCCATGGA
GAACACGCGCGCAACCAAGATGCAGGTGATAGGTGACCAG
TACGTCAAGGTGTACCTGGAGTCCTTCTGCGAGGACGTGC
CCTCCGGCAAGCTCTTTATGCACGTCACGCTGGGCTCTGA
CGTGGAAGAGGACCTGACGATGACCCGCAACCCGCAACCC
TTCATGCGCCCCCACGAGCGCAACGGCTTTACGGTGTTGT
GTCCCAAAAATATGATAATCAAACCGGGCAAGATCTCGCA
CATCATGCTGGATGTGGCTTTTACCTCACACGAGCATTTT
GGGCTGCTGTGTCCCAAGAGCATCCCGGGCCTGAGCATCT
CAGGTAACCTATTGATGAACGGGCAGCAGATCTTCCTGGA
GGTGCAAGCGATACGCGAGACCGTGGAACTGCGTCAGTAC
GATCCCGTGGCTGCGCTCTTCTTTTTCGATATCGACTTGC
TGCTGCAGCGCGGGCCTCAGTACAGCGAACACCCCACCTT
CACCAGCCAGTATCGCATCCAGGGCAAGCTTGAGTACCGA
CACACCTGGGACCGGCACGACGAGGGTGCCGCCCAGGGCG
ACGACGACGTCTGGACCAGCGGATCGGACTCCGACGAGGA
ACTCGTAACCACCGAGCGCAAGACGCCCCGCGTTACCGGC
GGCGGCGCCATGGCGGGCGCCTCCACTTCCGCGGGCCGCA
AACGCAAATCAGCATCCTCGGCGACGGCGTGCACGGCGGG
CGTTATGACACGCGGCCGCCTTAAGGCCGAGTCCACCGTC
GCGCCCGAAGAGGACACCGACGAGGATTCCGACAACGAAA
TCCACAATCCGGCCGTGTTCACCTGGCCGCCCTGGCAGGC
CGGCATCCTGGCCCGCAACCTGGTGCCCATGGTGGCTACG
GTTCAGGGTCAGAATCTGAAGTACCAGGAGTTCTTCTGGG
ACGCCAACGACATCTACCGCATCTTCGCCGAATTGGAAGG
CGTATGGCAGCCCGCTGCGCAACCCAAACGTCGCCGCCAC
CGGCAAGACGCCTTGCCCGGGCCATGCATCGCCTCGACGC
CCAAAAAGCACCGAGGTTAG
(SEQ ID NO: 5)
(MMLV Gag nucleotide sequence bolded)

Codon Optimized MMLV Gag-CMV pp65
Nucleotide Sequence
(SEQ ID NO: 6)
ATGGGACAGACAGTCACTACACCCCTGAGCCTGACACTGG
GACATTGGAAAGACGTGGAGAGGATTGCACATAACCAGAG
CGTGGACGTGAAGAAACGGAGATGGGTCACCTTTTGCTCC
GCCGAGTGGCCAACATTCAATGTGGGATGGCCCCGAGATG
GCACCTTCAACCGGGACCTGATCACTCAGGTGAAGATCAA
GGTCTTCTCTCCAGGACCCCACGGCCATCCAGATCAGGTG
CCCTACATCGTCACCTGGGAGGCTCTGGCATTTGACCCCC

-continued

CTCCATGGGTGAAGCCTTTCGTCCACCCAAAACCACCTCC

ACCACTGCCTCCATCTGCCCCTAGTCTGCCACTGGAACCC

CCTCGGTCAACCCCACCCAGAAGCTCCCTGTATCCCGCAC

TGACACCTAGCCTGGGGGCCAAGCCTAAACCACAGGTGCT

GTCTGATAGTGGCGGGCCTCTGATCGATCTGCTGACCGAG

GACCCTCCACCATACCGCGACCCACGACCTCCACCAAGCG

ACCGGGACGGAAACGGAGGAGAGGCTACACCCGCAGGCGA

AGCCCCCGATCCTAGTCCAATGGCATCAAGGCTGCGCGGG

AGGCGCGAACCTCCAGTGGCCGACTCAACCACAAGCCAGG

CATTTCCACTGAGGGCCGGGGGAAATGGACAGCTCCAGTA

TTGGCCCTTCTCTAGTTCAGATCTGTACAACTGGAAGAAC

AATAACCCTAGCTTCAGCGAGGACCCAGGCAAACTGACCG

CCCTGATCGAATCCGTGCTGATTACCCACCAGCCCACATG

GGACGATTGTCAGCAGCTCCTGGGCACCCTGCTGACCGGA

GAGGAAAAGCAGAGAGTGCTGCTGGAGGCTAGGAAAGCAG

TCCGCGGGGACGATGGAAGGCCAACACAGCTCCCCAATGA

GGTGGATGCCGCTTTCCCTCTGGAACGGCCAGATTGGGAC

TATACTACCCAGGCTGGACGCAACCACCTGGTGCATTACC

GGCAGCTCCTGCTGGCTGGACTGCAGAATGCAGGGCGCAG

CCCCACTAACCTGGCCAAGGTGAAAGGAATCACCCAGGGC

CCCAATGAGTCCCCTTCTGCATTCCTGGAGCGGCTGAAGG

AAGCCTACCGACGGTATACTCCCTACGATCCTGAGGACCC

AGGCCAGGAAACCAACGTGAGTATGAGCTTCATCTGGCAG

TCCGCTCCTGACATTGGCCGAAAACTGGAGCGGCTGGAAG

ATCTGAAGAACAAGACCCTGGGCGACCTGGTGCGGGAGGC

AGAAAAGATCTTCAACAAAAGGGAGACTCCAGAGGAACGG

GAGGAAAGAATTAGAAGGGAAACAGAGGAAAAGGAGGAAC

GCCGACGGACTGAGGATGAACAGAAGGAGAAAGAAAGAGA

CCGGCGGCGGCACCGGGAGATGTCTAAGCTGCTGGCCACC

GTGGTCAGTGGCCAGAAACAGGATCGACAGGGAGGAGAGC

GACGGAGAAGCCAGCTCGATCGGGACCAGTGCGCCTATTG

TAAGGAAAAGGGCATTGGGCTAAGGACTGCCCCAAGAAA

CCCAGAGGCCCACGCGGGCCCCGACCTCAGACTTCCCTGC

TGACCCTGGACGATTGCGAGAGCCGGGGCCGGCGGTGCCC

AGAAATGATCTCTGTGCTGGGGCCCATTAGTGGACATGTG

CTGAAGGCCGTCTTCTCCAGGGGAGACACCCCCGTGCTGC

CTCACGAGACTCGACTGCTGCAGACCGGCATCCATGTGCG

GGTCTCCCAGCCCTCTCTGATTCTGGTGTCACAGTATACA

CCAGATAGCACTCCCTGCCACAGAGGAGACAATCAGCTCC

AGGTGCAGCATACCTACTTTACAGGCTCCGAGGTCGAAAA

-continued

CGTGTCTGTCAATGTGCACAACCCTACCGGCAGGAGCATC

TGTCCTAGCCAGGAGCCAATGAGCATCTACGTGTACGCCC

TGCCTCTGAAGATGCTGAATATCCCATCAATTAACGTCCA

CCATTACCCTAGCGCAGCCGAACGGAAGCACAGACATCTG

CCAGTGGCCGACGCTGTCATCCATGCCAGCGGCAAACAGA

TGTGGCAGGCAAGACTGACCGTGTCCGGGCTGGCCTGGAC

AAGGCAGCAGAATCAGTGGAAGGAGCCCGACGTGTACTAT

ACCAGCGCCTTCGTGTTCCCTACCAAAGACGTGGCCCTGA

GACATGTGGTGTGCGCACATGAGCTGGTGTGCAGCATGGA

AAACACTAGGGCCACCAAGATGCAGGTCATCGGCGATCAG

TATGTCAAAGTGTACCTGGAGAGTTTTTGCGAAGACGTGC

CATCAGGGAAGCTGTTCATGCATGTGACCCTGGGCAGCGA

TGTCGAGGAAGACCTGACCATGACAAGAAATCCACAGCCC

TTTATGAGACCCCACGAGAGGAATGGGTTCACTGTGCTGT

GCCCCAAGAACATGATCATTAAGCCTGGAAAAATCAGTCA

TATTATGCTGGATGTGGCCTTTACATCACACGAGCATTTC

GGACTGCTGTGCCCCAAATCCATCCCTGGACTGAGCATTT

CCGGCAATCTGCTGATGAACGGCCAGCAGATCTTCCTGGA

AGTGCAGGCCATCCGGGAGACCGTCGAACTGCGACAGTAT

GACCCAGTGGCTGCACTGTTCTTTTTCGACATCGACCTGC

TGCTGCAGCGAGGACCACAGTACAGCGAGCACCCTACTTT

TACCTCCCAGTATCGGATTCAGGGGAAGCTGGAGTACAGG

CACACCTGGGATCGCCATGACGAAGGAGCCGCTCAGGGGG

ACGATGACGTGTGGACATCTGGCAGTGATTCAGACGAGGA

ACTGGTGACAACTGAGCGAAAAACCCCCCGGGTGACAGGA

GGAGGGGCAATGGCAGGGGCCAGCACCAGCGCAGGGCGGA

AGCGAAAAGCGCCAGCAGCGCCACAGCATGTACCGCCGG

CGTGATGACTAGAGGAAGGCTGAAGGCCGAGTCTACAGTC

GCTCCCGAGGAAGATACTGACGAGGATAGTGACAATGAAA

TCCACAACCCCGCCGTGTTCACCTGGCCACCTTGGCAGGC

AGGGATTCTGGCTCGCAACCTGGTCCCCATGGTGGCAACC

GTCCAGGGACAGAATCTGAAGTATCAGGAGTTTTTCTGGG

ATGCTAACGACATCTACCGGATTTTTGCAGAGCTGGAAGG

CGTGTGGCAGCCAGCAGCCCAGCCCAAACGACGGAGACAT

CGACAGGACGCTCTGCCAGGACCTTGTATCGCCAGCACAC

CAAAGAAGCACAGGGGCTAA
(SEQ ID NO: 6)

(MMLV Gag nucleotide sequence bolded)
Codon Optimized MMLV Gag-CMV pp65
Nucleotide Sequence
(SEQ ID NO: 22)

ATGGGACAGACCGTCACAACACCCCTGAGCCTGACCCTGG

GACATTGGAAAGACGTGGAGAGGATCGCACATAACCAGAG

-continued

CGTGGACGTGAAGAAACGGAGATGGGTCACATTCTGCAGT
GCTGAGTGGCCAACTTTTAATGTGGGATGGCCCCGAGACG
GCACTTTCAACAGGGATCTGATCACCCAGGTGAAGATCAA
GGTCTTTAGCCCAGGACCTCACGGACATCCAGACCAGGTG
CCTTATATCGTCACCTGGGAGGCACTGGCCTTCGATCCCC
CTCCATGGGTGAAGCCATTTGTCCACCCAAAACCACCTCC
ACCACTGCCTCCAAGTGCCCCTTCACTGCCACTGGAACCA
CCCCGGAGCACACCACCCCGCAGCTCCCTGTATCCTGCTC
TGACTCCATCTCTGGGCGCAAAGCCAAAACCACAGGTGCT
GAGCGACTCCGGAGGACCACTGATTGACCTGCTGACAGAG
GACCCCCCACCATACCGAGATCCTCGGCCTCCACCAAGCG
ACCGCGATGGAAATGGAGGAGAGGCTACTCCTGCCGGCGA
AGCCCCTGACCCATCTCCAATGGCTAGTAGGCTGCGCGGC
AGGCGCGAGCCTCCAGTGGCAGATAGCACCACATCCCAGG
CCTTCCCTCTGAGGGCTGGGGAAATGGGCAGCTCCAGTA
TTGGCCATTTTCTAGTTCAGACCTGTACAACTGGAAGAAC
AATAACCCCTCTTTCAGTGAGGACCCCGGCAAACTGACCG
CCCTGATCGAATCCGTGCTGATTACCCATCAGCCCACATG
GGACGATTGTCAGCAGCTCCTGGGCACCCTGCTGACCGGA
GAGGAAAAGCAGCGCGTGCTGCTGGAGGCTCGCAAAGCAG
TCCGAGGGGACGATGGACGGCCCACACAGCTCCCTAATGA
GGTGGACGCCGCTTTTCCACTGGAAAGACCCGACTGGGAT
TATACTACCCAGGCAGGGAGAAACCACCTGGTCCATTACA
GGCAGCTCCTGCTGGCAGGCCTGCAGAATGCCGGGAGATC
CCCCACCAACCTGGCCAAGGTGAAAGGCATCACACAGGGG
CCTAATGAGTCACCAAGCGCCTTTCTGGAGAGGCTGAAGG
AAGCTTACCGACGGTATACCCCATACGACCCTGAGGACCC
CGGACAGGAAACAAACGTCTCCATGTCTTTCATCTGGCAG
TCTGCCCCAGACATTGGGCGGAAGCTGGAGAGACTGGAAG
ACCTGAAGAACAAGACCCTGGGCGACCTGGTGCGGGAGGC
TGAAAAGATCTTCAACAAACGGGAGACCCCCGAGGAAAGA
GAGGAAAGGATTAGAAGGGAAACTGAGGAAAAGGAGGAAC
GCCGACGGACCGAGGACGAACAGAAGGAGAAAGAACGAGA
TCGGCGGCGGCACCGGGAGATGTCAAAGCTGCTGGCCACC
GTGGTCAGCGGACAGAAACAGGACAGACAGGGAGGAGAGC
GACGGAGAAGCCAGCTCGACAGGGATCAGTGCGCATACTG
TAAGGAAAAAGGCCATTGGGCCAAGGATTGCCCCAAAAAG
CCAAGAGGACCAAGAGGACCAAGACCACAGACATCACTGC
TGACCCTGGAC GACTGCGAGAGCCGGGCCGGCGGTGCCC
AGAAATGATCTCTGTGCTGGGGCCCATTAGTGGACATGTG
CTGAAGGCCGTCTTCTCCAGGGGAGACACCCCCGTGCTGC

-continued

CTCACGAGACTCGACTGCTGCAGACCGGCATCCATGTGCG
GGTCTCCCAGCCCTCTCTGATTCTGGTGTCACAGTATACA
CCAGATAGCACTCCCTGCCACAGAGGAGACAATCAGCTCC
AGGTGCAGCATACCTACTTTACAGGCTCCGAGGTCGAAAA
CGTGTCTGTCAATGTGCACAACCCTACCGGCAGGAGCATC
TGTCCTAGCCAGGAGCCAATGAGCATCTACGTGTACGCCC
TGCCTCTGAAGATGCTGAATATCCCATCAATTAACGTCCA
CCATTACCCTAGCGCAGCCGAACGGAAGCACAGACATCTG
CCAGTGGCCGACGCTGTCATCCATGCCAGCGGCAAACAGA
TGTGGCAGGCAAGACTGACCGTGTCCGGGCTGGCCTGGAC
AAGGCAGCAGAATCAGTGGAAGGAGCCCGACGTGTACTAT
ACCAGCGCCTTCGTGTTCCCTACCAAAGACGTGGCCCTGA
GACATGTGGTGTGCGCACATGAGCTGGTGTGCAGCATGGA
AAACACTAGGGCCACCAAGATGCAGGTCATCGGCGATCAG
TATGTCAAAGTGTACCTGGAGAGTTTTTGCGAAGACGTGC
CATCAGGGAAGCTGTTCATGCATGTGACCCTGGGCAGCGA
TGTCGAGGAAGACCTGACCATGACAAGAAATCCACAGCCC
TTTATGAGACCCCACGAGAGGAATGGGTTCACTGTGCTGT
GCCCCAAGAACATGATCATTAAGCCTGGAAAAATCAGTCA
TATTATGCTGGATGTGGCCTTTACATCACACGAGCATTTC
GGACTGCTGTGCCCCAAATCCATCCCTGGACTGAGCATTT
CCGGCAATCTGCTGATGAACGGCCAGCAGATCTTCCTGGA
AGTGCAGGCCATCCGGGAGACCGTCGAACTGCGACAGTAT
GACCCAGTGGCTGCACTGTTCTTTTTCGACATCGACCTGC
TGCTGCAGCGAGGACCACAGTACAGCGAGCACCCTACTTT
TACCTCCCAGTATCGGATTCAGGGGAAGCTGGAGTACAGG
CACACCTGGGATCGCCATGACGAAGGAGCCGCTCAGGGGG
ACGATGACGTGTGGACATCTGGCAGTGATTCAGACGAGGA
ACTGGTGACAACTGAGCGAAAAACCCCCCGGGTGACAGGA
GGAGGGCAATGGCAGGGGCCAGCACCAGCGCAGGGCGGA
AGCGAAAAAGCGCCAGCAGCGCCACAGCATGTACCGCCGG
CGTGATGACTAGAGGAAGGCTGAAGGCCGAGTCTACAGTC
GCTCCCGAGGAAGATACTGACGAGGATAGTGACAATGAAA
TCCACAACCCCGCCGTGTTCACCTGGCCACCTTGGCAGGC
AGGGATTCTGGCTCGCAACCTGGTCCCCATGGTGGCAACC
GTCCAGGGACAGAATCTGAAGTATCAGGAGTTTTTCTGGG
ATGCTAACGACATCTACCGGATTTTTGCAGAGCTGGAAGG

-continued

```
CGTGTGGCAGCCAGCAGCCCAGCCCAAACGACGGAGACAT

CGACAGGACGCTCTGCCAGGACCTTGTATCGCCAGCACAC

CAAAGAAGCACAGGGGCTAA
(SEQ ID NO: 22)
(MMLV Gag nucleotide sequence bolded)
```

In some embodiments, the present invention provides nucleic acids which encode a Gag polypeptide or a characteristic portion of a Gag polypeptide. In certain embodiments, nucleic acids can be DNA or RNA, and can be single stranded or double-stranded. In some embodiments, inventive nucleic acids may include one or more non-natural nucleotides; in other embodiments, inventive nucleic acids include only natural nucleotides.

B. Envelope Proteins

In some embodiments, the present invention utilizes VLPs comprised of one or more envelope polypeptides from HCMV (e.g., gB and/or gH). As used herein, the term "envelope polypeptide" refers to a polypeptide sequence whose amino acid sequence includes at least one characteristic sequence of an envelope glycoprotein. A wide variety of envelope glycoprotein sequences from various viruses, including, but not limited to HCMV, are known in the art and those of ordinary skill in the art, referring to such sequences, can readily identify sequences that are characteristic of envelope glycoproteins generally, and/or of particular envelope glycoproteins. In some embodiments, an envelope polypeptide comprises a cytoplasmic, transmembrane and/or extracellular portion or domain.

In some embodiments, an envelope polypeptide from HCMV includes a transmembrane and cytoplasmic domain that is not found in nature in the HCMV protein. For example, in some embodiments, an envelope polypeptide from HCMV includes a transmembrane and cytoplasmic domain from another HCMV protein (e.g., gB or gH). In some embodiments, an envelope polypeptide from HCMV includes a transmembrane domain and cytoplasmic domain found in nature in vesicular stomatitis virus (VSV). As is known in the art, polypeptides sometimes have transmembrane, cytoplasmic, and/or extracellular domains. In general, a "transmembrane domain", as used herein, refers to a domain that has an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localiza-tion (e.g., cytoplasmic localization). Exemplary such programs include psort (PSORT.org), Prosite (prosite.expasy.org), among others.

The transmembrane domain of VSV-G functions to target the viral glycoprotein to the cell membrane (Compton T et al., 1989 Proc Natl Acad Sci USA 86:4112-4116). Swapping the transmembrane and cytoplasmic domains of VSV-G for the transmembrane and cytoplasmic domains of another protein has been used to direct a protein to the cell membrane when the native protein does not naturally do this or requires accessory co-expressed proteins to accomplish this (Garrone P et al., 2011 Sci Transl Med 94:).

Among other things, the present invention encompasses the recognition that VLPs containing a structural component of a virus (e.g., MLV) and one or more heterologous surface antigens (e.g., envelope protein) are especially effective for antigen delivery and induction of an immune response against the heterologous antigen.

C. Heterologous Antigens

Envelope proteins of HCMV, such as glycoproteins gB and gH, are important targets for production of neutralizing antibodies against HCMV, as neutralizing antibodies are generally able to prevent infection. Therapies for HCMV infection, such as a gB subunit vaccine, have been developed and tested in experimental animals and clinical studies. Results from such studies, however, have demonstrated that in humans, the antibody response was not long-lived and not sufficiently effective for the treatment of HCMV in all cases. The reasons which have been suggested for the limited efficacy of subunit vaccines based exclusively on gB of HCMV in turn are strain-specific variations in immune responses, inadequate induction of a cellular immune response, and structural restrictions on antigen used, whose epitopes are thought to be conformation-dependent. The present inventors recognized that development of an HCMV vaccine comprising one or more envelope polypeptide antigens presented in their native conformation on the surface of a VLP leads to induction of neutralizing antibodies (e.g., via a humoral immune response) and an HCMV vaccine comprising one or more structural protein antigens (e.g., tegument protein pp65) leads to induction of helper T cells (Tx lymphocytes) and cytotoxic T cells (CTL) (e.g., via a cell-mediated immune response). Neutralizing antibodies are generally formed against viral envelope proteins, and especially against HCMV glycoproteins gB and gH. $T_H$ cells are stimulated by tegument structural proteins of a virus, such as, for example, HCMV pp65 (ppUL83). In addition, pp65 plays an important role in induction of a CTL response against HCMV.

It will be appreciated that provided VLPs may comprise any heterologous antigen, including heterologous antigens from HCMV. For example, in some embodiments, a VLP in accordance with the present invention comprises one or more HCMV envelope polypeptides. In some embodiments, a VLP in accordance with the present invention comprises one or more HCMV structural polypeptides. In some embodiments, a VLP in accordance with the present invention comprises one or more HCMV envelope polypeptides and one or more HCMV structural polypeptides. A list of exemplary, but non-limiting HCMV antigens is provided below.

gB—Glycoprotein Complex (gC) I

The most fully characterized glycoprotein complex of HCMV is the gB complex (gB;UL55). It has been demonstrated that sera from CMV-seropositive individuals contains antibodies to gB, and up to 70% of the neutralizing antibody response in convalescent sera is gB-specific (Marshall G S et al., 1994 J Med Virol 43:77-83).

An exemplary HCMV gB polypeptide amino acid and nucleic acid sequence is shown below as SEQ ID NO:7 and SEQ ID NO:8, respectively. In some embodiments, a suitable gB polypeptide is substantially homologous to a known HCMV gB polypeptide. For example, a gB polypeptide may be a modified HCMV gB polypeptide containing one or more amino acid substitutions, deletions, and/or insertions as compared to a wild-type or naturally-occurring gB polypeptide (e.g., SEQ ID NO:7). Thus, in some embodiments, a gB polypeptide suitable for the present invention is substantially homologous to an HCMV gB polypeptide (SEQ ID NO:7). In some embodiments, an HCMV polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:7. In some embodiments, a gB polypeptide suitable for the present invention is substantially identical to an HCMV gB polypeptide (SEQ ID NO:7). In some embodiments, a gB polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:7.

```
HCMV gB Amino Acid Sequence
                                      (SEQ ID NO: 7)
MESRIWCLVVCVNLCIVCLGAAVSSSSTRGTSATHSHHSS

HTTSAAHSRSGSVSQRVTSSQTVSHGVNETIYNTTLKYGD

VVGVNTTKYPYRVCSMAQGTDLIRFERNIVCTSMKPINED

LDEGIMVVYKRNIVAHTFKVRVYQKVLTFRRSYAYIHTTY

LLGSNTEYVAPPMWEIHHINSHSQCYSSYSRVIAGTVFVA

YHRDSYENKTMQLMPDDYSNTHSTRYVTVKDQWHSRGSTW

LYRETCNLNCMVTITTARSKYPYHFFATSTGDVVDISPFY

NGTNRNASYFGENADKFFIFPNYTIVSDFGRPNSALETHR

LVAFLERADSVISWDIQDEKNVTCQLTFWEASERTIRSEA

EDSYHFSSAKMTATFLSKKQEVNMSDSALDCVRDEAINKL

QQIFNTSYNQTYEKYGNVSVFETTGGLVVFWQGIKQKSLV

ELERLANRSSLNLTHNRTKRSTDGNNATHLSNMESVHNLV

YAQLQFTYDTLRGYINRALAQIAEAWCVDQRRTLEVFKEL

SKINPSAILSAIYNKPIAARFMGDVLGLASCVTINQTSVK

VLRDMNVKESPGRCYSRPVVIFNFANSSYVQYGQLGEDNE

ILLGNHRTEECQLPSLKIFIAGNSAYEYVDYLFKRMIDLS

SISTVDSMIALDIDPLENTDFRVLELYSQKELRSINVFDL

EEIMREFNSYKQRVKYVEDKVVDPLPPYLKGLDDLMSGLG

AAGKAVGVAIGAVGGAVASVVEGVATFLKNPFGAFTIILV

AIAVVIIIYLIYTRQRRLCMQPLQNLFPYLVSADGTTVTS

GNTKDTSLQAPPSYEESVYNSGRKGPGPPSSDASTAAPPY

TNEQAYQMLLALVRLDAEQRAQQNGTDSLDGQTGTQDKGQ

KPNLLDRLRHRKNGYRHLKDSDEEENV*
(SEQ ID NO: 7) (TM and CD underlined)
```

```
HCMV gB Nucleotide Sequence
                                      (SEQ ID NO: 8)
ATGGAATCCAGGATCTGGTGCCTGGTAGTCTGCGTTAACT

TGTGTATCGTCTGTCTGGGTGCTGCGGTTTCCTCATCTTC

TACTCGTGGAACTTCTGCTACTCACAGTCACCATTCCTCT

CATACGACGTCTGCTGCTCATTCTCGATCCGGTTCAGTCT

CTCAACGCGTAACTTCTTCCCAAACGGTCAGCCATGGTGT

TAACGAGACCATCTACAACACTACCCTCAAGTACGGAGAT

GTGGTGGGGGTCAACACCACCAAGTACCCCTATCGCGTGT

GTTCTATGGCACAGGGTACGGATCTTATTCGCTTTGAACG

TAATATCGTCTGCACCTCGATGAAGCCCATCAATGAAGAC

CTGGACGAGGGCATCATGGTGGTCTACAAACGCAACATCG

TCGCGCACACCTTTAAGGTACGAGTCTACCAGAAGGTTTT

GACGTTTCGTCGTAGCTACGCTTACATCCACACCACTTAT

CTGCTGGGCAGCAACACGGAATACGTGGCGCCTCCTATGT

GGGAGATTCATCATATCAACAGTCACAGTCAGTGCTACAG

TTCCTACAGCCGCGTTATAGCAGGCACGGTTTTCGTGGCT

TATCATAGGGACAGCTATGAAAACAAAACCATGCAATTAA

TGCCCGACGATTATTCCAACACCCACAGTACCCGTTACGT

GACGGTCAAGGATCAATGGCACAGCCGCGGCAGCACCTGG

CTCTATCGTGAGACCTGTAATCTGAATTGTATGGTGACCA

TCACTACTGCGCGCTCCAAGTATCCCTATCATTTTTCGC

AACTTCCACGGGTGATGTGGTTGACATTTCTCCTTTCTAC

AACGGAACTAATCGCAATGCCAGCTATTTTGGAGAAAACG

CCGACAAGTTTTTCATTTTTCCGAACTACACTATCGTCTC

CGACTTTGGAAGACCGAATTCTGCGTTAGAGACCCACAGG

TTGGTGGCTTTTCTTGAACGTGCGGACTCAGTGATCTCCT

GGGATATACAGGACGAGAAGAATGTTACTTGTCAACTCAC

TTTCTGGGAAGCCTCGGAACGCACCATTCGTTCCGAAGCC

GAGGACTCGTATCACTTTTCTTCTGCCAAAATGACCGCCA

CTTTCTTATCTAAGAAGCAAGAGGTGAACATGTCCGACTC

TGCGCTGGACTGTGTACGTGATGAGGCCATAAATAAGTTA

CAGCAGATTTTCAATACTTCATACAATCAAACATATGAAA

AATATGGAAACGTGTCCGTCTTTGAAACCACTGGTGGTTT

GGTGGTGTTCTGGCAAGGTATCAAGCAAAAATCTCTGGTG

GAACTCGAACGTTTGGCCAACCGCTCCAGTCTGAATCTTA

CTCATAATAGAACCAAAAGAAGTACAGATGGCAACAATGC

AACTCATTTATCCAACATGGAGTCGGTGCACAATCTGGTC

TACGCCCAGCTGCAGTTCACCTATGACACGTTGCGCGGTT

ACATCAACCGGGCGCTGGCGCAAATCGCAGAAGCCTGGTG

TGTGGATCAACGGCGCACCCTAGAGGTCTTCAAGGAACTT
```

-continued

AGCAAGATCAACCCGTCAGCTATTCTCTCGGCCATCTACA
ACAAACCGATTGCCGCGCGTTTCATGGGTGATGTCCTGGG
TCTGGCCAGCTGCGTGACCATTAACCAAACCAGCGTCAAG
GTGCTGCGTGATATGAATGTGAAGGAATCGCCAGGACGCT
GCTACTCACGACCAGTGGTCATCTTTAATTTCGCCAACAG
CTCGTACGTGCAGTACGGTCAACTGGGCGAGGATAACGAA
ATCCTGTTGGGCAACCACCGCACTGAGGAATGTCAGCTTC
CCAGCCTCAAGATCTTCATCGCCGGCAACTCGGCCTACGA
GTACGTGGACTACCTCTTCAAACGCATGATTGACCTCAGC
AGCATCTCCACCGTCGACAGCATGATCGCCCTAGACATCG
ACCCGCTGGAAAACACCGACTTCAGGGTACTGGAACTTTA
CTCGCAGAAAGAATTGCGTTCCATCAACGTTTTTGATCTC
GAGGAGATCATGCGCGAGTTCAATTCGTATAAGCAGCGGG
TAAAGTACGTGGAGGACAAGGTAGTCGACCCGCTGCCGCC
CTACCTCAAGGGTCTGGACGACCTCATGAGCGGCCTGGGC
GCCGCGGGAAAGGCCGTTGGCGTAGCCATTGGGGCCGTGG
GTGGCGCGGTGGCCTCCGTGGTCGAAGGCGTTGCCACCTT
CCTCAAAAACCCCTTCGGAGCCTTCACCATCATCCTCGTG
GCCATAGCCGTCGTCATTATCATTTATTTGATCTATACTC
GACAGCGGCGTCTCTGCATGCAGCCGCTGCAGAACCTCTT
TCCCTATCTGGTGTCCGCCGACGGGACCACCGTGACGTCG
GGCAACACCAAAGACACGTCGTTACAGGCTCCGCCTTCCT
ACGAGGAAAGTGTTTATAATTCTGGTCGCAAAGGACCGGG
ACCACCGTCGTCTGATGCATCCACGGCGGCTCCGCCTTAC
ACCAACGAGCAGGCTTACCAGATGCTTCTGGCCCTGGTCC
GTCTGGACGCAGAGCAGCGAGCGCAGCAGAACGGTACAGA
TTCTTTGGACGGACAGACTGGCACGCAGGACAAGGGACAG
AAGCCCAACCTGCTAGACCGACTGCGACACCGCAAAAACG
GCTACCGACACTTGAAAGACTCCGACGAAGAAGAGAACGT
CTGA
(SEQ ID NO: 8) (TM and CD underlined)

Codon Optimized HCMV &B Nucleotide Sequence
(SEQ ID NO: 9)
ATGGAGTCAAGGATTTGGTGCCTGGTCGTGTGCGTCAATC
TGTGCATCGTCTGTCTGGGGGCTGCCGTGTCATCAAGTTC
TACAAGAGGCACCAGCGCCACCCACTCACACCATAGCTCC
CATACCACATCCGCCGCTCACTCCCGGTCTGGCAGCGTGA
GCCAGAGAGTCACATCTAGTCAGACCGTGAGCCACGGGGT
CAACGAGACCATCTACAATACTACCCTGAAGTATGGCGAC
GTGGTCGGGGTGAACACAACTAAATACCCATATAGGGTCT
GCAGTATGGCCCAGGGCACTGATCTGATTAGATTCGAAAG
GAACATCGTGTGCACCAGCATGAAGCCCATTAATGAGGAC CTGGATGAAGGGATCATGGTGGTCTACAAACGCAATATTG
TGGCCCATACCTTCAAGGTGCGAGTCTATCAGAAAGTGCT
GACATTTCGGAGATCTTACGCATATATCCACACCACATAC
CTGCTGGGGAGTAACACCGAGTATGTGGCTCCCCCTATGT
GGGAAATTCACCATATCAATAGCCATTCCCAGTGCTACTC
AAGCTACAGCAGAGTGATCGCTGGAACAGTGTTCGTCGCA
TACCACAGAGACTCTTATGAGAACAAGACTATGCAGCTCA
TGCCCGACGATTACAGCAATACACATTCCACTAGATATGT
GACAGTCAAAGATCAGTGGCACTCAAGGGGCAGCACCTGG
CTGTACCGCGAGACATGCAACCTGAATTGTATGGTGACTA
TCACTACCGCTAGATCCAAGTACCCCTATCACTTCTTTGC
AACTTCCACCGGGGACGTGGTCGATATTTCTCCTTTCTAC
AACGGCACAAACCGGAATGCATCTTATTTTGGGGAGAACG
CCGACAAGTTCTTTATTTTCCCAAATTACACCATCGTGTC
TGATTTTGGCAGACCCAACAGTGCCCTGGAGACACATCGA
CTGGTGGCATTCCTGGAACGGGCCGACTCCGTCATTTCTT
GGGACATCCAGGATGAGAAGAATGTGACCTGCCAGCTCAC
CTTCTGGGAGGCCAGCGAACGCACCATCCGATCCGAGGCT
GAAGATTCTTACCACTTCTCCTCTGCCAAAATGACAGCTA
CTTTTCTGAGCAAGAAACAGGAGGTGAACATGTCTGACAG
TGCTCTGGATTGCGTGCGGGACGAAGCAATTAATAAGCTG
CAGCAGATCTTCAACACATCATACAACCAGACTTACGAGA
AGTACGGAAACGTGAGCGTCTTCGAAACAACTGGCGGGCT
GGTGGTCTTTTGGCAGGGCATCAAGCAGAAATCCCTGGTG
GAGCTGGAAAGGCTGGCCAATCGCAGTTCACTGAACCTGA
CTCATAATCGGACCAAGAGATCTACAGACGGAAACAATGC
CACACATCTGTCTAACATGGAGAGTGTGCACAATCTGGTC
TACGCTCAGCTCCAGTTTACCTACGACACACTGAGAGGCT
ATATTAACAGGGCACTGGCCCAGATCGCTGAAGCATGGTG
CGTGGATCAGAGGCGCACCCTGGAGGTCTTCAAGGAACTG
TCCAAAATCAACCCTTCAGCAATTCTGAGCGCCATCTACA
ATAAGCCAATTGCAGCCAGGTTTATGGGAGACGTGCTGGG
CCTGGCCAGTTGCGTCACTATCAACCAGACCTCAGTGAAG
GTCCTGCGCGATATGAATGTGAAAGAGAGTCCCGGCAGAT
GCTATTCACGGCCTGTGGTCATCTTCAACTTTGCTAATAG
CTCCTACGTGCAGTATGGACAGCTCGGCGAGGACAACGAA
ATTCTGCTGGGGAATCACAGGACCGAGGAATGTCAGCTCC
CTAGCCTGAAGATTTTCATCGCTGGAAACTCCGCATACGA
GTATGTGGATTACCTGTTCAAGCGGATGATTGACCTGTCT
AGTATCTCCACTGTGGATTCTATGATTGCCCTGGACATCG
ATCCACTGGAAAATACCGACTTCAGGGTGCTGGAGCTGTA

```
TAGCCAGAAGGAACTGCGCTCCATCAACGTGTTCGATCTG

GAGGAAATTATGAGAGAGTTTAATAGCTACAAGCAGAGGG

TGAAATATGTCGAAGATAAGGTGGTCGACCCCCTGCCACC

CTACCTGAAAGGCCTGGACGATCTGATGAGCGGGCTGGGA

GCTGCAGGGAAGGCAGTGGGAGTCGCTATCGGCGCAGTGG

GAGGAGCCGTGGCCAGCGTGGTCGAGGGAGTGGCAACATT

CCTGAAAAACCCCTTCGGGGCCTTCACCATCATTCTGGTG

GCAATCGCCGTGGTCATCATTATCTACCTGATCTACACAA

GGCAGCGGCGGCTGTGCATGCAGCCTCTGCAGAACCTGTT

TCCATACCTGGTGAGCGCCGACGGGACCACAGTCACCTCA

GGAAATACTAAGGATACCTCTCTGCAGGCCCCCCCAAGTT

ACGAGGAATCAGTGTATAACAGCGGCAGAAAAGGACCAGG

ACCACCTTCAAGCGACGCCAGCACTGCCGCTCCACCCTAC

ACCAATGAGCAGGCCTATCAGATGCTGCTGGCTCTGGTGC

GCCTGGATGCCGAACAGCGAGCTCAGCAGAACGGGACCGA

CTCCCTGGATGGACAGACCGGAACACAGGACAAGGGACAG

AAACCTAATCTGCTGGATCGGCTGCGGCACAGAAAAAACG

GGTATAGGCACCTGAAGGACTCCGACGAAGAAGAAAATGT

CTAA
```
(SEQ ID NO: 9) (TM and CD underlined)

In some embodiments, a gB polypeptide for use in accordance with the present invention lacks a transmembrane domain and/or cytoplasmic domain and/or contains a modified transmembrane domain and/or cytoplasmic domain. A gB polypeptide may optionally include one or more additional polypeptides (e.g., a heterologous transmembrane domain and/or cytoplasmic domain polypeptide). In some embodiments, a gB polypeptide is expressed as a fusion protein with a heterologous polypeptide. The gB polypeptide can be linked to a heterologous polypeptide to create a fusion protein without altering gB function and/or antigenicity. For example, a coding sequence for a heterologous polypeptide may be spliced into the gB polypeptide coding sequence, e.g., at the 3' end of the gB polypeptide coding sequence. In some embodiments, a coding sequence for a heterologous polypeptide may be spliced in frame into the gB polypeptide coding sequence. In some embodiments, a gB polypeptide-coding sequence and heterologous polypeptide may be expressed by a single promoter. In some embodiments, a heterologous polypeptide is inserted at (e.g., fused to) the C-terminus of a gB polypeptide.

In some embodiments, a heterologous polypeptide is or comprises a transmembrane domain and/or cytoplasmic domain found in Vesicular Stomatitis Virus (VSV). In some embodiments, a gB that is lacking a transmembrane domain and/or cytoplasmic domain is fused to a transmembrane domain and/or cytoplasmic domain from VSV. An exemplary gB-VSV fusion polypeptide for use in accordance with the present invention is shown below as SEQ ID NO:10. In some embodiments, a suitable gB-VSV polypeptide fusion protein includes all or a portion of a gB polypeptide that is substantially homologous to a known gB polypeptide and all or a portion of a VSV polypeptide that is substantially homologous to a known VSV polypeptide. For example, a gB—VSV polypeptide fusion protein may contain one or more amino acid substitutions, deletions, and/or insertions as compared to a wild-type or naturally-occurring gB and/or VSV polypeptide. Thus, in some embodiments, a gB-VSV polypeptide fusion protein suitable for the present invention is substantially homologous to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:10. In some embodiments, a gB-VSV polypeptide fusion protein suitable for the present invention is substantially identical to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:10. As used herein, "gB-G" refers to a HMCV gB—VSV TM/CTD fusion protein.

```
HCMV gB-G Amino Acid Sequence
                               (SEQ ID NO: 10)
MESRIWCLVVCVNLCIVCLGAAVSSSSTRGTSATHSHHSS

HTTSAAHSRSGSVSQRVTSSQTVSHGVNETIYNTTLKYGD

VVGVNTTKYPYRVCSMAQGTDLIRFERNIVCTSMKPINED

LDEGIMVVYKRNIVAHTFKVRVYQKVLTFRRSYAYIHTTY

LLGSNTEYVAPPMWEIHHINSHSQCYSSYSRVIAGTVFVA

YHRDSYENKTMQLMPDDYSNTHSTRYVTVKDQWHSRGSTW

LYRETCNLNCMVTITTARSKYPYHFFATSTGDVVDISPFY

NGTNRNASYFGENADKFFIFPNYTIVSDFGRPNSALETHR

LVAFLERADSVISWDIQDEKNVTCQLTFWEASERTIRSEA

EDSYHFSSAKMTATFLSKKQEVNMSDSALDCVRDEAINKL

QQIFNTSYNQTYEKYGNVSVFETTGGLVVFWQGIKQKSLV

ELERLANRSSLNLTHNRTKRSTDGNNATHLSNMESVHNLV

YAQLQFTYDTLRGYINRALAQIAEAWCVDQRRTLEVFKEL

SKINPSAILSAIYNKPIAARFMGDVLGLASCVTINQTSVK

VLRDMNVKESPGRCYSRPVVIFNFANSSYVQYGQLGEDNE

ILLGNHRTEECQLPSLKIFIAGNSAYEYVDYLFKRMIDLS

SISTVDSMIALDIDPLENTDFRVLELYSQKELRSINVFDL

EEIMREFNSYKQRVKYVEDKVVDPLPPYLKGLDDLMSGLG

AAGKAVGVAIGAVGGAVASVVEGVATFLKNPFFFIIGLII

GLFLVLRVGIHLCIKLKHTKKRQIYTDIEMNRLGK*
```
(SEQ ID NO: 10) (TM and CTD underlined)

```
HCMV gB-G Nucleotide Sequence
                               (SEQ ID NO: 11)
ATGGAATCCAGGATCTGGTGCCTGGTAGTCTGCGTTAACT

TGTGTATCGTCTGTCTGGGTGCTGCGGTTTCCTCATCTTC

TACTCGTGGAACTTCTGCTACTCACAGTCACCATTCCTCT

CATACGACGTCTGCTGCTCATTCTCGATCCGGTTCAGTCT

CTCAACGCGTAACTTCTTCCCAAACGGTCAGCCATGGTGT
```

-continued
TAACGAGACCATCTACAACACTACCCTCAAGTACGGAGAT
GTGGTGGGGGTCAACACCACCAAGTACCCCTATCGCGTGT
GTTCTATGGCACAGGGTACGGATCTTATTCGCTTTGAACG
TAATATCGTCTGCACCTCGATGAAGCCCATCAATGAAGAC
CTGGACGAGGGCATCATGGTGGTCTACAAACGCAACATCG
TCGCGCACACCTTTAAGGTACGAGTCTACCAGAAGGTTTT
GACGTTTCGTCGTAGCTACGCTTACATCCACACCACTTAT
CTGCTGGGCAGCAACACGGAATACGTGGCGCCTCCTATGT
GGGAGATTCATCATATCAACAGTCACAGTCAGTGCTACAG
TTCCTACAGCCGCGTTATAGCAGGCACGGTTTTCGTGGCT
TATCATAGGGACAGCTATGAAAACAAAACCATGCAATTAA
TGCCCGACGATTATTCCAACACCCACAGTACCCGTTACGT
GACGGTCAAGGATCAATGGCACAGCCGCGGCAGCACCTGG
CTCTATCGTGAGACCTGTAATCTGAATTGTATGGTGACCA
TCACTACTGCGCGCTCCAAGTATCCCTATCATTTTTTCGC
AACTTCCACGGGTGATGTGGTTGACATTTCTCCTTTCTAC
AACGGAACTAATCGCAATGCCAGCTATTTTGGAGAAAACG
CCGACAAGTTTTTCATTTTTCCGAACTACACTATCGTCTC
CGACTTTGGAAGACCGAATTCTGCGTTAGAGACCCACAGG
TTGGTGGCTTTTCTTGAACGTGCGGACTCAGTGATCTCCT
GGGATATACAGGACGAGAAGAATGTTACTTGTCAACTCAC
TTTCTGGGAAGCCTCGGAACGCACCATTCGTTCCGAAGCC
GAGGACTCGTATCACTTTTCTTCTGCCAAAATGACCGCCA
CTTTCTTATCTAAGAAGCAAGAGGTGAACATGTCCGACTC
TGCGCTGGACTGTGTACGTGATGAGGCCATAAATAAGTTA
CAGCAGATTTTCAATACTTCATACAATCAAACATATGAAA
AATATGGAAACGTGTCCGTCTTTGAAACCACTGGTGGTTT
GGTGGTGTTCTGGCAAGGTATCAAGCAAAAATCTCTGGTG
GAACTCGAACGTTTGGCCAACCGCTCCAGTCTGAATCTTA
CTCATAATAGAACCAAAAGAAGTACAGATGGCAACAATGC
AACTCATTTATCCAACATGGAGTCGGTGCACAATCTGGTC
TACGCCCAGCTGCAGTTCACCTATGACACGTTGCGCGGTT
ACATCAACCGGGCGCTGGCGCAAATCGCAGAAGCCTGGTG
TGTGGATCAACGGCGCACCCTAGAGGTCTTCAAGGAACTT
AGCAAGATCAACCCGTCAGCTATTCTCTCGGCCATCTACA
ACAAACCGATTGCCGCGCGTTTCATGGGTGATGTCCTGGG
TCTGGCCAGCTGCGTGACCATTAACCAAACCAGCGTCAAG
GTGCTGCGTGATATGAATGTGAAGGAATCGCCAGGACGCT
GCTACTCACGACCAGTGGTCATCTTTAATTTCGCCAACAG
CTCGTACGTGCAGTACGGTCAACTGGGCGAGGATAACGAA
ATCCTGTTGGGCAACCACCGCACTGAGGAATGTCAGCTTC CCAGCCTCAAGATCTTCATCGCCGGCAACTCGGCCTACGA
GTACGTGGACTACCTCTTCAAACGCATGATTGACCTCAGC
AGCATCTCCACCGTCGACAGCATGATCGCCCTAGACATCG
ACCCGCTGGAAAACACCGACTTCAGGGTACTGGAACTTTA
CTCGCAGAAAGAATTGCGTTCCATCAACGTTTTTGATCTC
GAGGAGATCATGCGCGAGTTCAATTCGTATAAGCAGCGGG
TAAAGTACGTGGAGGACAAGGTAGTCGACCCGCTGCCGCC
CTACCTCAAGGGTCTGGACGACCTCATGAGCGGCCTGGGC
GCCGCGGGAAAGGCCGTTGGCGTAGCCATTGGGGCCGTGG
GTGGCGCGGTGGCCTCCGTGGTCGAAGGCGTTGCCACCTT
CCTCAAAAACCCC<u>TTTTTCTTTATCATAGGGTTAATCATT
GGACTATTCTTGGTTCTCCGAGTTGGTATCCATCTTTGCA
TTAAATTAAAGCACACCAAGAAAAGACAGATTTATACAGA
CATAGAGATGAACCGACTTGGAAAGTAA</u>
(SEQ ID NO: 11) TM and CTD underlined)

Codon Optimized HCMV gB-G Nucleotide Sequence
(SEQ ID NO: 12)
ATGGAGTCAAGGATTTGGTGTCTGGTCGTCTGCGTCAACC
TGTGCATTGTCTGCCTGGGAGCCGCCGTCTCATCATCATC
TACCCGAGGCACATCCGCCACTCACTCTCACCATAGCTCC
CATACCACATCCGCCGCTCACTCAAGAAGCGGGTCCGTGT
CTCAGAGGGTCACATCTAGTCAGACCGTGAGCCATGGAGT
CAACGAGACAATCTACAATACTACCCTGAAGTATGGAGAC
GTGGTCGGCGTGAACACAACTAAATACCCCTATAGGGTCT
GCTCTATGGCCCAGGGGACAGATCTGATCCGATTTGAACG
GAACATCGTGTGCACTAGCATGAAGCCTATCAATGAGGAC
CTGGATGAAGGAATTATGGTGGTCTACAAACGAAATATCG
TGGCCCATACTTTTAAGGTGAGAGTCTATCAGAAAGTGCT
GACCTTCCGGAGAAGCTACGCTTATATTCACACCACATAC
CTGCTGGGGTCCAACACCGAGTATGTGGCACCCCCTATGT
GGGAAATCCACCATATTAATAGTCATTCACAGTGCTACTC
AAGCTACAGCAGAGTGATCGCTGGAACCGTGTTCGTCGCA
TACCACAGAGACAGTTATGAGAACAAGACAATGCAGCTCA
TGCCCGACGATTACAGTAATACCCATTCAACAAGATATGT
GACCGTCAAAGATCAGTGGCACTCTCGCGGCAGTACCTGG
CTGTACGAGAGACATGCAACCTGAATTGTATGGTGACAA
TTACTACCGCCAGAAGCAAGTACCCTTATCACTTCTTTGC
TACCTCAACAGGGGACGTGGTCGACATCAGCCCCTTCTAC
AACGGAACAAACCGGAATGCCTCCTATTTCGGCGAGAACG
CTGACAAATTCTTTATCTTCCCCAACTACACTATCGTGAG
CGATTTCGGCAGACCTAACAGTGCCCTGGAGACCCATCGG
CTGGTGGCATTTCTGGAAAGAGCCGACAGCGTGATCTCCT -continued

```
GGGACATTCAGGATGAGAAGAATGTGACCTGCCAGCTCAC

CTTCTGGGAGGCCAGCGAAAGAACCATCAGGTCCGAGGCA

GAAGATTCTTACCACTTTTCCTCTGCAAAAATGACTGCCA

CCTTCCTGTCCAAGAAACAGGAGGTGAACATGAGCGACTC

CGCACTGGATTGCGTGCGGGACGAAGCCATCAATAAGCTG

CAGCAGATCTTCAACACATCTTACAACCAGACTTACGAGA

AGTACGGCAACGTGAGTGTCTTTGAAACAACTGGCGGGCT

GGTGGTCTTCTGGCAGGGGATCAAGCAGAAATCTCTGGTG

GAGCTGGAACGGCTGGCCAATAGAAGTTCACTGAACCTGA

CTCATAATCGCACCAAGCGATCCACAGACGGAAACAATGC

AACTCATCTGAGCAACATGGAGTCCGTGCACAATCTGGTC

TACGCCCAGCTCCAGTTCACTTACGACACCCTGCGAGGCT

ATATCAACCGGGCCCTGGCTCAGATTGCAGAAGCCTGGTG

CGTGGATCAGAGGCGCACCCTGGAGGTCTTTAAGGAACTG

AGCAAAATTAACCCATCTGCTATCCTGAGTGCAATCTACA

ATAAGCCCATCGCAGCCAGGTTCATGGGGGACGTGCTGGG

ACTGGCCTCCTGCGTCACTATCAACCAGACCTCTGTGAAG

GTCCTGCGCGATATGAATGTGAAAGAGAGTCCTGGCAGGT

GTTATTCACGCCCAGTGGTCATCTTCAACTTCGCTAATAG

CTCCTACGTGCAGTATGGCCAGCTCGGGGAGGACAACGAA

ATCCTGCTGGGAAATCACAGGACCGAGGAATGTCAGCTCC

CAAGTCTGAAGATCTTTATTGCCGGCAACTCAGCTTACGA

GTATGTGGATTACCTGTTCAAACGCATGATCGACCTGTCT

AGTATTTCAACAGTGGATAGCATGATCGCCCTGGACATTG

ATCCCCTGGAAAATACTGACTTCAGGGTGCTGGAGCTGTA

TAGCCAGAAGGAACTGCGCTCCATTAACGTGTTTGATCTG

GAGGAAATCATGAGGGAGTTCAATTCCTACAAGCAGCGCG

TGAAATATGTCGAAGATAAGGTGGTCGACCCTCTGCCACC

CTACCTGAAAGGCCTGGACGATCTGATGAGCGGGCTGGGA

GCTGCAGGCAAGGCAGTGGGAGTCGCCATCGGAGCTGTGG

GAGGCGCTGTCGCATCCGTGGTCGAGGGAGTGGCTACCTT

TCTGAAGAACCCATTCTTTTTCATCATCGGCCTGATCATT

GGGCTGTTCCTGGTGCTGAGAGTCGGCATCCACCTGTGCA

TTAAGCTGAAGCACACCAAGAAGAGGCAGATCTACACCGA

TATTGAAATGAACAGACTGGGCAAGTGA
```
(SEQ ID NO: 12) (TM and CTD underlined)

gH—Glycoprotein Complex (gC) III

The gc III complex contains glycoproteins gH (UL75), gL (UL115) and gO (UL74) (Urban M et al., 1996 J Gen Virol 77:1537-47). Like gB, gH is conserved among human pathogenic herpesviruses and plays an important role in a number of steps during HCMV replication. HCMV encodes two gH/gL complexes: gH/gL/gO and a gH/gL/UL128/UL130/UL131 complex (Wang D and Shenk T 2005 Proc Natl Acad USA 102:18153-8). The gO-containing complex is generally sufficient for fibroblast infection with HCMV, whereas the UL128/UL130/UL131-containing complex is needed in order for HCMV to infect endothelial and epithelial cells (Wang D and Shenk T 2005 J Virol 79 10330-8). Natural infection with HCMV typically elicits high titer neutralizing antibodies specific for epithelial cell entry and it has been demonstrated that antibodies against gH/gL/UL128/UL130/UL131 epitopes may comprise a significant component of this activity (Macagno A et al., 2010 J Virol 84:1005-13). Immunological studies on gH have demonstrated that in mammalian cells the protein requires additional polypeptides (like gL) for correct processing and transport to the cellular membrane (Urban M et al., 1996 J Gen Virol 77:1537-1547). If expressed alone, gH is found exclusively in the cytoplasm and/or nuclear membrane (Cranage M P et al., 1988 J Virol 62: 1416-1422).

An exemplary HCMV gH polypeptide amino acid and nucleic acid sequence is shown below as SEQ ID NO:13 and SEQ ID NO:14, respectively. In some embodiments, a suitable gH polypeptide is substantially homologous to a known HCMV gH polypeptide. For example, a gH polypeptide may be a modified HCMV gH polypeptide containing one or more amino acid substitutions, deletions, and/or insertions as compared to a wild-type or naturally-occurring gH polypeptide (e.g., SEQ ID NO:13). Thus, in some embodiments, a gH polypeptide suitable for the present invention is substantially homologous to an HCMV gH polypeptide (SEQ ID NO:13). In some embodiments, an HCMV gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:13. In some embodiments, a gH polypeptide suitable for the present invention is substantially identical to an HCMV gH polypeptide (SEQ ID NO:13). In some embodiments, a gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:13.

```
HCMV gH Amino Acid Sequence
                                       (SEQ ID NO: 13)
MRPGLPSYLIVLAVCLLSHLLSSRYGAEAISEPLDKAFHL

LLNTYGRPIRFLRENTTQCTYNSSLRNSTVVRENAISFNF

FQSYNQYYVFHMPRCLFAGPLAEQFLNQVDLTETLERYQQ

RLNTYALVSKDLASYRSFSQQLKAQDSLGEQPTTVPPPID

LSIPHVWMPPQTTPHGWTESHTTSGLHRPHFNQTCILFDG

HDLLFSTVTPCLHQGFYLIDELRYVKITLTEDFFVVTVSI

DDDTPMLLIFGHLPRVLFKAPYQRDNFILRQTEKHELLVL

VKKDQLNRHSYLKDPDFLDAALDFNYLDLSALLRNSFHRY

AVDVLKSGRCQMLDRRTVEMAFAYALALFAAARQEEAGAQ

VSVPRALDRQAALLQIQEFMITCLSQTPPRTTLLLYPTAV

DLAKRALWTPNQITDITSLVRLVYILSKQNQQHLIPQWAL

RQIADFALKLHKTHLASFLSAFARQELYLMGSLVHSMLVH

TTERREIFIVETGLCSLAELSHFTQLLAHPHHEYLSDLYT

PCSSSGRRDHSLERLTRLFPDATVPTTVPAALSILSTMQP
```

-continued
STLETFPDLFCLPLGESFSALTVSEHVSYVVTNQYLIKGI

SYPVSTTVVGQSLIITQTDSQTKCELTRNMHTTHSITAAL

NISLENCAFCQSALLEYDDTQGVINIMYMHDSDDVLFALD

PYNEVVVSSPRTHYLMLLKNGTVLEVTDVVVDATDSRLLM

MSVYALSAIIGIYLLYRMLKTC*
(SEQ ID NO: 13) (TM and CTD underlined)

HCMV gH Nucleotide Sequence
(SEQ ID NO: 14)
ATGCGGCCAGGCCTCCCCTCCTACCTCATCGTCCTCGCCG

TCTGTCTCCTCAGCCACCTACTTTCGTCACGATATGGCGC

AGAAGCCATATCCGAACCGCTGGACAAAGCGTTTCACCTA

CTGCTCAACACCTACGGGAGACCCATCCGCTTCCTGCGTG

AAAACACCACCCAGTGTACCTACAATAGCAGCCTCCGTAA

CAGCACGGTCGTCAGGGAAAACGCCATCAGTTTCAACTTT

TTCCAAAGCTATAATCAATACTATGTATTCCATATGCCTC

GATGTCTTTTTGCGGGTCCTCTGGCGGAGCAGTTTCTGAA

CCAGGTAGATCTGACCGAAACCCTGGAAAGATACCAACAG

AGACTTAACACTTACGCGCTGGTATCCAAAGACCTGGCCA

GCTACCGATCTTTTTCGCAGCAGCTAAAGGCACAGGACAG

CCTAGGTAACAGCCCACCACTGTGCCACCACCCATTGAC

CTGTCAATACCTCACGTTTGGATGCCACCGCAAACCACTC

CACACGGCTGGACAGAATCACATACCACCTCAGGACTACA

CCGACCACACTTTAACCAGACCTGTATCCTCTTTGATGGA

CACGATCTACTATTCAGCACCGTCACACCTTGTTTGCACC

AAGGCTTTTACCTCATCGACGAACTACGTTACGTTAAAAT

AACACTGACCGAGGACTTCTTCGTAGTTACGGTGTCCATA

GACGACGACACACCCATGCTGCTTATCTTCGGCCATCTTC

CACGCGTACTCTTTAAAGCGCCCTATCAACGCGACAACTT

TATACTACGACAAACTGAAAAACACGAGCTCCTGGTGCTA

GTTAAGAAAGATCAACTGAACCGTCACTCTTATCTCAAAG

ACCCGGACTTTCTTGACGCCGACTTGACTTCAACTACCT

GGACCTCAGCGCACTACTACGTAACAGCTTTCACCGTTAC

GCCGTGGATGTACTCAAAAGCGGTCGATGTCAGATGCTGG

ACCGCCGCACGGTAGAAATGGCCTTCGCCTACGCATTAGC

ACTGTTCGCAGCAGCCCGACAAGAAGAGGCCGGCGCCCAA

GTCTCCGTCCCACGGGCCCTAGACCGCCAGGCCGCACTCT

TACAAATACAAGAATTTATGATCACCTGCCTCTCACAAAC

ACCACCACGCACCACGTTGCTGCTGTATCCCACGGCCGTG

GACCTGGCCAAACGAGCCCTTTGGACACCGAATCAGATCA

CCGACATCACCAGCCTCGTACGCCTGGTCTACATACTCTC

TAAACAGAATCAGCAACATCTCATCCCCCAGTGGGCACTA

CGACAGATCGCCGACTTTGCCCTAAAACTACACAAAACGC

ACCTGGCCTCTTTTCTTTCAGCCTTCGCGCGTCAAGAACT

CTACCTCATGGGCAGCCTCGTCCACTCCATGCTAGTACAT

ACGACGGAGAGACGCGAAATCTTCATCGTAGAAACGGGCC

TCTGTTCATTAGCCGAGCTATCACACTTTACGCAGTTGCT

AGCTCATCCGCACCACGAATACCTCAGCGACCTGTACACA

CCCTGTTCCAGTAGCGGGCGACGCGATCACTCGCTCGAAC

GCCTCACACGTCTCTTCCCCGATGCCACCGTCCCCACTAC

CGTTCCCGCCGCCCTCTCCATCCTATCTACCATGCAACCA

AGCACGCTAGAAACCTTCCCCGACCTGTTTTGTCTGCCGC

TCGGCGAATCCTTCTCCGCGCTGACCGTCTCCGAACACGT

CAGTTATGTCGTAACAAACCAGTACCTGATCAAAGGTATC

TCCTACCCTGTCTCCACCACCGTCGTAGGCCAGAGCCTCA

TCATCACCCAGACGGACAGTCAAACTAAATGCGAACTGAC

GCGCAACATGCATACCACACACAGCATCACAGCGGCGCTC

AACATTTCCCTAGAAAACTGCGCCTTTTGCCAAAGCGCCC

TACTAGAATACGACGACACGCAAGGCGTCATCAACATCAT

GTACATGCACGACTCGGACGACGTCCTTTTCGCCCTGGAT

CCCTACAACGAAGTGGTGGTCTCATCTCCGCGAACTCACT

ACCTCATGCTTTTGAAAAACGGTACGGTCCTAGAAGTAAC

TGACGTCGTCGTGGACGCTACCGACAGTCGTCTCCTCATG

ATGTCCGTCTACGCGCTATCGGCCATCATCGGCATCTATC

TGCTCTACCGCATGCTCAAGACATGCTGA
(SEQ ID NO: 14) (TM and CTD underlined)

Codon Optimized HCMV gH Nucleotide Sequence
(SEQ ID NO: 15)
ATGAGACCTGGACTGCCTTCTTATCTGATTGTGCTGGCCG

TCTGCCTGCTGTCACATCTGCTGAGTTCACGCTATGGGGC

TGAGGCTATCTCCGAGCCACTGGACAAGGCTTTTCACCTG

CTGCTGAACACCTACGGGAGACCCATTAGGTTCCTGCGCG

AGAATACCACACAGTGCACATATAACAGCTCCCTGCGGAA

CAGCACTGTGGTCCGCGAAAACGCCATCTCTTTTAATTTC

TTTCAGAGTTACAACCAGTACTACGTGTTCCATATGCCAC

GCTGTCTGTTTGCAGGACCCCTGGCCGAGCAGTTCCTGAA

CCAGGTGGACCTGACCGAGACACTGGAAAGATACCAGCAG

AGGCTGAATACCTATGCCCTGGTGAGTAAGGATCTGGCTT

CATATCGGTCTTTCAGTCAGCAGCTCAAGGCCCAGGACTC

ACTGGGCGAGCAGCCTACTACCGTGCCCCCTCCAATCGAT

CTGAGCATTCCACACGTCTGGATGCCCCCTCAGACAACTC

CCCACGGCTGGACCGAAAGCCATACCACATCCGGGCTGCA

CAGACCCCATTTAACCAGACATGCATCCTGTTTGATGGG

CACGACCTGCTGTTCAGCACTGTGACCCCTTGTCTGCATC

AGGGATTCTACCTGATCGATGAGCTGAGATATGTGAAAAT

```
                         -continued
TACACTGACTGAAGACTTCTTTGTGGTCACCGTGAGCATC

GACGATGACACACCAATGCTGCTGATTTTTGGACACCTGC

CCCGGGTGCTGTTCAAGGCCCCCTACCAGCGAGACAACTT

TATTCTGCGGCAGACCGAGAAACACGAACTGCTGGTGCTG

GTCAAGAAAGATCAGCTCAACAGGCATAGCTATCTGAAGG

ACCCCGACTTTCTGGATGCCGCTCTGGACTTCAACTACCT

GGACCTGTCAGCACTGCTGCGGAATAGCTTCCACAGATAT

GCCGTGGATGTCCTGAAATCCGGAAGATGCCAGATGCTGG

ACCGGAGAACCGTGGAGATGGCATTTGCCTACGCTCTGGC

ACTGTTCGCAGCCGCTAGGCAGGAGGAAGCAGGCGCTCAG

GTGTCCGTCCCTCGCGCACTGGATCGACAGGCAGCCCTGC

TGCAGATCCAGGAGTTCATGATTACCTGTCTGTCTCAGAC

ACCACCCAGAACTACCCTGCTGCTGTACCCCACTGCCGTG

GACCTGGCTAAGAGGGCACTGTGGACCCCTAACCAGATCA

CTGATATTACCTCTCTGGTGCGCCTGGTCTATATCCTGAG

TAAACAGAATCAGCAGCACCTGATCCCACAGTGGGCCCTG

CGACAGATTGCCGACTTCGCTCTGAAGCTGCACAAAACCC

ATCTGGCTTCCTTCCTGTCTGCATTTGCCCGCCAGGAGCT

GTACCTGATGGGCTCTCTGGTGCACAGTATGCTGGTCCAT

ACAACTGAGAGGCGCGAAATCTTTATTGTGGAGACAGGGC

TGTGCAGCCTGGCTGAACTGTCCCACTTCACTCAGCTCCT

GGCCCATCCTCACCATGAGTACCTGTCCGATCTGTATACC

CCATGTTCTAGTTCAGGCCGACGGGACCACTCTCTGGAAC

GACTGACTCGGCTGTTTCCTGATGCAACCGTGCCTACCAC

CGTGCCCGCCGCCCTGAGTATCCTGTCAACAATGCAGCCA

AGCACACTGGAGACTTTCCCCGACCTGTTTTGCCTGCCTC

TGGGGGAGTCATTCAGCGCCCTGACCGTGTCAGAACATGT

CAGCTACGTGGTCACAAACCAGTATCTGATCAAGGGAATT

TCCTACCCCGTGTCTACTACCGTGGTCGGCCAGAGTCTGA

TCATTACCCAGACAGATTCACAGACTAAATGTGAGCTGAC

CCGGAATATGCACACAACTCATAGCATCACCGCCGCTCTG

AACATTTCCCTGGAGAATTGCGCTTTTTGTCAGAGTGCAC

TGCTGGAATACGATGACACACAGGGCGTGATCAACATTAT

GTATATGCACGATAGCGATGACGTGCTGTTCGCTCTGGAC

CCCTACAACGAGGTGGTCGTGAGCTCCCCTCGCACTCATT

ATCTGATGCTGCTGAAGAATGGAACAGTGCTGGAAGTCAC

TGATGTCGTGGTCGATGCCACAGACTCCCGGCTGCTGATG

ATGTCTGTGTACGCACTGTCCGCCATCATCGGCATCTATC

TGCTGTATCGAATGCTGAAAACCTGTTGA
(SEQ ID NO: 15)  (TM and CTD underlined)
```

In some embodiments, a gH polypeptide for use in accordance with the present invention lacks a transmembrane domain and/or cytoplasmic domain and/or contains a modified transmembrane domain and/or cytoplasmic domain. A gH polypeptide may optionally include one or more additional polypeptides (e.g., a heterologous transmembrane domain and/or cytoplasmic domain polypeptide). In some embodiments, a gH polypeptide is expressed as a fusion protein with a heterologous polypeptide. The gH polypeptide can be linked to a heterologous polypeptide to create a fusion protein without altering gH function and/or antigenicity. For example, a coding sequence for a heterologous polypeptide may be spliced into the gH polypeptide coding sequence, e.g., at the 3' end of the gH polypeptide coding sequence. In some embodiments, a coding sequence for a heterologous polypeptide may be spliced in frame into the gH polypeptide coding sequence. In some embodiments, a gH polypeptide-coding sequence and heterologous polypeptide may be expressed by a single promoter. In some embodiments, a heterologous polypeptide is inserted at (e.g., fused to) the C-terminus of a gH polypeptide.

In some embodiments, a heterologous polypeptide is or comprises a transmembrane domain and/or cytoplasmic domain found in Vesicular Stomatitis Virus (VSV). In some embodiments, a gH that is lacking a transmembrane domain and/or cytoplasmic domain is fused to a transmembrane domain and/or cytoplasmic domain from VSV. An exemplary gH-VSV fusion polypeptide for use in accordance with the present invention is shown below as SEQ ID NO:16. In some embodiments, a suitable gH-VSV polypeptide fusion protein includes all or a portion of a gH polypeptide that is substantially homologous to a known HCMV gH polypeptide and all or a portion of a VSV polypeptide that is substantially homologous to a known VSV polypeptide. For example, a gH—VSV polypeptide fusion protein may contain one or more amino acid substitutions, deletions, and/or insertions as compared to a wild-type or naturally-occurring gH and/or VSV polypeptide. Thus, in some embodiments, a gH-VSV polypeptide fusion protein suitable for the present invention is substantially homologous to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:16. In some embodiments, a gH-VSV polypeptide fusion protein suitable for the present invention is substantially identical to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16. As used herein, "gH-G" refers to a HMCV gH—VSV TM/CTD fusion protein.

```
HCMV gH-G Amino Acid Sequence
                                        (SEQ ID NO: 16)
MRPGLPSYLIVLAVCLLSHLLSSRYGAEAISEPLDKAFHL

LLNTYGRPIRFLRENTTQCTYNSSLRNSTVVRENAISFNF

FQSYNQYYVFHMPRCLFAGPLAEQFLNQVDLTETLERYQQ

RLNTYALVSKDLASYRSFSQQLKAQDSLGEQPTTVPPPID

LSIPHVWMPPQTTPHGWTESHTTSGLHRPHFNQTCILFDG

HDLLFSTVTPCLHQGFYLIDELRYVKITLTEDFFVVTVSI

DDDTPMLLIFGHLPRVLFKAPYQRDNFILRQTEKHELLVL
```

-continued
VKKDQLNRHSYLKDPDFLDAALDFNYLDLSALLRNSFHRY

AVDVLKSGRCQMLDRRTVEMAFAYALALFAAARQEEAGAQ

VSVPRALDRQAALLQIQEFMITCLSQTPPRTTLLLYPTAV

DLAKRALWTPNQITDITSLVRLVYILSKQNQQHLIPQWAL

RQIADFALKLHKTHLASFLSAFARQELYLMGSLVHSMLVH

TTERREIFIVETGLCSLAELSHFTQLLAHPHHEYLSDLYT

PCSSSGRRDHSLERLTRLFPDATVPTTVPAALSILSTMQP

STLETFPDLFCLPLGESFSALTVSEHVSYVVTNQYLIKGI

SYPVSTTVVGQSLIITQTDSQTKCELTRNMHTTHSITAAL

NISLENCAFCQSALLEYDDTQGVINIMYMHDSDDVLFALD

PYNEVVVSSPRTHYLMLLKNGTVLEVTDVVVDATDSR<u>FFF</u>

<u>IIGLIIGLFLVLRVGIHLCIKLKHTKKRQIYTDIEMNRLG</u>

<u>K</u>*
(SEQ ID NO: 16)
(TM and CTD underlined)

HCMV gH-G Nucleotide Sequence
(SEQ ID NO: 17)
ATGCGGCCAGGCCTCCCCTCCTACCTCATCGTCCTCGCCG

TCTGTCTCCTCAGCCACCTACTTTCGTCACGATATGGCGC

AGAAGCCATATCCGAACCGCTGGACAAAGCGTTTCACCTA

CTGCTCAACACCTACGGGAGACCCATCCGCTTCCTGCGTG

AAAACACCACCCAGTGTACCTACAATAGCAGCCTCCGTAA

CAGCACGGTCGTCAGGGAAAACGCCATCAGTTTCAACTTT

TTCCAAAGCTATAATCAATACTATGTATTCCATATGCCTC

GATGTCTTTTTGCGGGTCCTCTGGCGGAGCAGTTTCTGAA

CCAGGTAGATCTGACCGAAACCCTGGAAAGATACCAACAG

AGACTTAACACTTACGCGCTGGTATCCAAAGACCTGGCCA

GCTACCGATCTTTTTCGCAGCAGCTAAAGGCACAGGACAG

CCTAGGTGAACAGCCCACCACTGTGCCACCACCCATTGAC

CTGTCAATACCTCACGTTTGGATGCCACCGCAAACCACTC

CACACGGCTGGACAGAATCACATACCACCTCAGGACTACA

CCGACCACACTTTAACCAGACCTGTATCCTCTTTGATGGA

CACGATCTACTATTCAGCACCGTCACACCTTGTTTGCACC

AAGGCTTTTACCTCATCGACGAACTACGTTACGTTAAAAT

AACACTGACCGAGGACTTCTTCGTAGTTACGGTGTCCATA

GACGACGACACACCCATGCTGCTTATCTTCGGCCATCTTC

CACGCGTACTCTTTAAAGCGCCCTATCAACGCGACAACTT

TATACTACGACAAACTGAAAAACACGAGCTCCTGGTGCTA

GTTAAGAAAGATCAACTGAACCGTCACTCTTATCTCAAAG

ACCCGGACTTTCTTGACGCCGCACTTGACTTCAACTACCT

GGACCTCAGCGCACTACTACGTAACAGCTTTCACCGTTAC

GCCGTGGATGTACTCAAAAGCGGTCGATGTCAGATGCTGG

ACCGCCGCACGGTAGAAATGGCCTTCGCCTACGCATTAGC

ACTGTTCGCAGCAGCCCGACAAGAAGAGGCCGGCGCCCAA

GTCTCCGTCCCACGGGCCCTAGACCGCCAGGCCGCACTCT

TACAAATACAAGAATTTATGATCACCTGCCTCTCACAAAC

ACCACCACGCACCACGTTGCTGCTGTATCCCACGGCCGTG

GACCTGGCCAAACGAGCCCTTTGGACACCGAATCAGATCA

CCGACATCACCAGCCTCGTACGCCTGGTCTACATACTCTC

TAAACAGAATCAGCAACATCTCATCCCCCAGTGGGCACTA

CGACAGATCGCCGACTTTGCCCTAAAACTACACAAAACGC

ACCTGGCCTCTTTTCTTTCAGCCTTCGCGCGTCAAGAACT

CTACCTCATGGGCAGCCTCGTCCACTCCATGCTAGTACAT

ACGACGGAGAGACGCGAAATCTTCATCGTAGAAACGGGCC

TCTGTTCATTAGCCGAGCTATCACACTTTACGCAGTTGCT

AGCTCATCCGCACCACGAATACCTCAGCGACCTGTACACA

CCCTGTTCCAGTAGCGGGCGACGCGATCACTCGCTCGAAC

GCCTCACACGTCTCTTCCCCGATGCCACCGTCCCCACTAC

CGTTCCCGCCGCCCTCTCCATCCTATCTACCATGCAACCA

AGCACGCTAGAAACCTTCCCCGACCTGTTTTGTCTGCCGC

TCGGCGAATCCTTCTCCGCGCTGACCGTCTCCGAACACGT

CAGTTATGTCGTAACAAACCAGTACCTGATCAAAGGTATC

TCCTACCCTGTCTCCACCACCGTCGTAGGCCAGAGCCTCA

TCATCACCCAGACGGACAGTCAAACTAAATGCGAACTGAC

GCGCAACATGCATACCACACACAGCATCACAGCGGCGCTC

AACATTTCCCTAGAAAACTGCGCCTTTTGCCAAAGCGCCC

TACTAGAATACGACGACACGCAAGGCGTCATCAACATCAT

GTACATGCACGACTCGGACGACGTCCTTTTCGCCCTGGAT

CCCTACAACGAAGTGGTGGTCTCATCTCCGCGAACTCACT

ACCTCATGCTTTTGAAAAACGGTACGGTCCTAGAAGTAAC

TGACGTCGTCGTGGACGCTACCGACAGTCGT<u>TTTTTTCTTT</u>

<u>ATCATAGGGTTAATCATTGGACTATTCTTGGTTCTCCGAG</u>

<u>TTGGTATCCATCTTTGCATTAAATTAAAGCACACCAAGAA</u>

<u>AAGACAGATTTATACAGACATAGAGATGAACCGACTTGGA</u>

<u>AAGTAA</u>
(SEQ ID NO: 17) (TM and CTD underlined)

Codon Optimized HCMV gH-G Nucleotide Sequence
(SEQ ID NO: 18)
ATGCGACCCGGACTGCCAAGCTACCTGATTGTCCTGGCTG

TCTGTCTGCTGTCACACCTGCTGAGTTCAAGATATGGGGC

CGAAGCCATCAGCGAGCCACTGGACAAGGCTTTCCACCTG

CTGCTGAACACCTACGGCAGACCCATTAGGTTTCTGCGCG

AGAATACCACACAGTGCACATATAACAGCTCCCTGAGGAA

TAGCACTGTGGTCCGCGAAAACGCCATCTCTTTCAATTTC

TTTCAGAGTTACAACCAGTACTACGTGTTCCATATGCCAC

-continued

```
GCTGTCTGTTCGCAGGACCCCTGGCCGAGCAGTTTCTGAA
CCAGGTGGACCTGACCGAGACACTGGAAAGATACCAGCAG
AGGCTGAATACCTATGCCCTGGTGAGTAAGGATCTGGCTT
CATATCGGTCTTTCAGTCAGCAGCTCAAGGCCCAGGACTC
TCTGGGAGAGCAGCCTACTACCGTGCCCCCTCCAATCGAT
CTGAGTATTCCACACGTCTGGATGCCCCCTCAGACAACTC
CCCACGGATGGACCGAAAGCCATACCACATCCGGCCTGCA
CAGACCCCACTTCAACCAGACATGCATCCTGTTCGATGGC
CACGACCTGCTGTTTTCCACTGTGACCCCTTGTCTGCATC
AGGGGTTCTACCTGATCGATGAGCTGAGATATGTGAAGAT
TACACTGACTGAAGACTTCTTTGTGGTCACCGTGTCTATC
GACGATGACACACCAATGCTGCTGATTTTCGGACACCTGC
CCCGGGTGCTGTTCAAGGCCCCCTACCAGCGAGACAACTT
CATCCTGCGGCAGACCGAGAAACACGAACTGCTGGTGCTG
GTCAAGAAAGATCAGCTCAACCGGCATTCCTATCTGAAGG
ACCCCGACTTCCTGGATGCCGCTCTGGACTTTAACTACCT
GGACCTGTCAGCACTGCTGCGGAATAGCTTTCACAGATAT
GCCGTGGATGTCCTGAAATCTGGGCGCTGCCAGATGCTGG
ACCGGAGAACCGTGGAGATGGCATTCGCCTACGCTCTGGC
ACTGTTTGCAGCCGCTCGGCAGGAGGAAGCAGGAGCTCAG
GTGAGTGTCCCTCGCGCACTGGATCGACAGGCAGCCCTGC
TGCAGATCCAGGAGTTCATGATTACCTGTCTGAGCCAGAC
ACCACCCAGAACTACCCTGCTGCTGTACCCCACTGCCGTG
GACCTGGCTAAGAGGGCACTGTGGACCCCTAACCAGATCA
CTGATATTACCAGCCTGGTGAGACTGGTCTATATCCTGTC
CAAACAGAATCAGCAGCACCTGATCCCACAGTGGGCCCTG
AGGCAGATTGCCGACTTTGCTCTGAAGCTGCACAAAACCC
ATCTGGCTTCCTTTCTGTCTGCATTCGCCAGACAGGAGCT
GTACCTGATGGGATCTCTGGTGCACAGTATGCTGGTCCAT
ACAACTGAGAGGCGCGAAATCTTCATTGTGGAGACAGGCC
TGTGCAGCCTGGCTGAACTGTCCCACTTTACTCAGCTCCT
GGCCCATCCTCACCATGAGTACCTGTCAGATCTGTATACC
CCATGTTCTAGTTCAGGACGACGGGACCACAGCCTGGAAC
GACTGACTCGGCTGTTCCCTGATGCAACCGTGCCTACCAC
CGTGCCCGCCGCCCTGAGTATCCTGTCAACAATGCAGCCA
AGCACACTGGAGACTTTTCCCGACCTGTTCTGCCTGCCTC
TGGGCGAGAGCTTCAGCGCCCTGACCGTGAGCGAACATGT
CAGCTACGTGGTCACAAACCAGTATCTGATCAAGGGGATT
TCCTACCCCGTGTCTACTACCGTGGTCGGACAGTCCCTGA
TCATTACCCAGACAGATTCTCAGACTAAATGTGAGCTGAC
```

-continued

```
CAGAAATATGCACACAACTCATAGTATCACCGCCGCTCTG
AACATTTCACTGGAGAATTGCGCTTTCTGTCAGTCCGCAC
TGCTGGAATACGATGACACACAGGGCGTGATCAACATTAT
GTATATGCACGATTCTGATGACGTGCTGTTTGCTCTGGAC
CCCTACAACGAGGTGGTCGTGAGCTCCCCCAGAACTCATT
ATCTGATGCTGCTGAAGAATGGCACAGTGCTGGAAGTCAC
TGATGTCGTGGTCGATGCCACAGACTCCCGCTTCTTTTTC
ATCATTGGCCTGATCATTGGGCTGTTCCTGGTGCTGCGAG
TCGGCATCCACCTGTGCATCAAGCTGAAGCATACAAAGAA
GAGACAGATCTACACCGATATTGAAATGAACAGGCTGGGC
AAATGA
```

(SEQ ID NO: 18) (TM and CTD underlined)

In some embodiments, a gH polypeptide includes a transmembrane domain and/or cytoplasmic domain found in gB. An exemplary nucleotide encoding an HCMV gH—HCMV gB TM/CTD fusion polypeptide for use in accordance with the present invention is shown below as SEQ ID NO:20. In some embodiments, an HCMV gH—HCMV gB TM/CTD polypeptide suitable for the present invention is substantially homologous to the polypeptide encoded by SEQ ID NO:20. In some embodiments, an HCMV gH—HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to the polypeptide encoded by SEQ ID NO:20. In some embodiments, an HCMV gH—HCMV gB TM/CTD polypeptide suitable for the present invention is substantially identical to the polypeptide encoded by SEQ ID NO:20. In some embodiments, an HCMV gH—HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to the polypeptide encoded by SEQ ID NO:20.

HCMV gH-HCMV gB TM/CTD Nucleotide Sequence
(SEQ ID NO: 20)

```
ATGCGGCCAGGCCTCCCCTCCTACCTCATCGTCCTCGCCG
TCTGTCTCCTCAGCCACCTACTTTCGTCACGATATGGCGC
AGAAGCCATATCCGAACCGCTGGACAAAGCGTTTCACCTA
CTGCTCAACACCTACGGGAGACCCATCCGCTTCCTGCGTG
AAAACACCACCCAGTGTACCTACAATAGCAGCCTCCGTAA
CAGCACGGTCGTCAGGGAAAACGCCATCAGTTTCAACTTT
TTCCAAAGCTATAATCAATACTATGTATTCCATATGCCTC
GATGTCTTTTTGCGGGTCCTCTGGCGGAGCAGTTTCTGAA
CCAGGTAGATCTGACCGAAACCCTGGAAAGATACCAACAG
AGACTTAACACTTACGCGCTGGTATCCAAAGACCTGGCCA
GCTACCGATCTTTTCGCAGCAGCTAAAGGCACAGGACAG
CCTAGGTGAACAGCCCACCACTGTGCCACCACCCATTGAC
CTGTCAATACCTCACGTTTGGATGCCACCGCAAACCACTC
```

-continued

```
CACACGGCTGGACAGAATCACATACCACCTCAGGACTACA
CCGACCACACTTTAACCAGACCTGTATCCTCTTTGATGGA
CACGATCTACTATTCAGCACCGTCACACCTTGTTTGCACC
AAGGCTTTTACCTCATCGACGAACTACGTTACGTTAAAAT
AACACTGACCGAGGACTTCTTCGTAGTTACGGTGTCCATA
GACGACGACACACCCATGCTGCTTATCTTCGGCCATCTTC
CACGCGTACTCTTTAAAGCGCCCTATCAACGCGACAACTT
TATACTACGACAAACTGAAAAACACGAGCTCCTGGTGCTA
GTTAAGAAAGATCAACTGAACCGTCACTCTTATCTCAAAG
ACCCGGACTTTCTTGACGCCGCACTTGACTTCAACTACCT
GGACCTCAGCGCACTACTACGTAACAGCTTTCACCGTTAC
GCCGTGGATGTACTCAAAAGCGGTCGATGTCAGATGCTGG
ACCGCCGCACGGTAGAAATGGCCTTCGCCTACGCATTAGC
ACTGTTCGCAGCAGCCCGACAAGAAGAGGCCGGCGCCCAA
GTCTCCGTCCCACGGGCCCTAGACCGCCAGGCCGCACTCT
TACAAATACAAGAATTTATGATCACCTGCCTCTCACAAAC
ACCACCACGCACCACGTTGCTGCTGTATCCCACGGCCGTG
GACCTGGCCAAACGAGCCCTTTGGACACCGAATCAGATCA
CCGACATCACCAGCCTCGTACGCCTGGTCTACATACTCTC
TAAACAGAATCAGCAACATCTCATCCCCCAGTGGGCACTA
CGACAGATCGCCGACTTTGCCCTAAAACTACACAAAACGC
ACCTGGCCTCTTTTCTTTCAGCCTTCGCGCGTCAAGAACT
CTACCTCATGGGCAGCCTCGTCCACTCCATGCTAGTACAT
ACGACGGAGAGACGCGAAATCTTCATCGTAGAAACGGGCC
TCTGTTCATTAGCCGAGCTATCACACTTTACGCAGTTGCT
AGCTCATCCGCACCACGAATACCTCAGCGACCTGTACACA
CCCTGTTCCAGTAGCGGGCGACGCGATCACTCGCTCGAAC
GCCTCACACGTCTCTTCCCCGATGCCACCGTCCCCACTAC
CGTTCCCGCCGCCCTCTCCATCCTATCTACCATGCAACCA
AGCACGCTAGAAACCTTCCCCGACCTGTTTTGTCTGCCGC
TCGGCGAATCCTTCTCCGCGCTGACCGTCTCCGAACACGT
CAGTTATGTCGTAACAAACCAGTACCTGATCAAAGGTATC
TCCTACCCTGTCTCCACCACCGTCGTAGGCCAGAGCCTCA
TCATCACCCAGACGGACAGTCAAACTAAATGCGAACTGAC
GCGCAACATGCATACCACACACAGCATCACAGCGGCGCTC
AACATTTCCCTAGAAAACTGCGCCTTTTGCCAAAGCGCCC
TACTAGAATACGACGACACGCAAGGCGTCATCAACATCAT
GTACATGCACGACTCGGACGACGTCCTTTTCGCCCTGGAT
CCCTACAACGAAGTGGTGGTCTCATCTCCGCGAACTCACT
ACCTCATGCTTTTGAAAAACGGTACGGTCCTAGAAGTAAC
TGACGTCGTCGTGGACGCTACCGACAGTCGTTTCGGAGCC
TTCACCATCATCCTCGTGGCCATAGCCGTCGTCATTATCA
TTTATTTGATCTATACTCGACAGCGGCGTCTCTGCATGCA
GCCGCTGCAGAACCTCTTTCCCTATCTGGTGTCCGCCGAC
GGGACCACCGTGACGTCGGGCAACACCAAAGACACGTCGT
TACAGGCTCCGCCTTCCTACGAGGAAAGTGTTTATAATTC
TGGTCGCAAAGGACCGGGACCACCGTCGTCTGATGCATCC
ACGGCGGCTCCGCCTTACACCAACGAGCAGGCTTACCAGA
TGCTTCTGGCCCTGGTCCGTCTGGACGCAGAGCAGCGAGC
GCAGCAGAACGGTACAGATTCTTTGGACGGACAGACTGGC
ACGCAGGACAAGGGACAGAAGCCCAACCTGCTAGACCGAC
TGCGACACCGCAAAAACGGCTACCGACACTTGAAAGACTC
CGACGAAGAAGAGAACGTCTGA
(SEQ ID NO: 20)
(gH peptide signal underlined;
gB TM-CTD bolded)
```

Others (including gN and gM—Glycoprotein Complex (gC) II)

In addition to gB and gH, other envelope glycoproteins may be useful in vaccine development. For example, the gcII complex, containing gN (UL73) and gM (UL100), is of particular interest. Proteomic analyses of HCMV virions has demonstrated that gcII is the most abundantly expressed glycoprotein in virus particles, emphasizing its potential importance in protective immunity (Varnum S M et al., 2005 Human Gene Ther 16:1143-50). HCMV infection elicits a gcII-specific antibody response in a majority of seropositive individuals (Shimamura M et al., 2006 J Virol 80:4591-600), and DNA vaccines containing gcII antigens gM and gN have been shown to elicit neutralizing antibody responses in rabbits and mice (Shen S et al., 2007 Vaccine 25:3319-27).

pp65

The cellular immune response to HCMV includes MHC class II restricted $CD4^+$ and MHC class I restricted, cytotoxic $CD8^+$ T-lymphocyte responses to a number of viral antigens, many of which are found in the viral tegument, the region of the viral particle that lies between the envelope and nucleocapsid. For example, HCMV pp65 protein (UL83) has been shown to elicit a significant $CD8^+$ T-lymphocyte response following HCMV infection (McLaughlin-Taylor E 1994 J Med Virol 43:103-10). This 65 kDa viral protein is one of the most abundantly expressed structural proteins of HCMV. Exemplary pp65 sequences are described herein.

Others (including IE1, pp150)

Other proteins that elicit T-lymphocyte responses include the immediate early-1 (IE1) protein (UL123) and pp150 (UL32) (Gibson L et al., 2004 J Immunol 172:2256-64; La Rosa C et al., 2005 Human Immunol 66:116-26).

As described above, a Gag polypeptide may optionally include one or more additional polypeptides (e.g., a heterologous antigen). In some embodiments, a Gag polypeptide is co-expressed with a heterologous antigen (e.g., under separate promoters and/or as separate proteins). The Gag polypeptide can be co-expressed with a heterologous antigen without altering Gag function. Without wishing to be bound by any theory, it is thought that co-expression of a self-assembling Gag polypeptide with a heterologous envelope antigen will allow the antigen to be incorporated into the envelope or lipid bilayer of a resulting VLP. In some embodiments, VLP envelope components serve as effective immunogens (e.g., for induction of humoral immune response). In some embodiments, a Gag polypeptide is expressed as a fusion protein with a heterologous antigen. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen will allow the antigen to be incorporated into the structural components of a resulting VLP. In some embodiments, VLP structural components serve as effective immunogens (e.g., for induction of cellular immune response). For example, provided VLPs may comprise a retroviral gag polypeptide (e.g., MLV gag) and a structural component of HCMV (e.g., pp65). In some such embodiments, pp65 is incorporated into the VLP and serves as an antigen for eliciting an immune response against HCMV.

Provided VLPs may contain a structural retroviral protein (e.g., Gag polypeptide) that is arranged and constructed such that it self-assembles to form the VLP and is positioned in the VLP interior. In some embodiments, provided VLPs contain an envelope protein (e.g., gB and/or gH) that is arranged and constructed such that one or more epitopes of the envelope protein (e.g., gB and/or gH) is positioned on the VLP surface. In some embodiments, provided VLPs contain a fusion structural protein (e.g., Gag/pp65) that is arranged and constructed such that one or more epitopes of the structural protein (e.g., pp65) is positioned in the VLP interior.

II. Production of VLPs

It will be appreciated that a composition comprising VLPs will typically include a mixture of VLPs with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate VLP formation and/or to alter VLP size. In some embodiments, filtration, dialysis and/or centrifugation may be used to adjust the VLP size distribution.

In general, VLPs produced in accordance with the methods of the present disclosure may be of any size. In certain embodiments, the composition may include VLPs with diameter in range of about 20 nm to about 300 nm. In some embodiments, a VLP is characterized in that it has a diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs within a population show an average diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs in a population have a polydispersity index that is less than 0.5 (e.g., less than 0.45, less than 0.4, or less than 0.3). In some embodiments, VLP diameter is determined by nanosizing. In some embodiments, VLP diameter is determined by electron microscopy.

A. In vitro/Ex vivo VLP production

Provided VLPs in accordance with the present invention may be prepared according to general methodologies known to the skilled person. For example, various nucleic acid molecules, genomes or reconstituted vectors or plasmids may be prepared using sequences of known viruses. Such sequences are available from banks, and material may be obtained from various collections, published plasmids, etc. These elements can be isolated and manipulated using techniques well known to the skilled artisan, or isolated from plasmids available in the art. Various synthetic or artificial sequences may also be produced from computer analysis or through (high throughput) screening of libraries. Recombinant expression of the polypeptides for VLPs requires construction of an expression vector containing a polynucleotide that encodes one or more polypeptide(s). Once a polynucleotide encoding one or more polypeptides has been obtained, the vector for production of the polypeptide may be produced by recombinant DNA technology using techniques known in the art. Expression vectors that may be utilized in accordance with the present invention include, but are not limited to mammalian expression vectors, baculovirus expression vectors, plant expression vectors (e.g., Cauliflower Mosaic Virus (CaMV), Tobacco Mosaic Virus (TMV)), plasmid expression vectors (e.g., Ti plasmid), among others.

An exemplary VLP expression plasmid that may be used in accordance with the present invention is shown below as SEQ ID NO:19:

Propol II Expression Plasmid
(SEQ ID NO: 19)
CTAGAGAGCTTGGCCCATTGCATACGTTGTATCCATATCA

TAATATGTACATTTATATTGGCTCATGTCCAACATTACCG

CCATGTTGACATTGATTATTGACTAGTTATTAATAGTAAT

CAATTACGGGGTCATTAGTTCATAGCCCATATATGGAGTT

CCGCGTTACATAACTTACGGTAAATGGCCCGCCTGGCTGA

CCGCCCAACGACCCCCGCCCATTGACGTCAATAATGACGT

ATGTTCCCATAGTAACGCCAATAGGGACTTTCCATTGACG

TCAATGGGTGGAGTATTTACGGTAAACTGCCCACTTGGCA

GTACATCAAGTGTATCATATGCCAAGTACGCCCCCTATTG

ACGTCAATGACGGTAAATGGCCCGCCTGGCATTATGCCCA

GTACATGACCTTATGGGACTTTCCTACTTGGCAGTACATC

TACGTATTAGTCATCGCTATTACCATGGTGATGCGGTTTT

GGCAGTACATCAATGGGCGTGGATAGCGGTTTGACTCACG

GGGATTTCCAAGTCTCCACCCCATTGACGTCAATGGGAGT

TTGTTTTGGCACCAAAATCAACGGGACTTTCCAAAATGTC

GTAACAACTCCGCCCCATTGACGCAAATGGGCGGTAGGCG

TGTACGGTGGGAGGTCTATATAAGCAGAGCTCGTTTAGTG

AACCGTCAGATCGCCTGGAGACGCCATCCACGCTGTTTTG

ACCTCCATAGAAGACACCGGGACCGATCCAGCCTCCGGTC

-continued
```
GACCGATCCTGAGAACTTCAGGGTGAGTTTGGGGACCCTT
GATTGTTCTTTCTTTTTCGCTATTGTAAAATTCATGTTAT
ATGGAGGGGGCAAAGTTTTCAGGGTGTTGTTTAGAATGGG
AAGATGTCCCTTGTATCACCATGGACCCTCATGATAATTT
TGTTTCTTTCACTTTCTACTCTGTTGACAACCATTGTCTC
CTCTTATTTTCTTTTCATTTTCTTGTAACTTTTTCGTTAA
ACTTTAGCTTGCATTTGTAACGAATTTTTAAATTCACTTT
TGTTTATTTGTCAGATTGTAAGTACTTTCTCTAATCACTT
TTTTTTCAAGGCAATCAGGGTATATTATATTGTACTTCAG
CACAGTTTTAGAGAACAATTGTTATAATTAAATGATAAGG
TAGAATATTTCTGCATATAAATTCTGGCTGGCGTGGAAAT
ATTCTTATTGGTAGAAACAACTACATCCTGGTCATCATCC
TGCCTTTCTCTTTATGGTTACAATGATATACACTGTTTGA
GATGAGGATAAAATACTCTGAGTCCAAACCGGGCCCCTCT
GCTAACCATGTTCATGCCTTCTTCTTTTTCCTACAGCTCC
TGGGCAACGTGCTGGTTATTGTGCTGTCTCATCATTTTGG
CAAAGAATTCCTCGAGCGTACGCCAGGGGATCCAGCGCT
ATTTAAATGCTAGCATGCATGTTAACCCTGCAGGGGTACC
GCGGCCGCAAGCTTAGATCCGTCGAGGAATTCACTCCTCA
GGTGCAGGCTGCCTATCAGAAGGTGGTGGCTGGTGTGGCC
AATGCCCTGGCTCACAAATACCACTGAGATCTTTTTCCCT
CTGCCAAAAATTATGGGACATCATGAAGCCCCTTGAGCA
TCTGACTTCTGGCTAATAAAGGAAATTTATTTTCATTGCA
ATAGTGTGTTGGAATTTTTTGTGTCTCTCACTCGGAAGGA
CATATGGGAGGGCAAATCATTTAAAACATCAGAATGAGTA
TTTGGTTTAGAGTTTGGCAACATATGCCCATATGCTGGCT
GCCATGAACAAAGGTTGGCTATAAAGAGGTCATCAGTATA
TGAAACAGCCCCCTGCTGTCCATTCCTTATTCCATAGAAA
AGCCTTGACTTGAGGTTAGATTTTTTTATATTTTGTTTT
GTGTTATTTTTTCTTTAACATCCCTAAAATTTTCCTTAC
ATGTTTTACTAGCCAGATTTTCCTCCTCTCCTGACTACT
CCCAGTCATAGCTGTCCCTCTTCTCTTATGGAGATCCCTC
GACGGATCGGCCGCAATTCGTAATCATGTCATAGCTGTTT
CCTGTGTGAAATTGTTATCCGCTCACAATTCCACACAACA
TACGAGCCGGAAGCATAAAGTGTAAAGCCTGGGGTGCCTA
ATGAGTGAGCTAACTCACATTAATTGCGTTGCGCTCACTG
CCCGCTTTCCAGTCGGGAAACCTGTCGTGCCAGCTGCATT
AATGAATCGGCCAACGCGCGGGGAGAGGCGGTTTGCGTAT
TGGGCGCTCTTCCGCTTCCTCGCTCACTGACTCGCTGCGC
TCGGTCGTTCGGCTGCGGCGAGCGGTATCAGCTCACTCAA
AGGCGGTAATACGGTTATCCACAGAATCAGGGGATAACGC
```

-continued
```
AGGAAAGAACATGTGAGCAAAAGGCCAGCAAAAGGCCAGG
AACCGTAAAAAGGCCGCGTTGCTGGCGTTTTTCCATAGGC
TCCGCCCCCCTGACGAGCATCACAAAAATCGACGCTCAAG
TCAGAGGTGGCGAAACCCGACAGGACTATAAAGATACCAG
GCGTTTCCCCCTGGAAGCTCCCTCGTGCGCTCTCCTGTTC
CGACCCTGCCGCTTACCGGATACCTGTCCGCCTTTCTCCC
TTCGGGAAGCGTGGCGCTTTCTCATAGCTCACGCTGTAGG
TATCTCAGTTCGGTGTAGGTCGTTCGCTCCAAGCTGGGCT
GTGTGCACGAACCCCCCGTTCAGCCCGACCGCTGCGCCTT
ATCCGGTAACTATCGTCTTGAGTCCAACCCGGTAAGACAC
GACTTATCGCCACTGGCAGCAGCCACTGGTAACAGGATTA
GCAGAGCGAGGTATGTAGGCGGTGCTACAGAGTTCTTGAA
GTGGTGGCCTAACTACGGCTACACTAGAAGAACAGTATTT
GGTATCTGCGCTCTGCTGAAGCCAGTTACCTTCGGAAAAA
GAGTTGGTAGCTCTTGATCCGGCAAACAAACCACCGCTGG
TAGCGGTGGTTTTTTTGTTTGCAAGCAGCAGATTACGCGC
AGAAAAAAAGGATCTCAAGAAGATCCTTTGATCTTTTCTA
CGGGGTCTGACGCTCAGTGGAACGAAAACTCACGTTAAGG
GATTTTGGTCATGAGATTATCAAAAAGGATCTTCACCTAG
ATCCTTTTAAATTAAAAATGAAGTTTTAAATCAATCTAAA
GTATATATGAGTAAACTTGGTCTGACAGTTACCAATGCTT
AATCAGTGAGGCACCTATCTCAGCGATCTGTCTATTTCGT
TCATCCATAGTTGCCTGACTCCCCGTCGTGTAGATAACTA
CGATACGGGAGGGCTTACCATCTGGCCCCAGTGCTGCAAT
GATACCGCGAGACCCACGCTCACCGGCTCCAGATTTATCA
GCAATAAACCAGCCAGCCGGAAGGGCCGAGCGCAGAAGTG
GTCCTGCAACTTTATCCGCCTCCATCCAGTCTATTAATTG
TTGCCGGGAAGCTAGAGTAAGTAGTTCGCCAGTTAATAGT
TTGCGCAACGTTGTTGCCATTGCTACAGGCATCGTGGTGT
CACGCTCGTCGTTTGGTATGGCTTCATTCAGCTCCGGTTC
CCAACGATCAAGGCGAGTTACATGATCCCCCATGTTGTGC
AAAAAAGCGGGTTAGCTCCTTCGGTCCTCCGATCGTTGTC
AGAAGTAAGTTGGCCGCAGTGTTATCACTCATGGTTATGG
CAGCACTGCATAATTCTCTTACTGTCATGCCATCCGTAAG
ATGCTTTTCTGTGACTGGTGAGTACTCAACCAAGTCATTC
TGAGAATAGTGTATGCGGCGACCGAGTTGCTCTTGCCCGG
CGTCAATACGGGATAATACCGCGCCACATAGCAGAACTTT
AAAAGTGCTCATCATTGGAAAACGTTCTTCGGGGCGAAAA
CTCTCAAGGATCTTACCGCTGTTGAGATCCAGTTCGATGT
AACCCACTCGTGCACCCAACTGATCTTCAGCATCTTTTAC
```

```
-continued
TTTCACCAGCGTTTCTGGGTGAGCAAAAACAGGAAGGCAA

AATGCCGCAAAAAAGGGAATAAGGGCGACACGGAAATGTT

GAATACTCATACTCTTCCTTTTTCAATATTATTGAAGCAT

TTATCAGGGTTATTGTCTCATGAGCGGATACATATTTGAA

TGTATTTAGAAAAATAAACAAATAGGGGTTCCGCGCACAT

TTCCCCGAAAAGTGCCACCTAAATTGTAAGCGTTAATATT

TTGTTAAAATTCGCGTTAAATTTTTGTTAAATCAGCTCAT

TTTTTAACCAATAGGCCGAAATCGGCAAAATCCCTTATAA

ATCAAAAGAATAGACCGAGATAGGGTTGAGTGTTGTTCCA

GTTTGGAACAAGAGTCCACTATTAAAGAACGTGGACTCCA

ACGTCAAAGGGCGAAAAACCGTCTATCAGGGCGATGGCCC

ACTACGTGAACCATCACCCTAATCAAGTTTTTTGGGGTCG

AGGTGCCGTAAAGCACTAAATCGGAACCCTAAAGGGAGCC

CCCGATTTAGAGCTTGACGGGAAAGCCGGCGAACGTGGC

GAGAAAGGAAGGGAAGAAAGCGAAAGGAGCGGGCGCTAGG

GCGCTGGCAAGTGTAGCGGTCACGCTGCGCGTAACCACCA

CACCCGCCGCGCTTAATGCGCCGCTACAGGGCGCGTCCCA

TTCGCCATTCAGGCTGCGCAACTGTTGGGAAGGGCGATCG

GTGCGGGCCTCTTCGCTATTACGCCAGCTGGCGAAAGGGG

GATGTGCTGCAAGGCGATTAAGTTGGGTAACGCCAGGGTT

TTCCCAGTCACGACGTTGTAAAACGACGGCCAGTGAGCGC

GCGTAATACGACTCACTATAGGGCGAATTGGAGCTCCACC

GCGGTGGCGGCCGCT
(SEQ ID NO: 19)
```

Provided VLPs may be prepared according to techniques known in the art. For example, in some embodiments, provided VLPs may be produced in any available protein expression system. Typically, the expression vector is transferred to a host cell by conventional techniques and the transfected cells are then cultured by conventional techniques to produce VLPs. In some embodiments, VLPs are produced using transient transfection of cells. In some embodiments, VLPs are produced using stably transfected cells. Typical cell lines that may be utilized for VLP production include, but are not limited to, mammalian cell lines such as human embryonic kidney (HEK) 293, WI 38, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells+/−DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); MRC 5 cells; FS4 cells; and a human hepatoma line (Hep G2). In some embodiments, cell lines that may be utilized for VLP production include insect (e.g., Sf-9, Sf-21, Tn-368, Hi5) or plant (e.g., Leguminosa, cereal, or tobacco) cells. It will be appreciated in some embodiments, particularly when glycosylation is important for protein function, mammalian cells are preferable for protein expression and/or VLP production (see, e.g., Roldao A et al., 2010 Expt Rev Vaccines 9:1149-76).

It will be appreciated that a cell strain may be chosen which modulates the expression of the inserted sequences, or modifies and processes the gene product in a specific way. Such modifications (e.g., glycosylation) and processing (e.g., cleavage or transport to the membrane) of protein products may be important for generation of a VLP or function of a VLP polypeptide or additional polypeptide (e.g., an adjuvant or additional antigen). Different cells have characteristic and specific mechanisms for post-translational processing and modification of proteins and gene products. Appropriate cell lines or host systems can be chosen to ensure the correct modification and processing of the foreign protein expressed. Generally, eukaryotic host cells (also referred to as packaging cells (e.g., 293T human embryo kidney cells) which possess appropriate cellular machinery for proper processing of the primary transcript, glycosylation and phosphorylation of the gene product may be used in accordance with the present invention.

VLPs may be purified according to known techniques, such as centrifugation, gradients, sucrose-gradient ultracentrifugation, tangential flow filtration and chromatography (e.g., ion exchange (anion and cation), affinity and sizing column chromatography), or differential solubility, among others. Alternatively or additionally, cell supernatant may be used directly, with no purification step. Additional entities, such as additional antigens or adjuvants may be added to purified VLPs.

In some embodiments, provided polynucleotide sequences are codon optimized. Codon optimization is well known in the art and involves modification of codon usage so that higher levels of protein are produced.

B. In Vivo VLP Production

Provided VLPs in accordance with the present invention may be prepared as DNA vaccines according to methods well known in the art. For example, in some embodiments, one or more vectors or plasmids, e.g., such as those described above, is administered to a subject such that recipient cells express polypeptides encoded by the vector or plasmid. In some embodiments, recipient cells expressing such polypeptides produce VLPs comprising the polypeptides.

C. Mono-, Di-, Trivalent eVLPs

In accordance with the present invention, cells may be transfected with a single expression vector as described herein. In some embodiments, a single expression vector encodes more than one element of a VLP (e.g., more than one of structural polyprotein, CMV tegument polypeptide, CMV glycoprotein, etc.). For example, in some embodiments, a single expression vector encodes two or more elements of a VLP. In some embodiments, a single expression vector encodes three of more elements of a VLP.

In some embodiments, cells are transfected with two or more expression vectors. For example, in some embodiments, cells are transfected with a first vector encoding a Gag polypeptide and a second vector encoding an HCMV envelope glycoprotein (e.g., gB or gB-G or gH-G). In some such embodiments, "monovalent" VLPs comprising an HCMV envelope glycoprotein (e.g., gB or gB-G or gH-G) are produced. In some embodiments, cells are transfected with a first vector encoding a Gag polypeptide, a second vector encoding an HCMV envelope glycoprotein (e.g., gB or gB-G or gH-G) and a third vector encoding another HCMV envelope glycoprotein (e.g., gB or gB-G or gH-G). In some such embodiments, "bivalent" VLPs comprising 2 HCMV envelope glycoproteins (e.g., gB and gH-G or gB-G and gH-G) are produced. In some embodiments, cells are transfected with a first vector encoding a Gag-pp65 fusion polypeptide and a second vector encoding an HCMV envelope glycoprotein (e.g., gB or gB-G or gH-G). In some such embodiments, "bivalent" VLPs comprising an HCMV structural protein and an HCMV envelope glycoprotein (e.g., gB or gB-G or gH-G) are produced. In some embodiments, cells are transfected with a first vector encoding a Gag-pp65 fusion polypeptide, a second vector encoding an HCMV envelope glycoprotein (e.g., gB or gB-G or gH-G), and a third vector encoding another HCMV envelope glycoprotein (e.g., gB or gB-G or gH-G). In some such embodiments, "trivalent" VLPs comprising an HCMV structural protein and 2 HCMV envelope glycoproteins (e.g., gB and gH-G or gB-G and gH-G) are produced.

In some embodiments, monovalent, bivalent, or trivalent VLPs are admixed. For example, in some embodiments, monovalent and bivalent VLPs are admixed to form a trivalent VLP mixture. In some embodiments two bivalent VLPs are admixed to form a trivalent VLP mixture.

III. HCMV Infection and Treatment

Human cytomegalovirus (HCMV), a β-herpesvirus, is a ubiquitously occurring pathogen. In general, entry of herpesviruses into cells is a complex process initiated by adsorption and receptor binding and followed by fusion of the virus envelope with a cell membrane. Fusion generally occurs at either the plasma membrane or an endosomal membrane. HCMV infects multiple cell types in vivo, including epithelial cells, endothelial cells and fibroblasts (Plachter B et al., 1996 Adv Virus Res 46:195-261). It fuses with the plasma membranes of fibroblasts (Compton T et al., 1992 Virology 191:387-395), but enters retinal pigmented epithelial cells and umbilical vein endothelial cells via endocytosis (Bodaghi B et al., 1999 J Immunol 162:957-964; Ryckman B J et al., 2006 J Virol 80:710-722). The mechanism by which herpesviruses' choose their route of entry remains unclear. It is generally assumed that entry pathways are mainly determined by the host cell, but there is evidence for tropic roles of virion glycoproteins (Wang X et al., 1998 J Virol 72:5552-5558). As mentioned previously, HCMV encodes two gH/gL complexes: gH/gL/gO and gH/gL/UL128/UL130/UL131. The gO-containing complex is sufficient for fibroblast infection, whereas the pUL128/UL130/UL131-containing complex is important for HCMV infection of endothelial and epithelial cells.

HCMV infects 50-85% of adults by 40 years of age (Gershon A A et al., 1997 in *Viral Infections of Humans, 4th* edition, New York; Plenum Press:229-251). Most healthy individuals who acquire HCMV after birth develop few, if any, symptoms. However, HCMV disease is the cause of significant morbidity and mortality in immunocompromised individuals, such as recipients of hematopoietic cell transplants (HCT) and solid-organ transplants (SOT) (Pass R F 2001 Cytomegalovirus. In Fields Virology. 4th edition, Philadelphia; Lippincott Williams & Wilkens:2675-2705). In SOT or HCT populations, HCMV disease can occur either from new infection transmitted from the donor organ or HCT, or can recur as a result of reactivation of latent virus in the recipient. In HIV-infected individuals, HCMV infection accelerates progression to AIDS and death, despite availability of antiretroviral therapy (Deayton J R et al., 2004 Lancet 363:2116-2121). In addition in the US, HCMV is the most common intrauterine infection and causes congenital abnormalities resulting in death or severe birth defects, including deafness and mental retardation, in approximately 8000 infants each year (Stagon S et al., 1986 JAMA 256:1904-1908).

Immune responses which control HCMV are incompletely understood. By analogy to other human herpesviruses it can be assumed that both cellular and humoral immune responses play an important role (Kohl S 1992 Current topics in Microbiology and Immunology 179:75-88). For murine CMV it was shown that either a cytotoxic T cell response or the passive transfer of neutralizing antibodies is sufficient to protect against a lethal challenge (Rapp M et al., 1993 Multidisciplinary Approach to Understanding Cytomegalovirus Disease:327-332; Reddehase M J et al., 198 J Virology 61:3102-3108).

Control of CMV in immunocompromised persons is primarily associated with cellular immune responses; both $CD8^+$ and $CD4^+$ T lymphocytes appear to be important for protection against CMV disease (Gamadia L E et al., 2003 Blood 101:2686-2692; Cobbold M et al., 2005 J Exp Med 202:379-386). The cellular immune response to CMV includes $CD4^+$ helper T-lymphocyte and $CD8^+$ Cytotoxic T-lymphocyte responses to a number of antigens, found in the viral tegument, the region of the viral particle between the envelope and capsid. A recent study of CMV-specific $CD4^+$ and $CD8^+$ T cells from healthy donors used overlapping peptides from a series of CMV open reading frames to identify antigens recognized after CMV infection (Sylwester A W et al., 2005 J Exp Med 202:673-685). The CMV tegument phosphoprotein 65 (pp65) and surface glycoprotein gB were the antigens most frequently recognized by $CD4^+$ T cells, and pp65 was also one of the antigens most frequently recognized by $CD8^+$ T cells.

In contrast to the transplant setting, the maternal humoral immune response against the virus seems to be important in preventing HCMV disease in the newborn. Antibodies to surface glycoproteins, especially gB, appear to be critical for protection against the maternal-fetal transfer of CMV (Fowler K B et al., 2003 JAMA 289:1008-1011). Moreover, in an earlier vaccination study it was shown that protection from re-infection is correlated with neutralizing antibodies (Adler S P et al., 1995 J Infectious Diseases 171:26-32). The humoral immune response to CMV is dominated by responses to viral envelope glycoproteins present in the outer envelope of the virus particle (e.g., gB and gH).

In the case of HCMV, direct evaluation of immunological effector functions is difficult since the virus is strictly species specific and no animal model system is available. However, murine CMV and guinea pig CMV have been used to evaluate vaccine strategies in these host species.

A CMV vaccine that induces both protective T cell and neutralizing antibody responses has the potential to prevent infection or ameliorate CMV disease due to congenital infection or transplantation.

The first live, attenuated HCMV vaccine candidate tested in humans was based on the laboratory-adapted AD169 strain. Subsequent trials with another laboratory-adapted clinical isolate, the Towne strain, confirmed that live attenuated vaccines could elicit neutralizing antibodies, as well as CD4+ and CD8+ T lymphocyte responses. The efficacy of the Towne vaccine was assessed in a series of studies in renal transplant recipients. Although the Towne vaccine did provide a protective impact on HCMV disease it failed to prevent HCMV infection after transplantation (Plotkin S A et al., 1984 Lancet 1:528-530). Towne vaccine was also evaluated in a placebo-controlled study of seronegative mothers who had children attending group daycare where it failed to prevent these women from acquiring infection from their HCMV-infected children (Adler S P et al., 1995 J Infectious Diseases 171:26-32). An interpretation of these studies was that the Towne vaccine was overattenuated. To explore this possibility a series of genetic recombinants in which regions of the unattenuated "Toledo" strain of CMV were substituted for the corresponding regions of the Towne genome, resulting in the construction of Towne/Toledo "chimeras" that contain some, but not all, of the mutations that contribute to the Towne vaccine attenuation (Heineman T C et al. 2006 J Infect Disease 193:1350-1360). The safety and tolerability of four Towne/Toledo "chimeras" is being tested in a Phase I trial. Long-term safety concerns about the potential risk of establishing a latent HCMV infection have hindered the further development of live, attenuated vaccines.

The leading subunit CMV vaccine candidate is based on the envelope glycoprotein, gB, (purified recombinant gB vaccine is manufactured by Sanofi-Pasteur Vaccines) due to this protein's ability to elicit high-titer, virus-neutralizing antibody responses during natural infection. The recombinant gB vaccine elicits neutralizing antibody responses and has an excellent safety profile, however, it excludes other glycoprotein targets of neutralizing antibody response and more importantly T-lymphocyte targets. The vaccine requires MF59 adjuvant to optimize immunogenicity. In the most recent trial, this vaccine provided an overall 50% efficacy for prevention of CMV infection in a Phase 2 clinical trial in young woman (Pass R F et al., 2009 N Engl J Med 360:1191-1199). Other viral proteins being evaluated as subunit vaccine candidates include pp65 and IE1, both of which elicit T-cell responses.

DNA vaccines elicit robust cellular and humoral immune responses in animals and are well suited to specificity and precision in vaccine design. DNA vaccines have been developed for CMV and have focused on gB, IE1 and pp65 proteins as the candidate target immunogens. A bivalent CMV DNA vaccine candidate (Wloch M K 2008 J Infectious Diseases 297:1634-1642), using plasmid DNA encoding pp65 and gB and a trivalent vaccine candidate (Jacobson M A 2009 Vaccine 27:1540-1548) that also includes a third plasmid encoding the IE1 gene product have been developed by Vical Vaccines (U.S. Pat. No. 7,410,795). The trivalent DNA vaccine alone had minimal immunogenicity irrespective of route of administration. However the CMV DNA vaccine did appear to safely prime for a memory response to CMV antigens observed after administration of a live, attenuated CMV (Towne).

In a vectored vaccine approach, the gene product of interest is expressed in the context of a non-replicating (usually viral) carrier. One example of this is a canarypox vector called ALVAC developed by Virogenetics and Sanofi-Pasteur Vaccines, which is an attenuated poxvirus that replicates abortively in mammalian cells. ALVAC expressing CMV gB and ALVAC expressing pp65 (U.S. Pat. No. 6,267,965) have been tested in clinical trials. ALVAC-CMV (gB) did not induce neutralizing antibodies but did prime for higher neutralizing antibody titers after subsequent infection with the Towne strain CMV (Adler S P et al. 1999 J Infectious Diseases 180:843-846), although it did not appear to boost neutralizing antibody titers after subsequent immunization with gB subunit/1V1F59 vaccine (Bernstein D I et al. 2002 J Infectious Diseases 185:686-690). A canarypox vector expressing pp65, ALVAC-CMV(pp64), induced long-lasting CTL responses in all originally seronegative volunteers, at frequencies comparable to naturally seropositive individuals (Berencsi K et al. 2001 J Infectious Diseases 183:1171-1179). Another approach used to express gB as a vectored vaccine is the use of an alphavirus replicon system by AlphaVax Inc (U.S. Pat. No. 7,419,674). This approach involves a propagation-defective single-cycle RNA replicon vector system derived from an attenuated strain of an alphavirus, Venezuelan Equine Encephalitis (VEE) virus, to produce virus-like replicon particles (VRPs) expressing pp65, IE1 or gB protein (Berstein et al., 2010 Vaccine 28:484-493). A two component alphavirus replicon vaccine was used to express the three CMV proteins as a soluble form of CMV gB (Towne strain) and a pp65/IE1 fusion protein (Reap E A et al. 2007 Vaccine 25:7441-7449) was found to be safe and induced high levels of neutralizing antibody and polyfunctional CD4+ and CD8+ antigen-specific T cell responses. The Geometric Mean Titre (GMT) for the high dose group was about half the GMT in 12 naturally infected, CMV seropositive individuals tested in the assay.

A novel candidate for vaccination against HCMV currently in preclinical development is the "dense body" vaccine. Dense bodies (DBs) are enveloped, replication-defective particles formed during the replication of CMVs in cell culture. They contain both envelope glycoproteins and large quantities of pp65 protein. DBs are non-infectious and immunogenic but incapable of establishing latent HCMV infection in the vaccine recipient. DBs have been shown to be capable of inducing virus neutralizing antibodies and T-cell responses in mice in the absence of viral gene expression (Pepped S et al., 2000 J Virol 74:6132-6146—WO 00/53729 and U.S. Pat. No. 6,713,070).

IV. Pharmaceutical Compositions

The present invention provides pharmaceutical compositions comprising provided VLPs and/or provided glycoprotein variants. In some embodiments, the present invention provides a VLP and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of HCMV or of negative ramifications associated or correlated with HCMV infection. In some embodiments, provided pharmaceutical compositions are useful in therapeutic applications, for example in individuals suffering from or susceptible to HCMV infection. In some embodiments, pharmaceutical compositions are formulated for administration to humans.

For example, pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. In addition, if desired, the vaccine may contain auxiliary substances such as wetting or emulsifying agents, pH buffering agents, or adjuvants which enhance the effectiveness of the vaccines. In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of VLP formulations for longer than the specified time results in VLP degradation.

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, MD, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutical composition is sufficiently immunogenic as a vaccine (e.g., in the absence of an adjuvant). In some embodiments, immunogenicity of a pharmaceutical composition is enhanced by including an adjuvant. Any adjuvant may be used in accordance with the present invention. A large number of adjuvants are known; a useful compendium of many such compounds is prepared by the National Institutes of Health and can be found (www.niaid.nih.gov/daids/vaccine/pdf/compendium.pdf). See also Allison (1998, Dev. Biol. Stand., 92:3-11; incorporated herein by reference), Unkeless et al. (1998, Annu. Rev. Immunol., 6:251-281; incorporated herein by reference), and Phillips et al. (1992, Vaccine, 10:151-158; incorporated herein by reference). Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500, 161, which is incorporated herein by reference), Q57, QS21, squalene, tetrachlorodecaoxide, etc. Pharmaceutically acceptable excipients have been previously described in further detail in the above section entitled "Pharmaceutical Compositions."

V. Administration

Provided compositions and methods of the present disclosure are useful for prophylaxis and/or treatment of HCMV infection in a subject, including human adults and children. In general however they may be used with any animal. In certain embodiments, the methods herein may be used for veterinary applications, e.g., canine and feline applications. If desired, the methods herein may also be used with farm animals, such as ovine, avian, bovine, porcine and equine breeds.

As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLP) to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In certain embodiments a particular amount of a VLP composition is administered as a single dose. In certain embodiments, a particular amount of a VLP composition is administered as more than one dose (e.g., 1-3 doses that are separated by 1-12 months). In certain embodiments a particular amount of a VLP composition is administered as a single dose on several occasions (e.g., 1-3 doses that are separated by 1-12 months).

In some embodiments, a provided composition is administered in an initial dose and in at least one booster dose. In some embodiments, a provided composition is administered in an initial dose and two booster doses. In some embodiments, a provided composition is administered in an initial dose and three booster doses. In some embodiments, a provided composition is administered in an initial dose and four booster doses. In some embodiments, a provided composition is administered in an initial dose and in at least one booster dose about one month, about two months, about three months, about four months, about five months, or about six months following the initial dose. In some embodiments, a provided composition is administered in a second booster dose about six months, about seven months, about eight months, about nine months, about ten months, about eleven months, or about one year following the initial dose. In some embodiments, a provided composition is administered in a booster dose every 1 year, 2 years, 3 years, 4 years, 5 years, 6 years, 7 years, 8 years, 9 years, or 10 years.

In certain embodiments, provided compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for peroral delivery, oral delivery, intranasal delivery, buccal delivery, sublingual delivery, transdermal delivery, transcutaneous delivery, intraperitoneal delivery, intravaginal delivery, rectal delivery or intracranial delivery.

EXAMPLES

The following examples describe some exemplary modes of making and practicing certain compositions that are described herein. It should be understood that these examples are for illustrative purposes only and are not meant to limit the scope of the compositions and methods described herein.

Example 1: Construction of DNA Expression Plasmids

This Example describes development of expression plasmids and constructs for expression of recombinant HCMV gene sequences (e.g., gB, gB-G, gH-G, and Gag/pp65 fusion gene sequences). A standard expression plasmid generally consists of a promoter sequence of mammalian origin, an intron sequence, a PolyAdenylation signal sequence (PolyA), a pUC origin of replication sequence (pUC—pBR322 is a colE1 origin/site of replication initiation and is used to replicate plasmid in bacteria such as *E Coli* (DH5α)), and an antibiotic resistance gene as a selectable marker for plasmid plaque selection. Within the plasmid following the Intron are a variety of restriction enzyme sites that can be used to splice in a gene or partial gene sequence of interest.

Figure 1A:
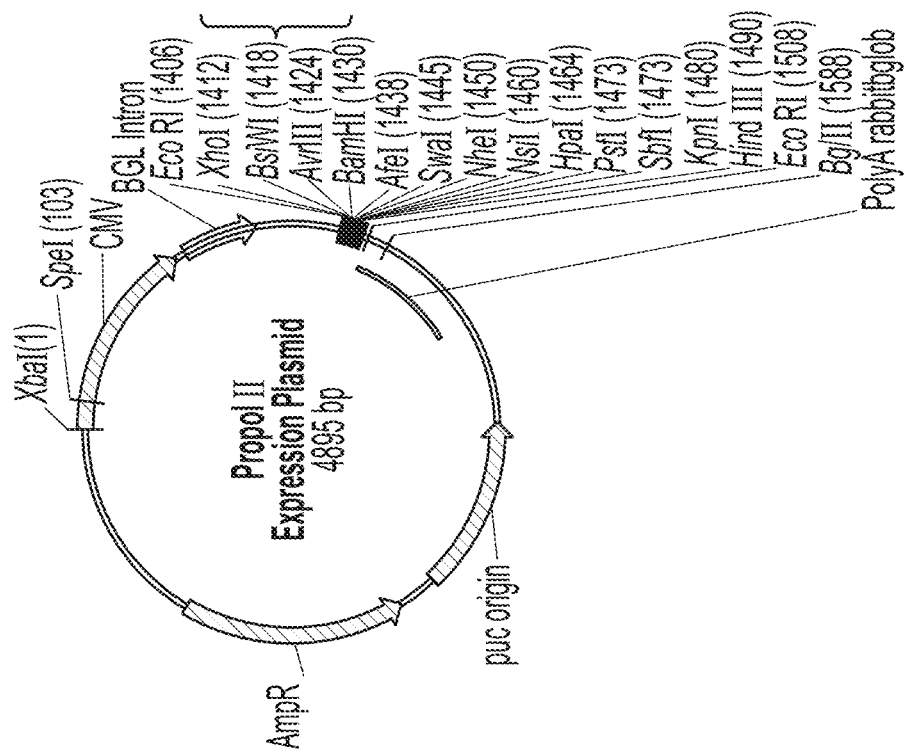
FIG. 1A shows the DNA expression plasmid map of exemplary recombinant expression plasmids.

The Propol II expression plasmid contains the pHCMV (early promoter for HCMV), a Beta-Globin Intron (BGL Intron), a rabbit Globin polyAdenylation signal sequence (PolyA), a pUC origin of replication sequence (pUC—pBR322 is a colE1 origin/site of replication initiation and is used to replicate plasmid in bacteria such as *E. coli* (DH5α)), and an ampicillin resistance gene β-lactamase (Amp R—selectable marker for plasmid confers resistance to ampicillin) (100 μg/ml) (FIG. 1A).

FIG. 1B depicts exemplary recombinant expression plasmids. For example, to develop a pHCMV-Gag MMLV expression construct ("MLV-Gag"), a complementary DNA (cDNA) sequence encoding a Gag polyprotein of MMLV (Gag without its C terminus Pol sequence) was cloned in a Propol II (pHCMV) expression vector. To develop a gB expression construct ("gB"), the full-length sequence of gB was codon-optimized for human expression (GenScript) and was cloned in a Propol II expression vector including the extracellular portion, transmembrane domain (TM) and cytoplasmic portion (Cyto) of gB. To develop a gH-G expression construct ("gH-G"), the truncated sequence of gH encoding only the extracellular portion was fused together with TM and Cyto portions of VSV-G and codon-optimized for human expression (GenScript) and cloned in a Propol II expression vector. Similarly, to develop a gB-G expression construct ("gB-G"), the truncated sequence of gB encoding only the extracellular portion was fused together with TM and Cyto portions of VSV-G and codon-optimized for human expression (GenScript) and cloned in a Propol II expression vector. To develop a Gag/pp65 expression construct ("Gag/pp65"), a sequence encoding the Gag polyprotein of MMLV (Gag without its C terminus Pol sequence) was fused with the full-length sequence of pp65 and codon-optimized for human expression (GenScript) and cloned in a Propol II expression vector.

DNA plasmids were amplified in competent *E. coli* (DH5α) and purified with endotoxin-free preparation kits according to standard protocols.

Example 2: Production of Virus-Like Particles (VLPs)

This Example describes methods for production of virus-like particles (VLPs) containing various recombinant HCMV antigens described in Example 1.

Figure 2A:
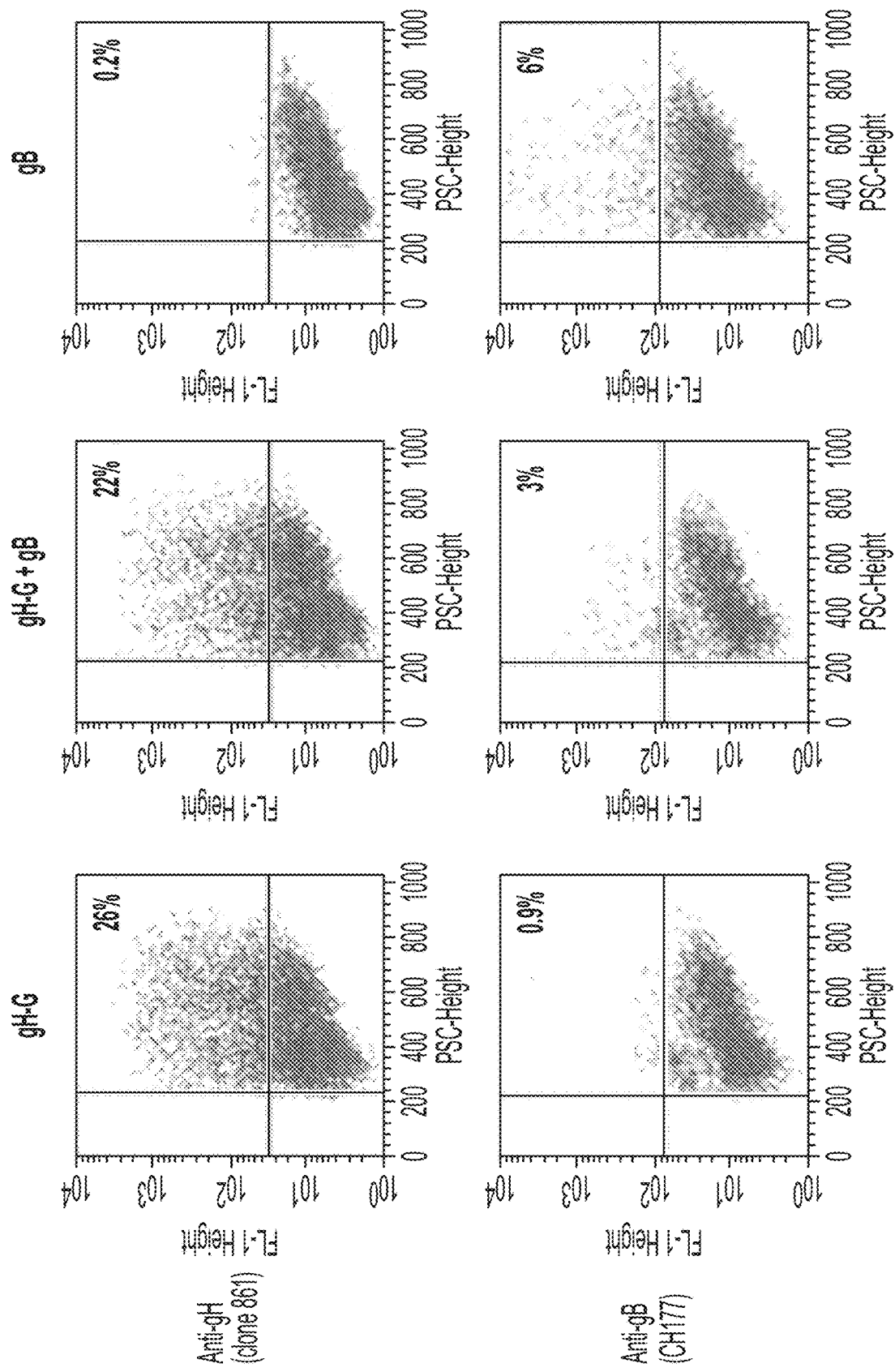
FIG. 2A shows FACS analysis of exemplary heterologous surface antigens on HEK 293 packaging cells.
Figure 2B:
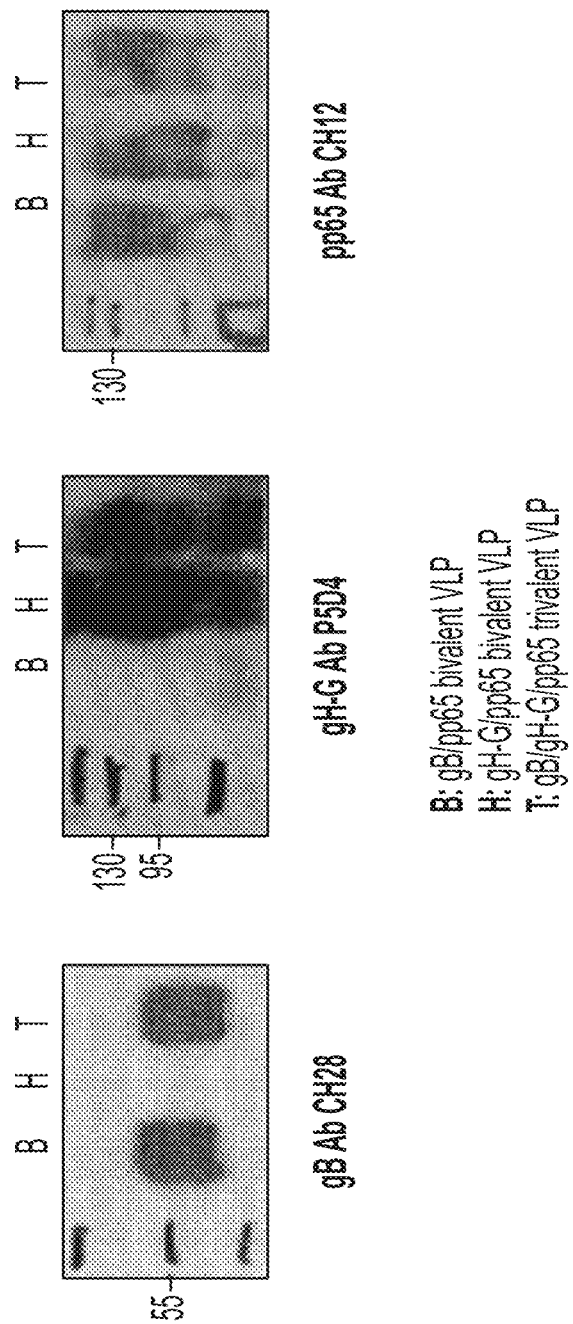
FIG. 2B shows western blot analysis of heterologous antigen expression in exemplary VLP compositions.

HEK 293T cells (ATCC, CRL-11268) were transiently transfected using calcium phosphate methods with an MMLV-Gag DNA expression plasmid and co-transfected with either a gB or a gB-G (data not shown) or a gH-G DNA expression plasmid. Alternatively cells were transfected with a Gag/pp65 DNA expression plasmid and co-transfected with either a gB or a gB-G (data not shown) or a gH-G DNA expression plasmid. It will be appreciated that cells can be transfected with an MMLV-Gag DNA expression plasmid and cotransfected with both a gB and a gH-G or gB-G and a gH-G DNA expression plasmid. Expression of various HCMV antigens by the HEK 293 cells was confirmed by flow cytometry (FIG. 2A). After 48 to 72 hours of transfection, supernatants containing the VLPs were harvested and filtered through 0.45 µm pore size membranes and further concentrated and purified by ultracentrifugation through a 20% sucrose cushion in a SW32 Beckman rotor (25,000 rpm, 2 hours, 4° C.). Pellets were resuspended in sterile endotoxin-free PBS (GIBCO) to obtain 500 times concentrated VLP stocks. Total protein was determined on an aliquot by a Bradford assay quantification kit (BioRad). Purified VLPs were stored at −80° C. until used. Each lot of purified VLPs was analyzed for the expression of MMLV-Gag, gB, gH-G and/or MMLV-Gag/pp65 fusion protein by SDS-Page and Western Blot with specific antibodies to gB (CH 28 mouse monoclonal antibody to gB; Virusys Corporation; Pereira, L et al. 1984 Virology 139:73-86), gH-G (mouse monoclonal antibody to Anti-VSV-G tag antibody P5D4; Abcam plc) and pp65 (CH12 mouse monoclonal antibody to UL83/pp65; Virusys Corporation; Pereira, L. et al. 1982 Infect Immun 36: 924-932) (FIG. 2B). Antibodies were detected using enhanced chemilluminescence (ECL).

Example 3: Physico-Chemical Characterization of Virus-Like Particles (VLPs)

Figure 3A:
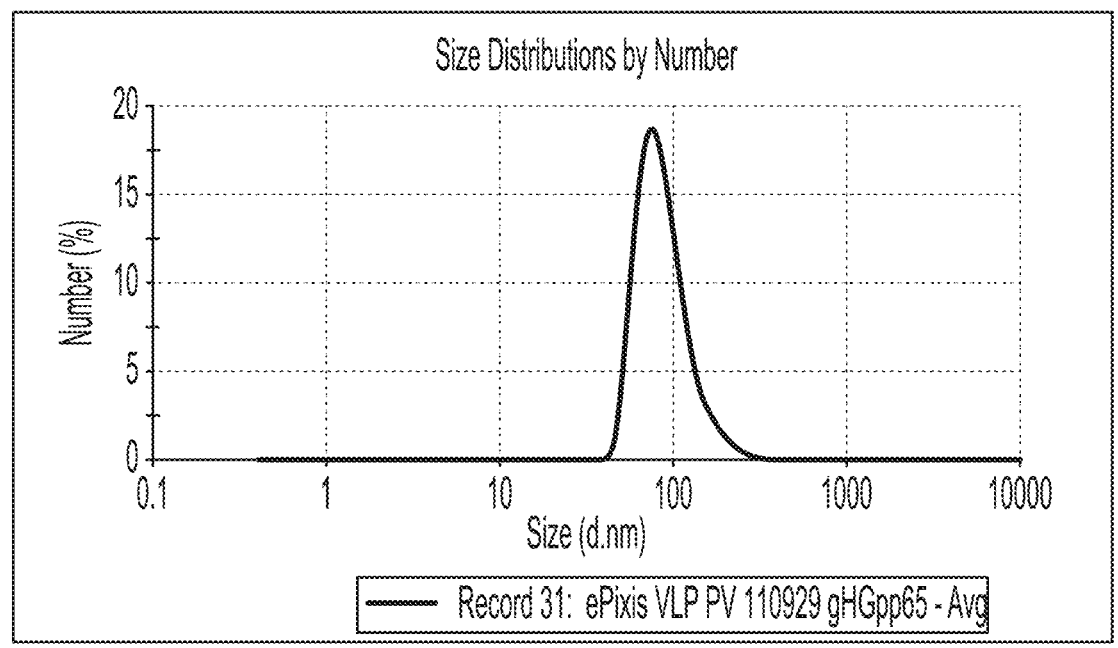
FIG. 3A shows particle size determination and polydispersity index for an exemplary VLP composition.
Figure 3B:
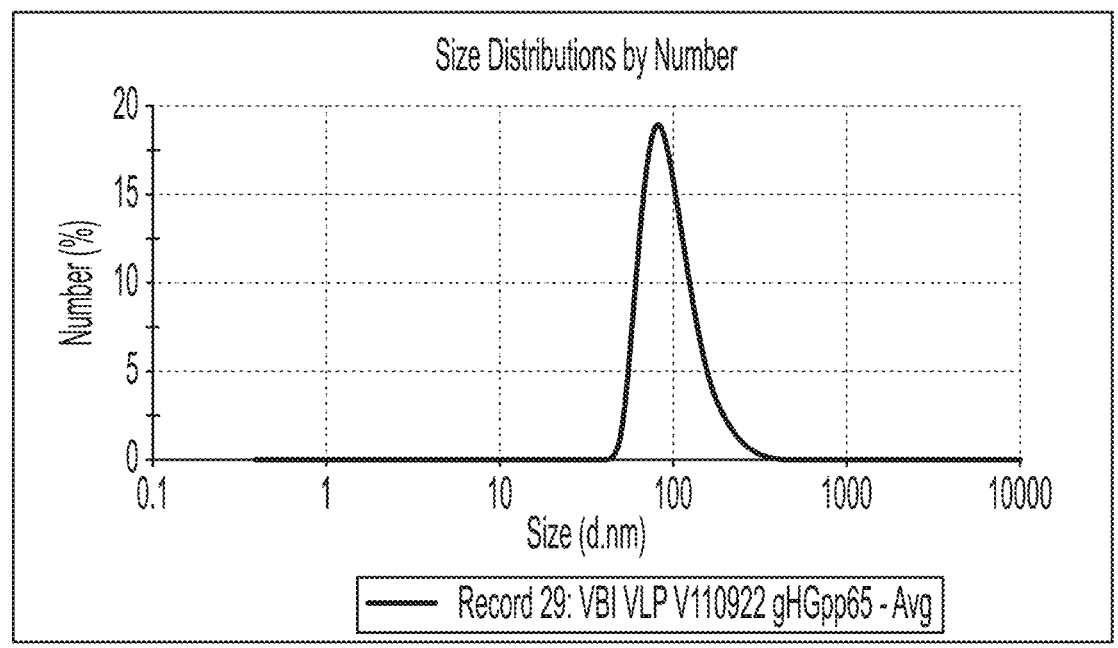
FIG. 3B shows particle size determination and polydispersity index for an exemplary VLP composition.

Physico-chemical analysis of VLPs included particle size determination and Polydispersity Index assessment using a Malvern Instrument Zeta-Sizer Nano series (ZEN3600). Exemplary results obtained from nanosizing analysis are shown in FIGS. 3A and 3B. An exemplary VLP composition (gH-G/pp65 bivalent VLP composition) was produced in two different labs using the same recombinant expression vectors and both VLP preparations gave an average particle size of 150-180 nm in diameter. This is consistent with the size of a CMV virion which is reported to be 150-200 nm in size (1997 J Pathol 182: 273-281). The low Polydispersity Index (PdI) of 0.214-0.240 indicates product homogeneity or a narrow size distribution.

Example 4: Immunogenicity and Neutralization Activity of VLPs in Mice

VLP compositions prepared as described in Example 2 were tested in female BALB/C mice 6-8 weeks old (minimum 6 animals per test group). Mice were immunized intraperitoneally with 200 µl of VLP compositions twice, once on day 0 (Prime) and once on day 56 (week 8 Boost). Mice were treated with 10 µg, 25 µg or 50 µg (total protein) of a bivalent gB/Gag/pp65, a bivalent gH-G/Gag/pp65 or a trivalent gB/gH-G/Gag/pp65 VLP composition. To assess humoral immune responses in mice, blood was collected from all mice in the study groups pre-immunization and then post-$1^{st}$ and -$2^{nd}$ immunizations at 0, 2, 3, 4, 6, 8, 9, 10, 12 and 14 weeks. The study design is summarized in Table 1.

TABLE 1

| Test Article # | Dose | Test Article Description | Immunization Schedule (weeks) |
| --- | --- | --- | --- |
| 1 | 50 µg | pp65/gB bivalent VLPs | 0, 8 |
| 2 | 25 µg | pp65/gB bivalent VLPs | 0, 8 |
| 3 | 10 µg | pp65/gB bivalent VLPs | 0, 8 |
| 4 | 50 µg | pp65/gH-G bivalent VLPs | 0, 8 |
| 5 | 25 µg | pp65/gH-G bivalent VLPs | 0, 8 |
| 6 | 10 µg | pp65/gH-G bivalent VLPs | 0, 8 |
| 7 | 50 µg | Trivalent pp65/gB/gH-G VLPs | 0, 8 |

TABLE 1-continued

| Test Article # | Dose | Test Article Description | Immunization Schedule (weeks) |
| --- | --- | --- | --- |
| 8 | 25 µg | Trivalent pp65/gB/gH-G VLPs | 0, 8 |
| 9 | 10 µg | Trivalent pp65/gB/gH-G VLPs | 0, 8 |

Figure 4A:
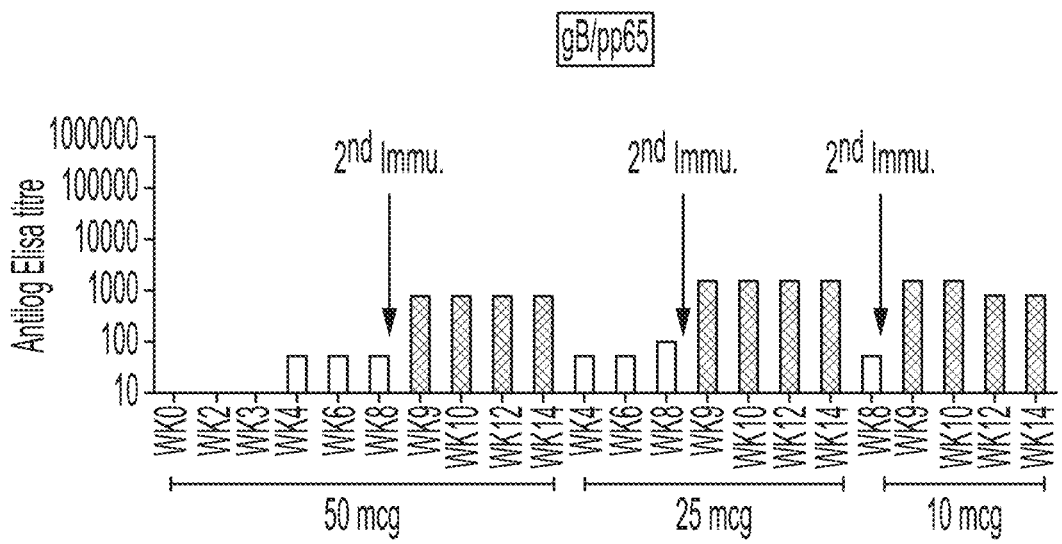
FIG. 4A shows ELISA titers in mice treated with exemplary gB/pp65 VLP composition.
Figure 4B:
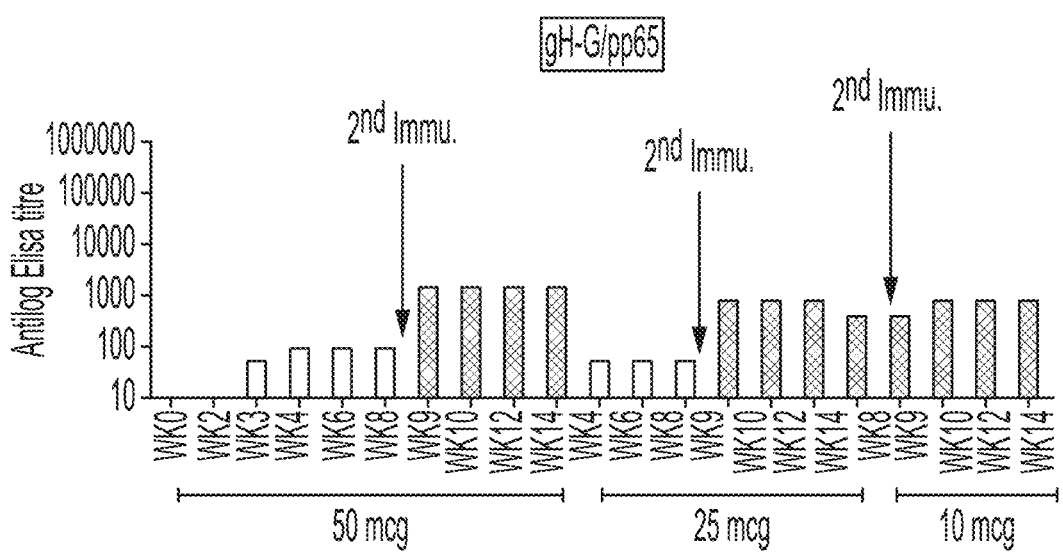
FIG. 4B shows ELISA titers in mice treated with exemplary gH-G/pp65 VLP composition.
Figure 4C:
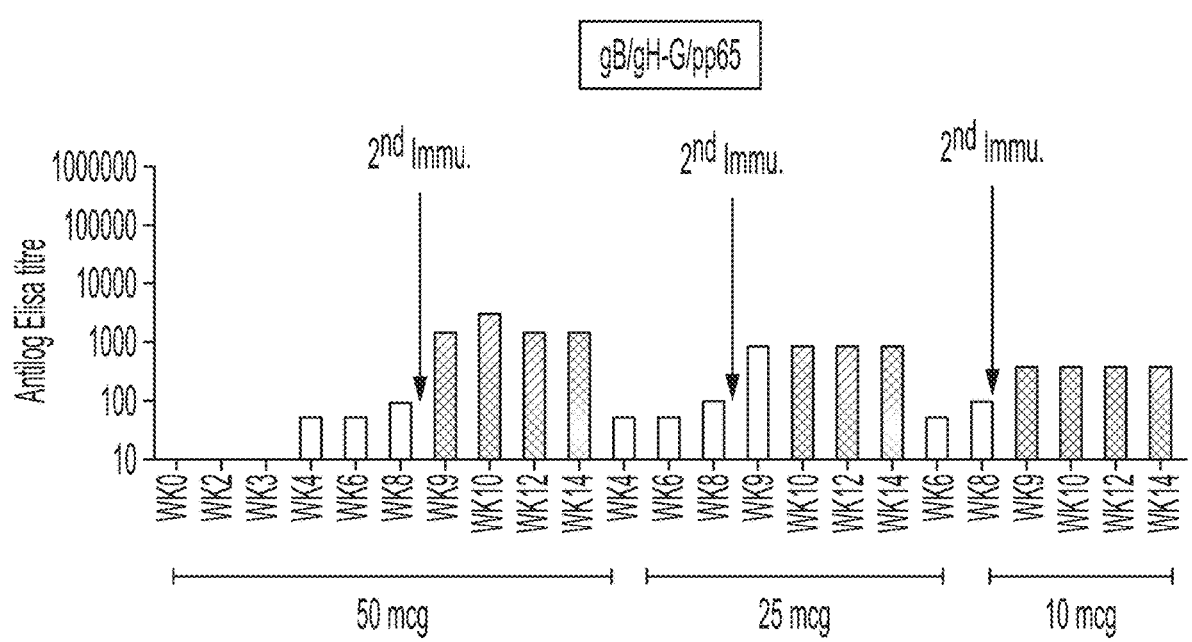
FIG. 4C shows ELISA titers in mice treated with exemplary gB/gH-G/pp65 VLP composition.

Enzyme-linked Immunosorbent Assay (ELISA) was performed using commercially available ELISA plates (IBL International) coated with lysates derived from MRC-5 cells infected with HCMV strain AD169. Crude commercial HCMV lysate, which contains all CMV related antigens and is useful to detect IgG immune responses, was used as a positive control to determine mouse serum HCMV IgG content by ELISA. Serial dilutions of mouse sera (dilution in TBS-T/BSA/DMEM 10% FCS) were incubated with the coated plates for 2 hours at room temperature. After the plates were washed, anti-mouse Horse Radish Peroxidase (HRP) conjugated secondary antibody was added at a dilution of 1/10,000 and incubated for 1 hour, followed by the addition of Tetramethylbenzidine (TMB) substrate solution. The reaction was stopped by addition of HCL 1N and absorbance was read at 450 nm in an ELISA microwell plate reader. FIG. 4 shows evidence of persistent antibodies and strong boosting of mice after 2nd immunization at 8 weeks for each of the bivalent and the trivalent VLP compositions.

Figure 5:
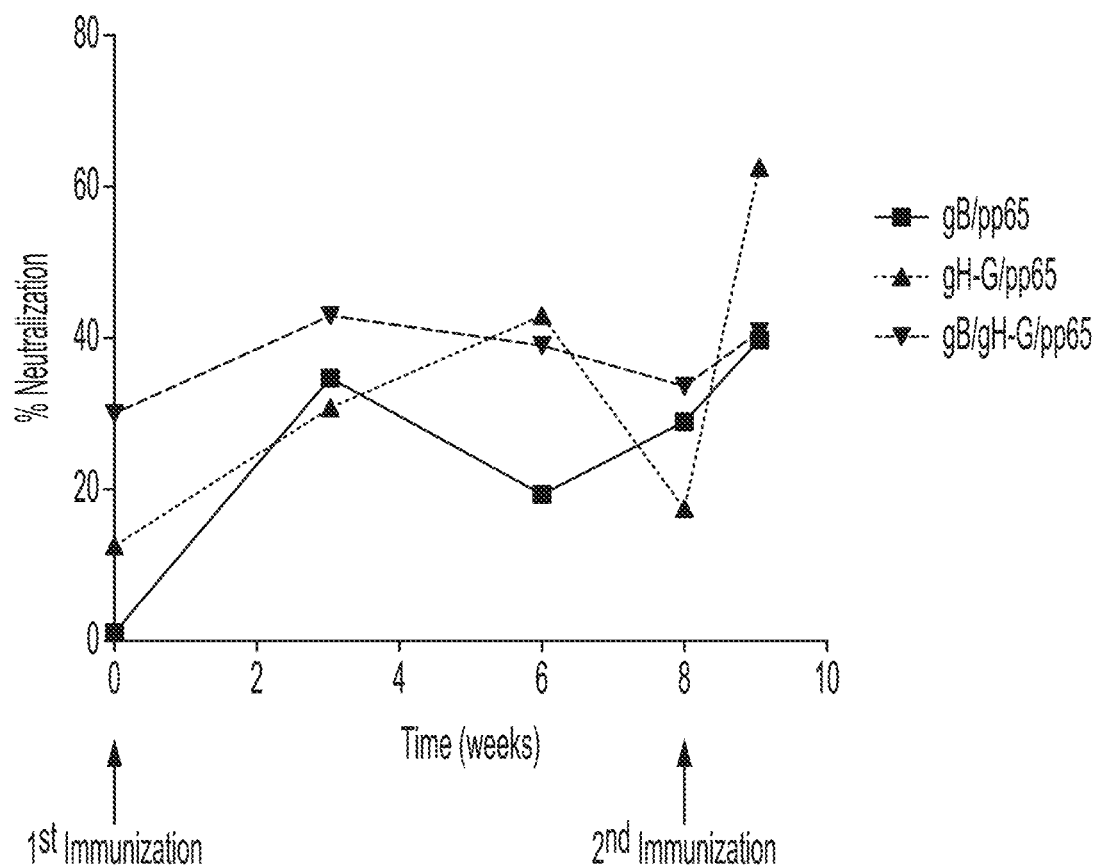
FIG. 5 shows neutralizing antibody activity in mice treated with exemplary VLP compositions (assayed in human fibroblast cells).
Figure 6:
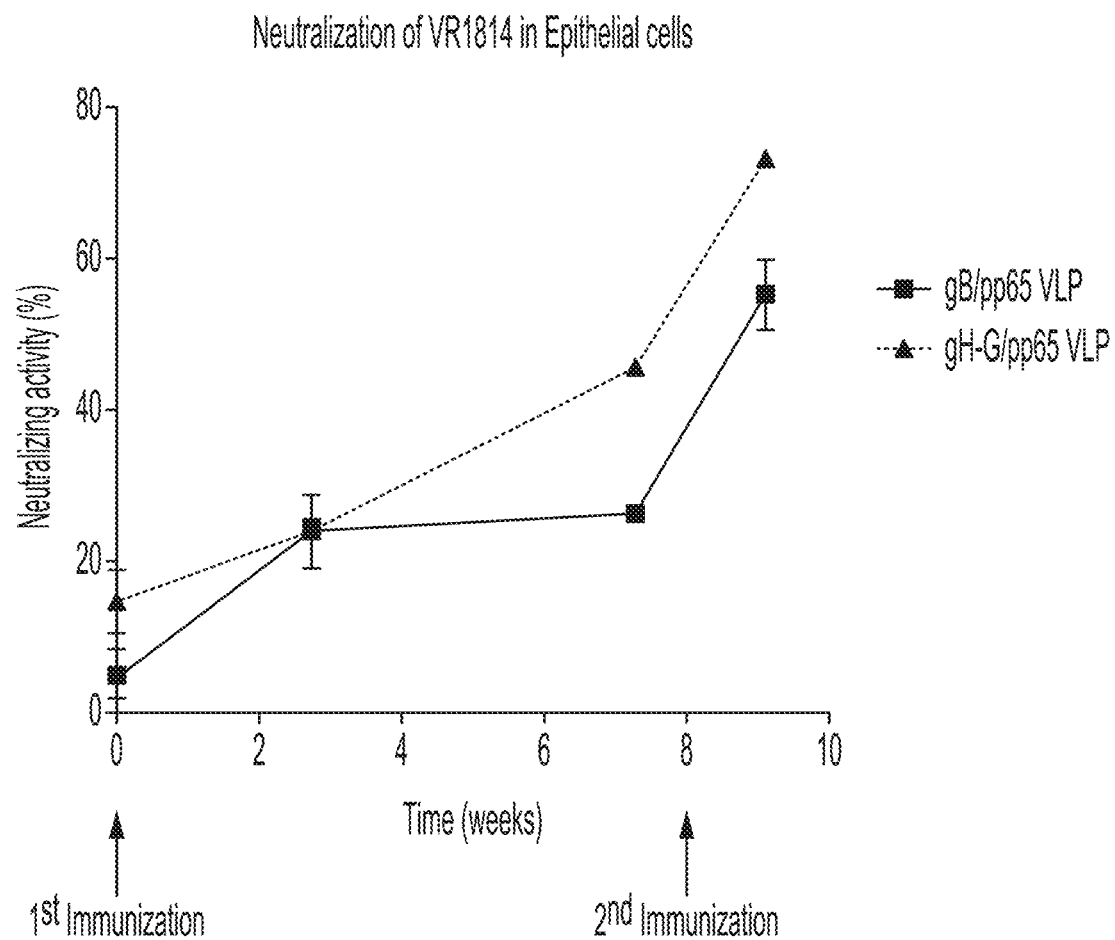
FIG. 6 shows neutralizing antibody activity in mice treated with exemplary VLP compositions (assayed in human epithelial cells).

Neutralizing antibody responses to HCMV were determined using a microneutralization assay. A standard amount of HCMV strain VR1814 (an endothelial cell-tropic CMV strain—Revello M G et al. J Gen Virol 82:1429-1438) was diluted with infection medium (DME containing 1% heat-inactivated FBS, 1% amino acid mixture, 1% Penicillin-Streptomycin and $Ca^{+2}$ and $Mg^{+2}$ free PBS), and added to an equal volume of serial dilutions of heat-inactivated test serum and incubated for 1 hour at 37° C. on a rotator. The serum/HCMV mixtures were added to human foreskin fibroblasts (HFF) or retinal pigmented epithelial cells (ARPE-19 cells) grown on coverslips in 24 well tissue culture plates and incubated for 2 hours at 37° C., 5% $CO_2$. The plates were washed with PBS twice and then cultured for 48 hours at 37° C., 5% $CO_2$. Cells were fixed with 4% paraformaldehyde, reacted with an anti-IE1 monoclonal antibody (CH160 Mouse Monoclonal antibody to IE1/2 or CH443 Monoclonal antibody to IE1; Virusys Corporation) for 1 hour at room temperature followed by FITC-labelled goat anti-mouse antibody for 45 minutes at room temperature. The number of cells expressing IE1 was determined by fluorescent microscopy. Pooled mouse sera (1:6 dilution) was tested for neutralizing activity at each bleed time point (0, 3, 6, 8 and 9 weeks) in duplicate. FIG. 5 shows induction of neutralizing antibodies in mice (assayed in fibroblast cells) after 2nd immunization at 8 weeks for each of the bivalent and the trivalent VLP compositions. FIG. 6 shows induction of neutralizing antibodies in mice (assayed in epithelial cells) after 2nd immunization at 8 weeks for each of the bivalent VLP compositions.

In another study, monovalent gB-G VLP compositions prepared as described in Example 2 were tested in female BALB/C mice 6-8 weeks old (minimum 8 animals per test group). Mice were immunized intraperitoneally with 200 µl of VLP compositions twice, once on day 0 (Prime) and once on day 56 (week 8 Boost). Mice were treated with equivalent amounts of 20 µg of gB content (determined by ELISA) per injection. To assess humoral immune responses in mice, blood was collected from all mice in the study groups pre-$1^{st}$ immunization and then post-$1^{st}$ immunization at 3 and 6 weeks and pre-$2^{nd}$ immunization at 8 weeks and then post $2^{nd}$ immunization at 9 weeks from study start. The study design is summarized in Table 2.

TABLE 2

| Test Article # | Dose | Test Article Description | Immunization Schedule (weeks) |
|---|---|---|---|
| 1 | 20 μg | gB-G monovalent VLPs | 0, 8 |
| 2 | 20 μg | Recombinant gB | 0, 8 |

Figure 7:
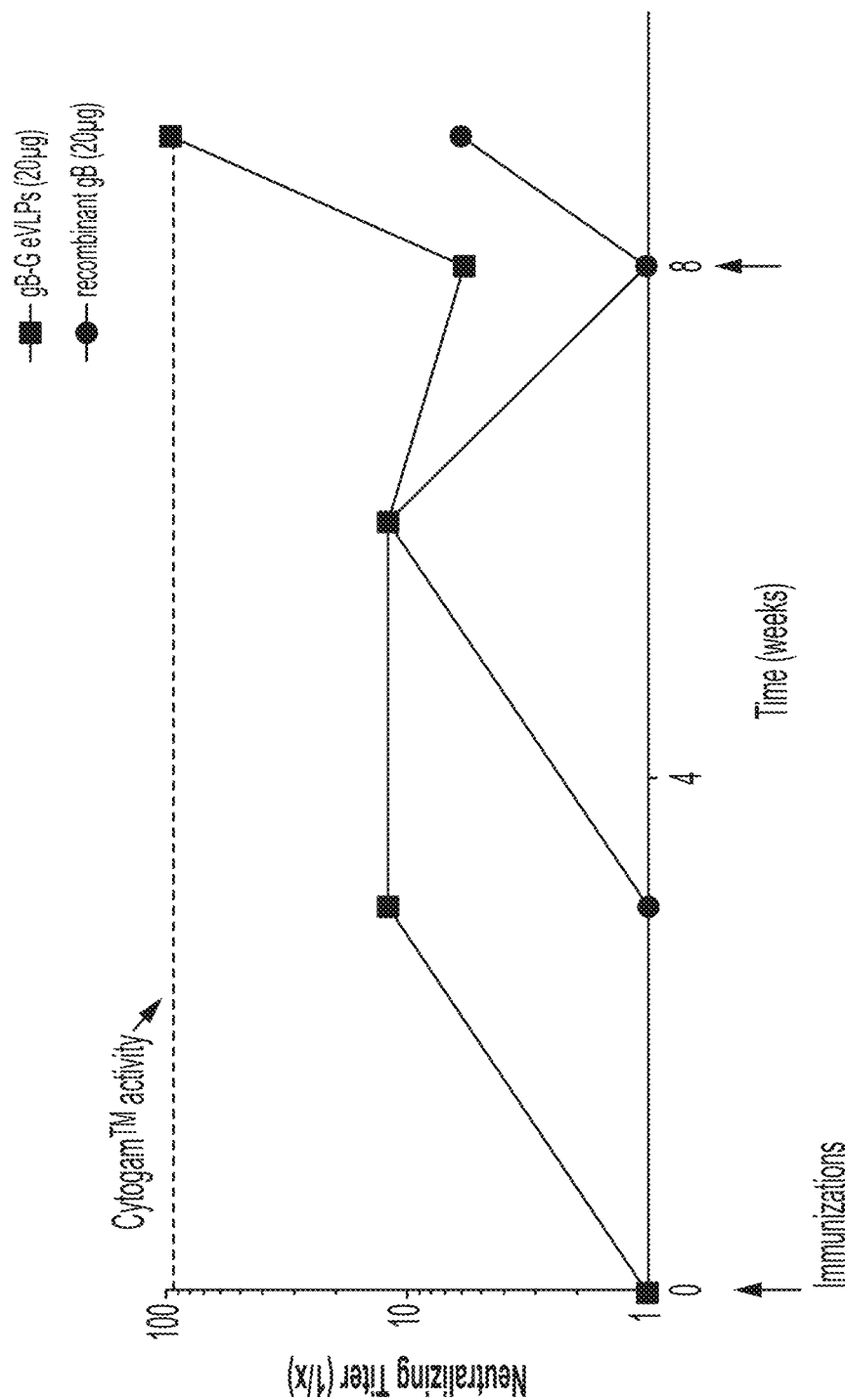
FIG. 7 shows neutralizing antibody activity in mice treated with exemplary VLP compositions versus a recombinant gB protein (assayed in human fibroblast cells).

Neutralizing antibody responses to HCMV were determined using a microneutralization assay in fibroblast cells based on a green fluorescent protein (GFP)-expressing HCMV virus (TB40) and flow cytometric analysis of infected (GFP+) HFF cells. To assess the presence of neutralizing antibodies in serum samples, the serum was pre-incubated with GFP-expressing HCMV for a period of time sufficient for neutralizing antibodies to reduce the infectivity of HCMV. Serial dilutions of the pre-incubated mixture of serum and HCMV were used to contact a host cell (fibroblast or epithelial) susceptible to infection by HCMV. The number of cells that express the reporter gene construct (GFP) were determined by flow cytometry to calculate the infectious titer of the virus preparation. FIG. 7 depicts Neutralizing Antibody titers for mice immunized twice at 0 and 8 weeks with monovalent gB-G VLPs versus recombinant gB. Sera collected pre- and post-immunizations as described were pooled and tested relative to a positive control CMV hyperglobulin, Cytogam™, in the presence of 10% guinea pig complement. As shown in FIG. 7, the monovalent gB-G VLP composition elicited a more rapid and potent neutralization of fibroblast cell infection than that elicited by a recombinant gB protein.

As can be seen (or as will be appreciated by those skilled in the art having read the present specification), the data demonstrate, among other things, surprisingly good activity of VLPs, such as by VLPs that include gB-G as compared with recombinant gB.

Figures 8A, 8B:
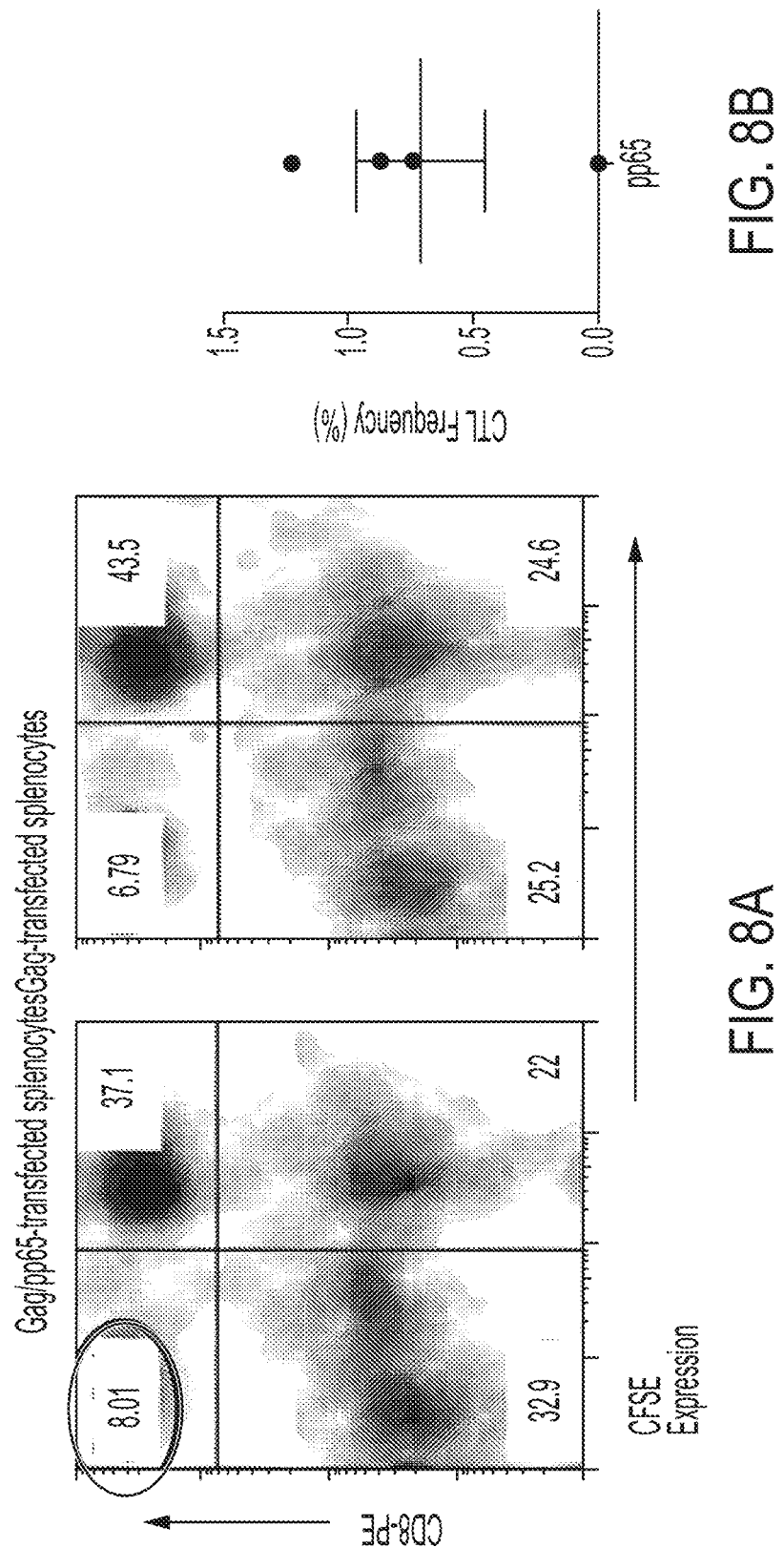
FIG. 8A shows antigen-specific CTL responses in mice treated with exemplary VLP compositions expressed in HEK 293 cells, depicted as CTL frequency based on CFSE decay, gating on CD3$^+$ CD8$^+$ T cells.
FIG. 8B shows antigen-specific CTL responses in mice treated with exemplary VLP compositions expressed in HEK 293 cells, depicted as frequency of proliferating pp65-specific CTLs.

In another study, bivalent gB/Gag/pp65 VLP compositions prepared as described in Example 2 were tested in female BALB/C mice 6-8 weeks old (minimum 4 animals per test group). Mice were immunized intraperitoneally with 200 μl of VLP compositions twice, once on day 0 (Prime) and once on day 56 (week 8 Boost). Mice were treated with bivalent gB/Gag/pp65 VLPs and splenocytes were collected 14 days later. Enriched CD8+ T cells were stimulated (1:5 ratio) with splenocytes transfected for 24 hours with plasmid encoding Gag/pp65 or Gag to determine frequencies of CTLs directed against pp65 or Gag. CTL frequencies were determined based on CFSE decay, gating on CD3+ CD8+ T cells (FIG. 8A). The scatter plot shows the frequency of proliferating, pp65-specific CTLs after subtracting responses directed against Gag (FIG. 8B). As depicted in FIG. 8, bivalent gB/Gag/pp65 VLPs elicited pp65-specific CTLs in immunized mice.

Example 5: Immunogenicity and Neutralization Activity of VLPs in Rabbits

Bivalent gB/Gag/pp65 and gH-G/Gag/pp65 VLP compositions prepared as described in Example 2 were tested in New Zealand White rabbits 6-8 weeks old (minimum 6 animals per test group). Rabbits were immunized intramuscularly with 0.5 ml of VLP compositions three times, once on day 0 (Prime) and once on day 56 (week 8 Boost) and once on day 168 (week 24 Boost). Rabbits were treated with 25 μg or 50 μg or 100 μg (total protein) of either a bivalent gB/Gag/pp65, a bivalent gH-G/Gag/pp65 or a trivalent gB/gH-G/Gag/pp65 (bivalent gB/Gag/pp65 and gH-G/Gag/pp65 mixed together at a 1:1 ratio) VLP composition. To assess humoral immune responses in rabbits, blood was collected from all rabbits in the study groups pre-$1^{st}$ immunization and then post-$1^{st}$ immunization at 2, 4, 6 and 8 weeks and post-$2^{nd}$ immunization at 10, 13, 16, 20 and 24 weeks from study start and then post-$3^{rd}$ immunization at 26 and 28 weeks from study start. The study design is summarized in Table 3.

TABLE 3

| Test Article # | Dose | Test Article Description | Immunization Schedule (weeks) |
|---|---|---|---|
| 1 | 100 μg | gB/pp65 bivalent VLPs | 0, 8, 24 |
| 2 | 50 μg | gB/pp65 bivalent VLPs | 0, 8, 24 |
| 3 | 25 μg | gB/pp65 bivalent VLPs | 0, 8, 24 |
| 4 | 100 μg | gH-G/pp65 bivalent VLPs | 0, 8, 24 |
| 5 | 25 μg | gH-G/pp65 bivalent VLPs | 0, 8, 24 |
| 6 | 100 μg each | gB/pp65 bivalent VLPs + gH-G/pp65 bivalent VLPs (1:1 ratio) | 0, 8, 24 |
| 7 | 25 μg each | gB/pp65 bivalent VLPs + gH-G/pp65 bivalent VLPs (1:1 ratio) | 0, 8, 24 |

Figure 9:
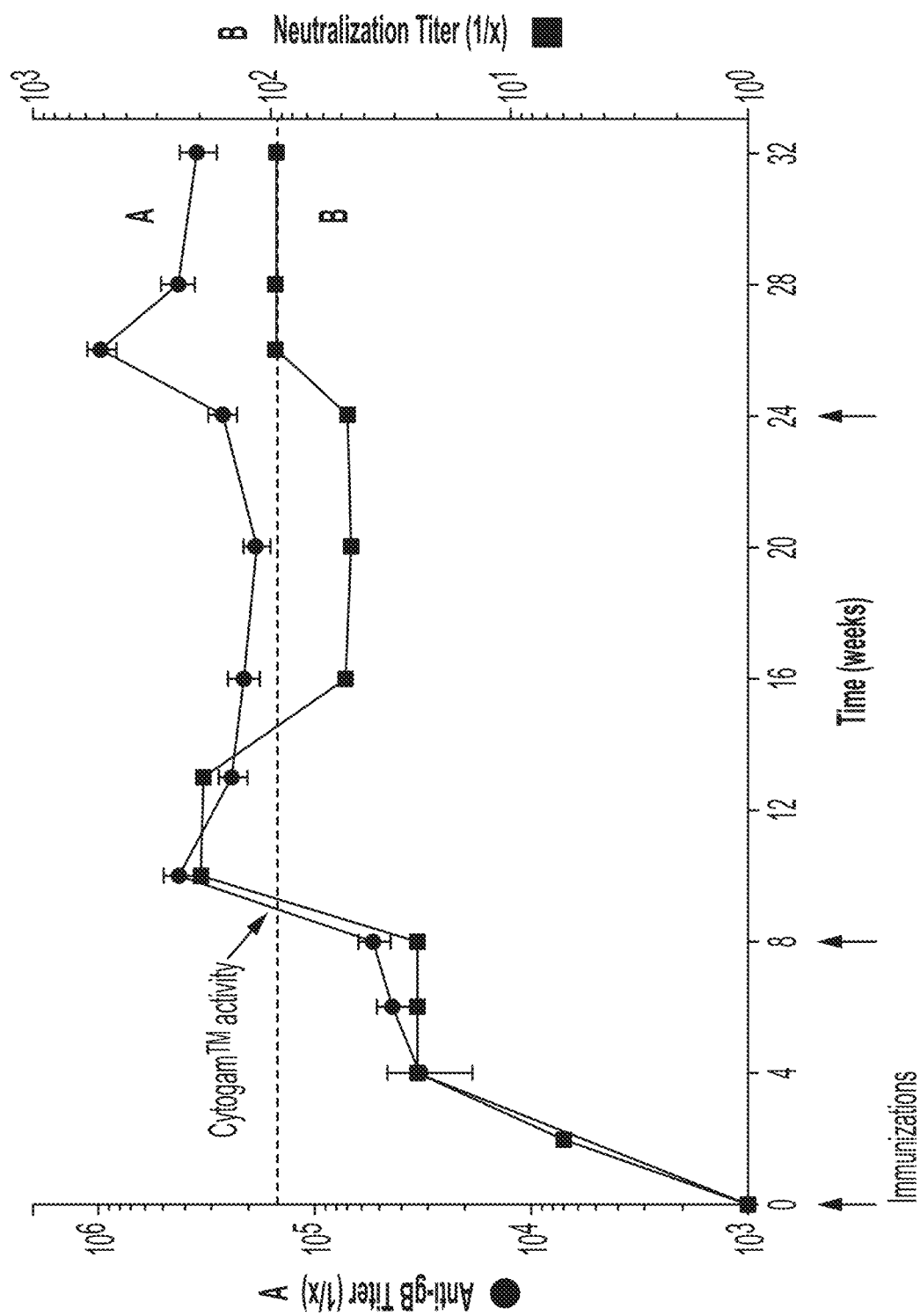
FIG. 9 shows anti-gB and neutralizing antibody titers in rabbits treated with exemplary VLP compositions expressed in HEK 293 cells (assayed in human fibroblast cells).

Individual rabbit sera was tested for reactivity against recombinant gB antigen by ELISA (plotted on left axis FIG. 9A). Neutralizing antibody responses to HCMV was determined using a microneutralization assay in fibroblast cells based on a GFP-expressing CMV virus (TB40) and flow cytometric analysis of infected (GFP+) HFF cells as described in Example 4 (plotted on right axis FIG. 9B). Rabbit sera collected pre- and post-immunizations as described were pooled and tested for neutralizing activity in the presence of complement against HCMV expressing GFP in HFF fibroblasts relative to a positive control CMV hyperglobulin, Cytogam™. Endpoint titers are plotted and represent a 50% reduction in CMV-infected cells relative to matched pre-immunization sera (plotted on left axis FIG. 9A). 50,000 cells were collected during flow cytometric analysis of infected (GFP+) cells (plotted on right axis FIG. 9B). As shown in FIG. 9, the bivalent gB/Gag/pp65 VLP composition elicited high titer binding (A) and high titer neutralizing antibody (B) responses in rabbits against fibroblast cell infection.

Figure 10:
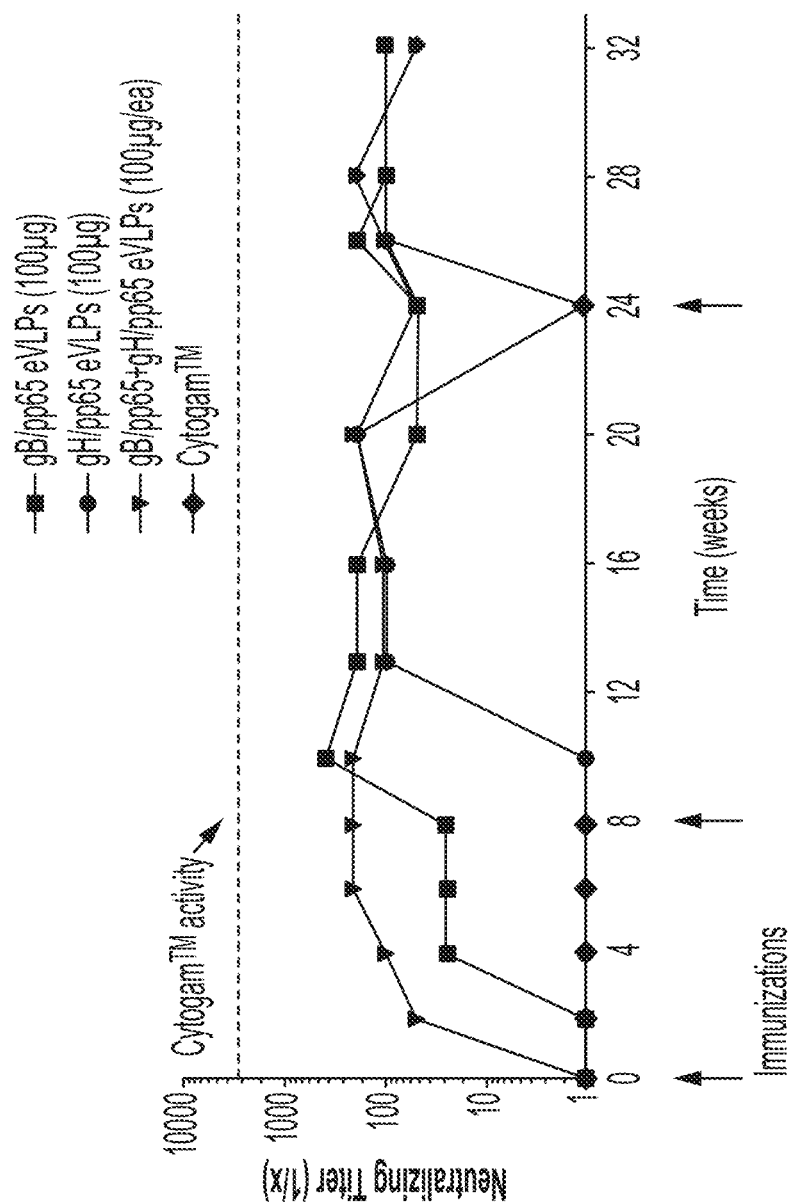
FIG. 10 shows neutralizing antibody titers in rabbits treated with exemplary VLP compositions expressed in HEK 293 cells (assayed in human epithelial cells).

Pooled rabbit sera was also tested for neutralizing antibody responses to HCMV using a microneutralization assay in epithelial cells based on a GFP-expressing HCMV virus (Towne TS15-rR) and flow cytometric analysis of infected (GFP+) ARPE-19 cells. Rabbit sera collected pre- and post-immunizations as described were pooled and tested for neutralizing activity in the presence of complement against HCMV expressing GFP in ARPE-19 epithelial cells relative to a positive control CMV hyperglobulin, Cytogam™. As shown in FIG. 10, surprisingly, the combination of bivalent gB/Gag/pp65 and bivalent gH-G/Gag/pp65 VLP composition elicited a synergistic and more rapid neutralizing antibody response in rabbits against epithelial cell infection, relative to gB/Gag/pp65 or gH/Gag/pp65.

As can be seen (or as will be appreciated by those skilled in the art having read the present specification), the data demonstrate, among other things, surprisingly good activity of VLPs, such as by a combination of VLPs that include gB/Gag/pp65 and VLPs that include gH-G/Gag/pp65, even as compared with VLPs that include gB/Gag/pp65 or VLPs that include gH-G/Gag/pp65.

Example 6: Scaled-Up Production and Purification of Virus-Like Particles (VLPs)

VLPs were produced and purified as follows. CHO cells were transfected at a cell density between 1.5E06 to 2.0E06 cells/mL with plasmids of choice (prepared as described in Example 1) at predetermined concentrations and ratios. Stuffer DNA was added to make total DNA concentration up to 1 µg/mL cell culture. The plasmids used for transfection were first purified by MaxiPrep or GigaPrep plasmid purification kits (Qiagen). The PEIMAX used for transfection to deliver DNA to the cells was provided at a ratio of 6:1 (PEI:DNA wt/wt). The cells were cultured for 72 hours, and then the cultures were centrifuged at 4000 rpm for 20 minutes, using rotor JS-4.2A by Beckman Coulter, in 1 L bottles. The supernatant was filtered through 0.8/0.45 µm filter (AcroPak 500 Capsule, Pall). The filtered supernatant was then concentrated by Tangential Flow Filtration (TFF) and diafiltered against histidine-containing buffer. The diafiltered material was loaded onto an anion exchange chromatography column (AEX) where the flowthrough was collected. The flowthrough was then sterile filtered through 0.45 µm to be aliquoted in different volumes.

The TFF procedure involved overnight sanitization of two TFF membranes (Pellicon 2 Mini 500 kDa cutoff, 0.1 m$^2$ surface area) in 0.5 M NaOH by fixing them in parallel in a stainless-steel housing. After running water to neutral pH on the retentate as well as on the permeate side, the phosphate buffer (PBS) was used to equilibrate the membrane. The filtered supernatant was then loaded into the TFF retentate recirculation loop. The starting inlet pressure was 10.5 psi at a permeate flow rate of 400 mL/min that reduced to about 200 mL/min at the end of concentration. After concentration to about 10 to 20 times, diafiltration with 5 volumes of 20 mM Histidine+150 mM NaCl, pH 5.5 was done. The diafiltered material was collected and rinsed with an equal volume of his-buffer after recirculating for another 5 minutes with permeate flow closed. The retentate was then collected and pooled with the previously collected retentate. To maintain the functionality of the membranes, the membranes were rinsed with PBS for 10 minutes; with 0.5 M NaOH for 40 minutes (after flushing 200 mL to waste through permeate and retentate); and finally with water to neutral pH in retentate and permeate. The membranes were then stored in 0.1 M NaOH solution in a refrigerator.

AEX column chromatography was used to reduce DNA content, using a 20 mL HiLoad 16/10 Sepharose HP column at a flow rate of 1.6 mL/min for equilibration with equilibration buffer (20 mM Histidine+150 mM NaCl, pH 5.5), and a flow rate of 3.2 mL/min for the loading, washing and stripping steps. Cleaning procedures were performed at 0.8 mL/min. A chart recorder was used to monitor the UV absorbance at 280 nm. A Gradifrac chromatography system (GE Healthcare) was used, which was sanitized before use. First ethanol (20% v/v present in the column as a storage buffer) was removed from the column using 5 column volumes of Super Q Water (low endotoxins). The equilibrium buffer was passed for 5 column volumes, followed by 5 column volumes of stripping buffer (20 mM Histidine+1000 mM NaCl, pH 5.5) to condition the column. The equilibration buffer was passed for 5 column volumes again to prepare the column for loading. Loading was performed at 3.2 mL/min, after which the column was washed with 5 column volumes of equilibration buffer, or until the base line was observed. The flowthrough was collected from the onset of the UV peak until the drop of UV peak to about 10% of the maximum peak height of the UV absorbance during the loading of the material. The column was then stripped by 5 column volumes of stripping buffer (20 mM Histidine+1000 mM NaCl, pH 5.5) and the peak was collected. This was followed by 5 column volumes of another stripping buffer (20 mM Histidine+2000 mM NaCl, pH 5.5) to remove any strongly bound proteins and nucleic acids and the peak was collected. The column was then cleaned with 1M NaOH to remove any precipitated proteins at 0.8 mL/min for 4 column volumes. The column was then rinsed with water at 0.8 ml/min to neutral pH (normally 4-5 column volumes). The column was then passed by 20% ethanol (4 column volumes at 0.8 mL/min) to remove any lipoproteins or lipids (2 column volumes). At this stage the column was either stored or rinsed with water (4 column volumes) to restart the cycle for a second batch.

Figure 11B:
FIG. 11B shows negative-staining Electron Microscopy (EM) images of exemplary VLP compositions expressed in CHO cells purified by Anion Exchange (AEX) Chromatography.
Figure 11A:
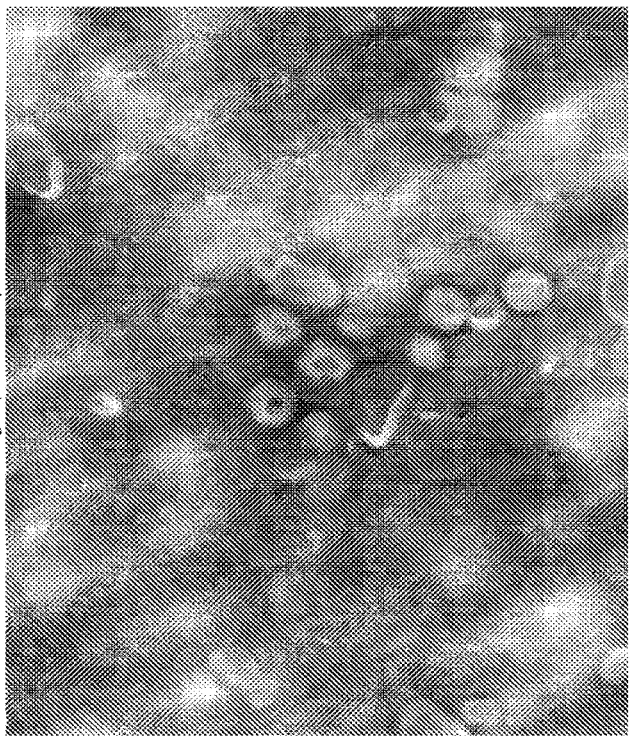
FIG. 11A shows negative-staining Electron Microscopy (EM) images of exemplary VLP compositions expressed in CHO cells purified by Tangential Flow Filtration (TFF).

FIG. 11 depicts images of a purified gB-G monovalent VLP produced from CHO cells and then subjected to TFF (FIG. 11A) and AEX (FIG. 11B) purification methods followed by negative staining Electron Microscopy analytical methods. As shown in FIG. 11, intact gB-G monovalent VLPs are present after TFF (FIG. 11A) and AEX purification (FIG. 11B).

Example 7: Immunogenicity and Neutralization Activity of Purified VLPs in Rabbits Monovalent gB-G VLP compositions prepared as described in Example 6 were tested in New Zealand White rabbits 6-8 weeks old (minimum 6 animals per test group). Rabbits were immunized intramuscularly with 0.5 ml (50 µg gB content) of VLP compositions three times, once on day 0 (Prime) and once on day 56 (week 8 Boost) and once on day 168 (week 24 Boost). To assess humoral immune responses in rabbits, blood was collected from all rabbits in the study groups pre-1$^{st}$ immunization and then post-1$^{st}$ immunization at 2, 4, 6 and 8 weeks and post-2$^{nd}$ immunization at 10, 13, 16, 20 and 24 weeks from study start. The study design is summarized in Table 4.

TABLE 4

| Test Article # | Dose | Test Article Description | Immunization Schedule (weeks) |
| --- | --- | --- | --- |
| 1 | 50 µg gB content | gB-G monovalent VLPs (TFF & AEX purified) | 0, 8, 24 |

Figure 12:
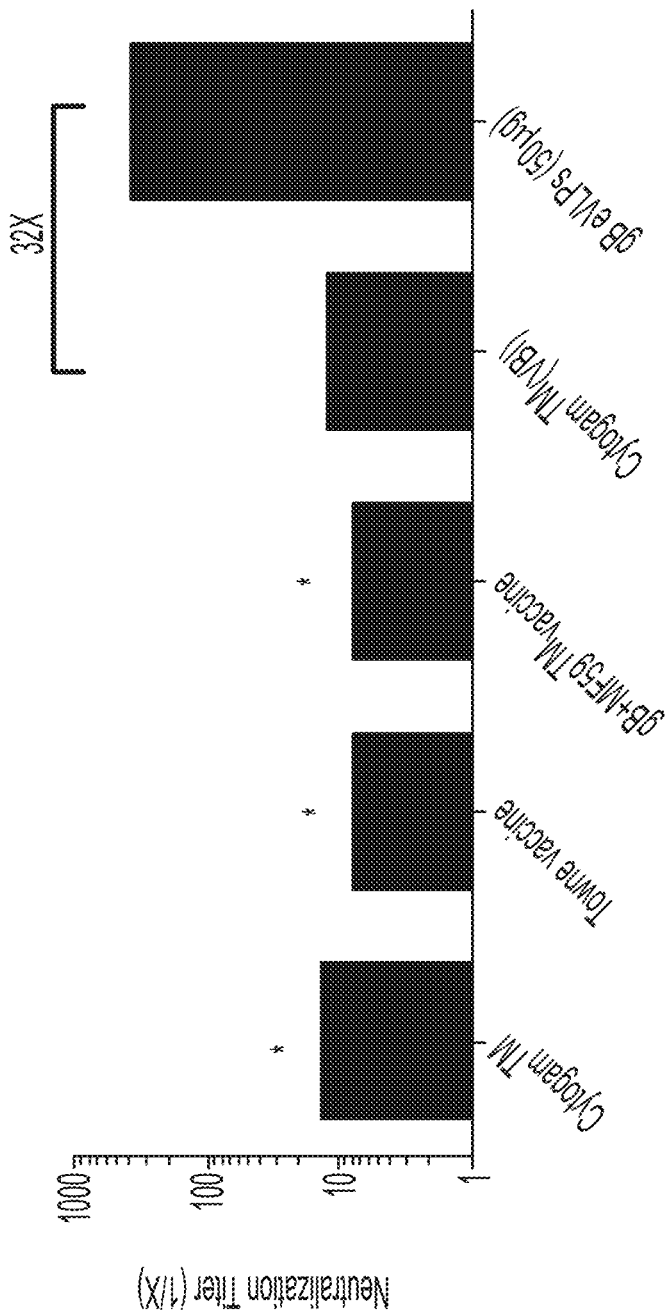
FIG. 12 shows neutralizing antibody titers in rabbits treated with exemplary VLP compositions expressed in CHO cells and purified by Tangential Flow Filtration (TFF) and Anion Exchange (AEX) Chromatography (assayed in human fibroblast cells).

FIG. 12 depicts the potent neutralization of fibroblast cell infection that was elicited by serum from rabbits immunized with TFF/AEX purified CHO cell-produced gB-G monovalent VLPs ("gB eVLPs" in FIG. 12). This neutralization was superior to that achieved with a positive control CMV hyperglobulin, Cytogam™. FIG. 12 also includes published neutralization titer data for Towne Vaccine and adjuvanted gB subunit vaccine (gB+MF59™) (Cui X et al. 2008 Vaccine 26:5760-5766).

Figure 13:
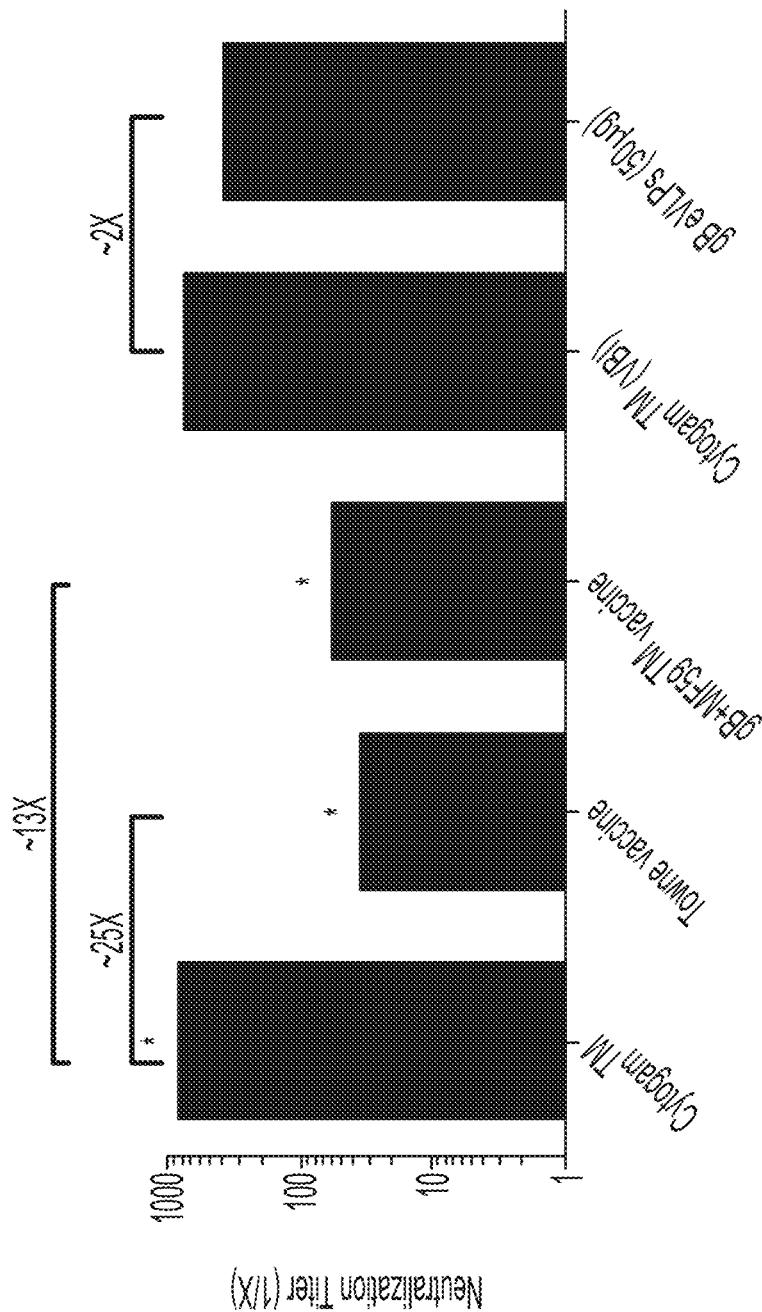
FIG. 13 shows neutralizing antibody titers in rabbits treated with exemplary VLP compositions expressed in CHO cells purified by Tangential Flow Filtration (TFF) and Anion Exchange (AEX) Chromatography (assayed in human epithelial cells).

FIG. 13 illustrates potent neutralization of epithelial cell infection that was elicited by serum from rabbits immunized with TFF/AEX purified CHO cell-produced gB-G monovalent VLPs ("gB eVLPs" in FIG. 13). This neutralization was comparable to that achieved with a positive control CMV hyperglobulin, Cytogam™. FIG. 13 also includes published neutralization titer data for Towne Vaccine and adjuvanted gB subunit vaccine (gB+MF59™) (Cui X et al. 2008 Vaccine 26:5760-5766).

Figure 14:
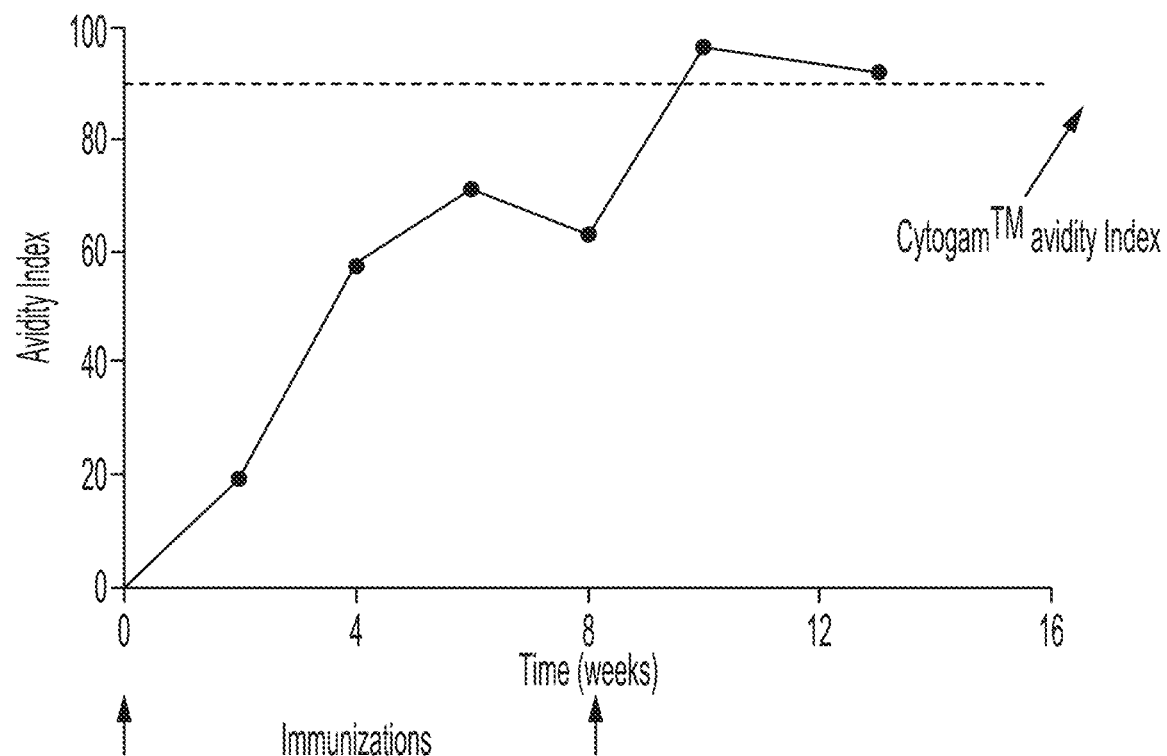
FIG. 14 shows the avidity index of antibodies produced in rabbits treated with exemplary VLP compositions expressed in CHO cells and purified by Tangential Flow Filtration (TFF) and Anion Exchange (AEX) Chromatography.

FIG. 14 depicts the avidity index of antibodies elicited in rabbits immunized with TFF/AEX purified CHO cell-produced gB-G monovalent VLP compositions. Pooled rabbit sera and a positive control CMV hyperglobulin, Cytogam™ were diluted 1:600,000 and tested against full length recombinant gB antigen by ELISA in the presence or absence of 5M urea. Antibody avidity was determined as previously described (Marshall BC and Adler S 2003 Viral Immunol 16:491-500). As shown in FIG. 14, a rapid induction of high avidity neutralizing antibodies was elicited in rabbits by immunization with TFF/AEX purified CHO cell-produced gB-G monovalent VLPs. Maximal antibody avidity was achieved after two gB-G VLP immunizations.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

BRIEF DESCRIPTION OF SEQUENCE LISTING

SEQ ID NO:1 depicts an MMLV Gag Amino Acid Sequence.
SEQ ID NO:2 depicts an MMLV Gag Nucleotide Sequence.
SEQ ID NO:3 depicts a Codon Optimized MMLV Gag Nucleotide Sequence.
SEQ ID NO:4 depicts an MMLV Gag—CMV pp65 Amino Acid Sequence.
SEQ ID NO:5 depicts an MMLV Gag—CMV pp65 Nucleotide Sequence.
SEQ ID NO:6 depicts a Codon Optimized MMLV Gag—CMV pp65 Nucleotide Sequence.
SEQ ID NO:7 depicts an HCMV gB Amino Acid Sequence.
SEQ ID NO:8 depicts an HCMV gB Nucleotide Sequence.
SEQ ID NO:9 depicts a Codon Optimized HCMV gB Nucleotide Sequence.
SEQ ID NO:10 depicts an HCMV gB-G Amino Acid Sequence.
SEQ ID NO:11 depicts an HCMV gB—G Nucleotide Sequence.
SEQ ID NO:12 depicts a Codon Optimized HCMV gB—G Nucleotide Sequence.
SEQ ID NO:13 depicts an HCMV gH Amino Acid Sequence.
SEQ ID NO:14 depicts an HCMV gH Nucleotide Sequence.
SEQ ID NO:15 depicts a Codon Optimized HCMV gH Nucleotide Sequence.
SEQ ID NO:16 depicts an HCMV gH—G Amino Acid Sequence.
SEQ ID NO:17 depicts an HCMV gH—G Nucleotide Sequence.
SEQ ID NO:18 depicts a Codon Optimized HCMV gH—G Nucleotide Sequence.
SEQ ID NO:19 depicts a Propol II Expression Plasmid Nucleotide Sequence.
SEQ ID NO:20 depicts an HCMV gH—HCMV gB TM/CTD Nucleotide Sequence.
SEQ ID NO:21 depicts a Codon Optimized MMLV Gag Nucleotide Sequence.
SEQ ID NO:22 depicts a Codon Optimized MMLV Gag—CMV pp65 Nucleotide Sequence.

What is claimed is:

1. A virus-like particle (VLP) comprising:
a first polypeptide comprising an amino acid sequence that is at least 95% identical to the amino acid sequence of SEQ ID NO:1; and
a second polypeptide comprising a transmembrane modified gH polypeptide comprising an amino acid sequence that is at least 95% identical to SEQ ID NO:16.

2. The VLP of claim 1, wherein the second polypeptide comprises an amino acid sequence that is at least 97% identical to SEQ ID NO:16.

3. The VLP of claim 1, wherein the second polypeptide comprises an amino acid sequence that is at least 99% identical to SEQ ID NO:16.

4. The VLP of claim 1, wherein the second polypeptide comprises the amino acid sequence of SEQ ID NO:16.

5. The VLP of claim 1, further comprising a third polypeptide comprising a gB polypeptide.

6. The VLP of claim 5, wherein the third polypeptide comprises an amino acid sequence that is at least 85% identical to SEQ ID NO:7.

7. The VLP of claim 5, wherein the gB polypeptide is a transmembrane modified gB polypeptide.

8. The VLP of claim 7, wherein the transmembrane modified gB polypeptide comprises a transmembrane domain found in nature in a vesicular stomatitis virus (VSV) protein.

9. The VLP of claim 8, wherein the transmembrane modified gB polypeptide comprises an amino acid sequence at least 85% identical to SEQ ID NO:10.

10. A transmembrane modified gH polypeptide comprising an amino acid sequence at least 95% identical to SEQ ID NO:16.

11. The transmembrane modified gH polypeptide of claim 10, comprising an amino acid sequence at least 97% identical to SEQ ID NO:16.

12. The transmembrane modified gH polypeptide of claim 10, comprising an amino acid sequence at least 99% identical to SEQ ID NO:16.

13. The transmembrane modified gH polypeptide of claim 10, comprising the amino acid sequence of SEQ ID NO:16.

14. A virus-like particle (VLP) comprising the polypeptide of claim 10.

15. A vector comprising a nucleotide sequence encoding the polypeptide of claim 10.

16. A method for the production of a virus-like particle (VLP), the method comprising:
co-transfecting a host cell with:
a first vector comprising a nucleotide sequence encoding a polypeptide comprising an amino acid sequence that is at least 95% identical to the amino acid sequence of SEQ ID NO:1; and
a second vector comprising a nucleotide sequence encoding a polypeptide comprising an amino acid sequence that is at least 95% identical to the amino acid sequence of SEQ ID NO:16; and
cultivating the host cell in a suitable medium under conditions allowing the expression of the polypeptides encoded by the vectors.

17. A method for reducing frequency or severity or delaying onset of symptoms of HCMV infection in a subject, the method comprising administering to the subject a pharmaceutical composition comprising the VLP of claim 1.

* * * * *